US007105307B2

(12) United States Patent
Colyer et al.

(10) Patent No.: US 7,105,307 B2
(45) Date of Patent: *Sep. 12, 2006

(54) COMPOSITIONS AND METHODS FOR SCREENING FOR MODULATORS OF ENZYMATIC ACTIVITY

(75) Inventors: John Colyer, Leeds (GB); Derek N. Woolfson, Brighton (GB); Joanne Lightowler, York (GB)

(73) Assignee: Cyclacel, Ltd., Scotland (GB)

( * ) Notice: Subject to any disclaimer, the term of this patent is extended or adjusted under 35 U.S.C. 154(b) by 172 days.

This patent is subject to a terminal disclaimer.

(21) Appl. No.: 10/161,205

(22) Filed: Jun. 3, 2002

(65) Prior Publication Data

US 2003/0100037 A1    May 29, 2003

Related U.S. Application Data

(63) Continuation of application No. 09/511,047, filed on Feb. 23, 2000, now abandoned, which is a continuation-in-part of application No. 09/146,549, filed on Sep. 3, 1998, now abandoned.

(30) Foreign Application Priority Data

Aug. 30, 1997  (GB) .................. 9718358.6
Sep. 1, 1998   (GB) .................. PCT/GB98/02565

(51) Int. Cl.
*G01N 33/53*    (2006.01)
*G01N 33/573*   (2006.01)
*G01N 33/542*   (2006.01)

(52) U.S. Cl. .................. 435/7.1; 435/7.4; 435/7.8; 435/7.91; 435/183; 530/350

(58) Field of Classification Search ................ 530/350; 435/69.7, 69.1, 7.1, 7.4, 7.8
See application file for complete search history.

(56) References Cited

FOREIGN PATENT DOCUMENTS

| WO | WO 92/00388 | 1/1992 |
|----|-------------|--------|
| WO | WO 93/15210 | 8/1993 |
| WO | WO 96/13607 | 5/1996 |
| WO | WO 97/00267 | 1/1997 |
| WO | WO 97/07402 | 2/1997 |
| WO | WO 97/12988 | 4/1997 |
| WO | WO 97/28261 | 8/1997 |
| WO | WO 97/31016 | 8/1997 |
| WO | WO 97/31113 | 8/1997 |
| WO | WO 97/39326 | 10/1997 |
| WO | WO 97/41424 | 11/1997 |
| WO | WO 98/02571 | 1/1998 |
| WO | WO 98/06737 | 2/1998 |

OTHER PUBLICATIONS

Adams et al. Optical Probes for Cyclic AMP. In: Fluorescent and Luminescent Probes for Biological Activity. Ed: Mason, W.T., Academic Press, 1993, p. 133-149.*

(Continued)

*Primary Examiner*—Michael Borin
(74) *Attorney, Agent, or Firm*—Elizabeth N. Spar; Kathleen M. Williams; Edwards Angell Palmer & Dodge LLP

(57) ABSTRACT

The invention provides a method to screen for a modulator of enzymatic activity comprising the step of monitoring the association or dissociation of a pair of polypeptides which can associate as a dimer. The polypeptide pair comprises a first polypeptide comprising detection means and a site of post-translational modification and a second polypeptide comprising detection means.

34 Claims, 16 Drawing Sheets

OTHER PUBLICATIONS

Kammerer et al. Matrix Biol., Mar. 1997, vol. 15, 555-565.*
Broudy et al. Blood (1998), 91(3), 898-906.*
Gadella et al. Journal of Cell Biology (1995), 129(6), 1543-58.*
Post et al. Molecular Biology of Cell, vol. 6, 1755-1768, 1995.*
Atkinson et al . Database Caplus, DN 115:66862; Journal of Cell Science, Supplement (1991), 14(Mot. Proteins), 7-10.*
Copy of Information Disclosure Statement Form PTO-1449 submitted in the parent case U.S. Appl. No. 09/258,452, filed Feb. 23, 2000.
Copy of International Search Report dated Jan. 29, 1999 in the International Application No. PCT/GB98/02565.
Bachmair, Andreas, *Cell*, vol. 56: 1019-1032.
Cox, Adrienne, *Methods in Enzymology*, vol. 250: 105-121.
Graf et al., *Molecular Pharmacology*, 42: 760-764.
Hershko and Ciechanover, *Annu. Rev. Biochem*, 1992, 61: 761-807.
Kemp and Pearson, *Methods in Enzymology*, vol. 200:121-134.
Lupas, Andrei, *TIBS 21*, Oct. 1996: 375-380.
Milligan et al., *TIBS 20*, May 1995: 181-186.
Rechsteiner and Rogers, TIBS 21, 1996: 267-271.
Siddiqui et al., *J. of Biol. Chem.*, vol. 273, 1998:3712-3717.
Songyang et al., *Cell*, vol. 72, 1993: 767-778.
Stover et al., *J. of Biochem.*, vol. 271, 1996:12481-12487.
Swanson, et al., *TIBS 19*, Nov. 1994:485-490.
Takeda and Kinoshita, *TIBS 20*, Sep. 1995: 367-371.
Uchida, et al., *Proc.Natl. Acad. Sci. USA*, vol. 90, 1993: 3841-3485.
Udenfried and Kodukula, *Annu. Rev. Biochem*, 1995, 64: 563-591.
Wei and Matthews, *Methods in Enzymology*, vol. 200, 1991:388-414.
Weissman, *Review Immunology Today*, vol. 4, Apr. 1997: 189-198.

* cited by examiner

1 - AUTOCAMTIDE II PHOSPHORYLATED BY CaMKII IN THE PRESENCE OF $Ca^{2+}$ AND CALMODULIN
2 - ZIP4S PHOSPHORYLATED BY PKA
3 - ZIP4S PHOSPHORYLATED BY CaMKII IN THE PRESENCE OF Ca2+ AND CALMODULIN
4 - AUTOCAMTIDE II PHOSPHORYLATED BY CaMKII IN THE PRESENCE OF CALMODULIN ($Ca^{2+}$ ABSENT)

COMPOSITIONS AND METHODS FOR SCREENING FOR MODULATORS OF ENZYMATIC ACTIVITY

RELATED APPLICATIONS

The present application is a continuation of U.S. Ser. No. 09/511,047, filed on Feb. 23, 2000 now abandoned, which is a continuation-in-part of U.S. Ser. No. 09/146,549, filed on Sep. 3, 1998 now abandoned, which claims priority to PCT/GB98/02565, filed on Sep. 1, 1998 and GB 9718358.6 filed on Aug. 30, 1997.

FIELD OF THE INVENTION

This invention relates to a new polypeptide reporter molecule for monitoring the interaction of peptides as a function of the addition or subtraction of a chemical moiety to one of the reporter molecules by a protein modifying enzyme; and/or chemical modification resulting in the dissociation of the reporter molecules that would naturally associate.

BACKGROUND OF THE INVENTION

The post-translational modification of proteins have been known for over 40 years and since then has become a ubiquitous feature of protein structure. The addition of biochemical groups to translated polypeptides has wide-ranging effects on protein stability, protein secondary/tertiary structure, enzyme activity and in more general terms on the regulated homeostasis of cells. Such additions include, but are not limited to, phosphorylation, glycosylation, ADP-ribosylation and ubiquitination.

Phosphorylation is a well-studied example of a post-translational modification of protein. There are many cases in which polypeptides form higher order tertiary structures with like polypeptides (homo-oligomers) or with unalike polypeptides (hetero-oligomers). In the simplest scenario, two identical polypeptides associate to form an active homodimer. An example of this type of association is the natural association of myosin II molecules in the assembly of myosin into filaments.

The dimerization of myosin II monomers is the initial step in seeding myosin filaments. The initial dimerization is regulated by phosphorylation the effect of which is to induce a conformational change in myosin II secondary structure resulting in the folded 10S monomer subunit extending to a 6S molecule. This active molecule is able to dimerize and subsequently to form filaments. The involvement of phosphorylation of myosin II in this priming event is somewhat controversial. Although in higher eukaryotes the conformational change is dependant on phosphorylation, in Ancanthoamoeba, a lower eukaryote, the post-translational addition of phosphate is not required to effect the initial dimerization step. It is of note that the dimerization domains in myosin II of higher eukaryotes contain the sites for phosphorylation and it is probable that phosphorylation in this region is responsible for enabling myosin II to dimerize and subsequently form filaments. In Dictyostelium this situation is reversed in that the phosphorylation sites are outside the dimerization domain and phosphorylation at these sites is required to effect the disassembly of myosin filaments. In contrast to both these examples, Acanthoamoeba myosin II is phosphorylated in the dimerization domain but this modification is not necessary to enable myosin II monomers to dimerize in this species.

By far the most frequent example of post-translational modification is the addition of phosphate to polypeptides by specific enzymes known as protein kinases. These enzymes have been identified as important regulators of the state of phosphorylation of target proteins and have been implicated as major players in regulating cellular physiology. For example, the cell-division-cycle of the eukaryotic cell is primarily regulated by the state of phosphorylation of specific proteins the functional state of which is determined by whether or not the protein is phosphorylated. This is determined by the relative activity of protein kinases which add phosphate and protein phosphatases which remove the phosphate moiety from these proteins. Clearly dysfunction of either the kinases or phosphatases may lead to a diseased state. This is best exemplified by the uncontrolled cellular division shown by tumor cells. The regulatory pathway is composed of a large number of genes that interact in vivo to regulate the phosphorylation cascade that ultimately determines if a cell is to divide or arrest cell division.

Currently there are several approaches to analysing the state of modification of target proteins in vivo:

1. In vivo incorporation of labeled (for example, radiolabeled) moieties (e.g., phosphate, ubiquitin or ADP-ribosyls, which are added to target proteins.
2. Back-labeling. The incorporation of a labeled moiety into a protein in vitro to estimate the state of modification in vivo.
3. The use of cell-membrane-permeable protein-modifying enzyme inhibitors (e.g., Wortmannin, staurosporine) to block modification of target proteins and comparable inhibitors of the enzymes involved in other forms of protein modification (above).
4. Western blotting, of either 1- or 2-dimensional gels bearing test protein samples, in which modification is detected using antibodies specific for modified forms of target proteins.
5. The exploitation of eukaryotic microbial systems to identify mutations in protein-modifying enzymes.

These strategies have certain limitations. Monitoring states of modification by pulse or steady-state labelling is merely a descriptive strategy to show which proteins are modified when samples are separated by gel electrophoresis and visualized by autoradiography. This is unsatisfactory, due to the inability to identify many of the proteins that are modified. A degree of specificity is afforded to this technique if it is combined with immunoprecipitation; however, this is of course limited by the availability of antibodies to target proteins. Moreover, only highly-expressed proteins are readily detectable using this technique, which may fail to identify many low-abundance proteins, which are potentially important regulators of cellular functions.

The use of enzyme inhibitors to block activity is also problematic. For example, very few kinase inhibitors have adequate specificity to allow for the unequivocal correlation of a given kinase with a specific kinase reaction. Indeed, many inhibitors have a broad inhibitory range. For example, staurosporine is a potent inhibitor of phospholipid/$Ca^{+2}$ dependant kinases. Wortmannin is some what more specific, being limited to the phosphatidylinositol-3 kinase family. This is clearly unsatisfactory because more than one biochemical pathway may be affected during treatment making the assignment of the effects almost impossible.

Finally, yeast (*Saccharomyces cervisiae* and *Schizosaccharomyces pombe*) has been exploited as a model organism for the identification of gene function using recessive mutations. It is through research on the effects of these mutations that the functional specificities of many protein-modifying enzymes have been elucidated. However, these molecular genetic techniques are not easily transferable to higher eukaryotes, which are diploid and therefore not as genetically tractable as these lower eukaryotes.

An example of heterodimer association is described in patent application number WO92/00388. It describes an adenosine 3:5 cyclic monophosphate (cAMP) dependent protein kinase which is a four-subunit enzyme being composed of two catalytic polypeptides (C) and two regulatory polypeptides (R). In nature the polypeptides associate in a stoichiometry of $R_2C_2$. In the absence of cAMP the R and C subunits associate and the enzyme complex is inactive. In the presence of cAMP the R subunit functions as a ligand for cAMP resulting in dissociation of the complex and the release of active protein kinase. The invention described in WO92/00388 exploits this association by adding fluorochromes to the R and C subunits.

The polypeptides are labeled (or 'tagged') with fluorophores having different excitation/emission wavelengths. The excitation and emission of one such fluorophore effects a second excitation/emission event in the second fluorophore. By monitoring the fluorescence emission of each fluorophore, which reflects the presence or absence of fluorescence energy transfer between the two, it is possible to derive the level of association between the R and C subunits as a function of cAMP concentration. Therefore, the natural affinity of the C subunit for the R subunit has been exploited to monitor the concentration of a specific metabolite, namely cAMP.

The prior art teaches that intact, fluorophore-labeled proteins can function as reporter molecules for monitoring the formation of multi-subunit complexes from protein monomers; however, in each case, the technique relies on the natural ability of the protein monomers to associate.

Tsien et al. (WO97/28261) teach that fluorescent proteins having the proper emission and excitation spectra that are brought into physically close proximity with one another can exhibit fluorescence resonance energy transfer ("FRET"). The invention of WO97/28261 takes advantage of that discovery to provide tandem fluorescent protein constructs in which two fluorescent protein moieties capable of exhibiting FRET are coupled through a linker to form a tandem construct. In the assays of the Tsien application, protease activity is monitored using FRET to determine the distance between fluorophores controlled by a peptide linker and subsequent hydrolysis thereof. Other applications rely on a change in the intrinsic fluorescence of the protein as in the kinase assays of WO98/06737.

The present invention instead encompasses the use of FRET to monitor the association of polypeptides, as described herein, which are labeled with fluorescent moieties (protein and chemical); in the invention, FRET indicates the proximity of two labeled polypeptide binding partners, which labeled partners associate either in the presence or absence of a given post-translational modification to an engineered site which has been introduced into at least one of the partners, but not into the fluorophore, reflecting the modification state of one or both of the binding partners and, consequently, the level of activity of a protein-modifying enzyme.

There is a need in the art for efficient means of monitoring and/or modulating post-translational protein modification. Further, there is a need to develop a technique whereby the addition/removal of a modifying group can be monitored continuously during real time to provide a dynamic assay system that also has the ability to resolve spatial information.

SUMMARY OF THE INVENTION

The invention provides an isolated polypeptide, or a fragment thereof, comprising at least one engineered site sufficient for the addition of at least one chemical or biological "moiety", i.e., a group, that is one of a phosphate, ubiquitin, glycosyl or ADP-ribosyl moiety, wherein the polypeptide binds to at least one binding partner in at least one of the following manners: phosphorylation-, ubiquitination-, glycosylation- or ADP-ribosylation-dependent manner.

Reference herein to the term "isolated polypeptide" comprises reference to a polypeptide that forms a coiled-coil structure. Coiled-coil structures are well known to those skilled in the art but a description is also provided hereinafter.

As used herein, the term "isolated polypeptide" refers to a synthetic polypeptide containing or consisting of at least one coiled-coil or a natural polypeptide comprising at least one coiled-coil structure, so long as the polypeptide has a binding partner and so long as binding of the polypeptide to its binding partner is dependent upon the presence or absence of a "moiety" at an engineered site, which site is present in one or both of the isolated polypeptide and its binding partner.

The invention also pertains to a synthetic polypeptide containing at least one coiled-coil and containing at least one amino acid already modified by a moiety that is one of a phosphate, ubiquitin, glycosyl or ADP-ribosyl moiety, wherein the synthetic polypeptide binds to a binding partner in a phosphorylation-, ubiquitination-, glycosylation- or ADP-ribosylation-dependent manner, such that the moiety may be removed by an enzyme.

According to the invention, binding of an isolated or synthetic polypeptide and its binding partner(s) is dependent upon addition or removal of at least one moiety, which addition or removal may occur on one or both of the isolated polypeptide and its binding partner.

An "engineered site" suitable for addition or removal of a "moiety" is placed within an isolated polypeptide or binding partner thereof of the invention at a position such that formation of a dimer between the isolated polypeptide and its binding partner is dependent upon the presence or absence of the "moiety"; and preferably does not overlap with an amino acid which is part of a fluorescent tag.

Similarly, the amino acid that includes a "moiety" as described herein may be positioned anywhere within the synthetic polypeptide such that formation of a dimer between the synthetic polypeptide and its binding partner is dependent upon the presence or absence of the moiety.

As used herein, the term "binding partner" refers to a polypeptide or fragment thereof (a peptide) that binds to (associates with) a polypeptide comprising a coiled-coil according to the invention. A binding partner usually will contain a coiled-coil and an engineered site, if these are required for binding, but does not necessarily have to contain these elements if they are not required for binding.

It is contemplated that the position at which an engineered site or an amino acid containing a moiety is to reside is initially determined by random placement of the site within the polypeptide or binding partner, followed by testing by methods described herein of the ability of the isolated or synthetic polypeptide and its binding partner to associate or not, depending upon the presence of absence of a moiety. A pair of binding partners, of which at least the isolated polypeptide comprises a site so placed and which is found to display modification-dependent association, is of use in the assays of the invention.

As used herein, the terms "polypeptide" and "peptide" refer to a polymer in which the monomers are amino acids and are joined together through peptide or disulfide bonds. "Polypeptide" refers to either a full-length naturally-occurring amino acid chain or a "fragment thereof" or "peptide", such as a selected region of the polypeptide that is of interest in a binding assay and for which a binding partner is known or determinable. "Fragment thereof" thus refers to an amino acid sequence that is a portion of a full-length polypeptide, between about 8 and about 500 amino acids in length, preferably about 8 to about 300, more preferably about 8 to about 200 amino acids, and even more preferably about 10 to about 50 or 100 amino acids in length. "Peptide" refers to a short amino acid sequence that is 10–40 amino acids long, preferably 10–35 amino acids. Additionally, unnatural amino acids, for example, β-alanine, phenyl glycine and homoarginine may be included. Commonly-encountered amino acids which are not gene-encoded may also be used in the present invention. All of the amino acids used in the present invention may be either the D- or L-optical isomer. The L-isomers are preferred. In addition, other peptidomimetics are also useful, e.g. in linker sequences of polypeptides of the present invention (see Spatola, 1983, in *Chemistry and Biochemistry of Amino Acids, Peptides and Proteins*, Weinstein, ed., Marcel Dekker, New York, p. 267).

"Naturally-occurring" as used herein, as applied to a polypeptide or polynucleotide, refers to the fact that the polypeptide or polynucleotide can be found in nature and naturally contains a coiled-coil structure. One such example is a polypeptide or polynucleotide sequence that is present in an organism (including a virus) that can be isolated form a source in nature. Once the polypeptide is engineered as described herein it is no longer naturally ocurring but is derived from a naturally ocurring polypeptide.

"Polynucleotide" refers to a polymeric form of nucleotides of at least 10 bases in length and up to 1,000 bases or even more, either ribonucleotides or deoxyribonucleotides or a modified form of either type of nucleotide. The term includes single and double stranded forms of DNA.

As used herein, the term "associates" or "binds" refers to a polypeptide as described herein and its binding partner having a binding constant sufficiently strong to allow detection of binding by FRET or other detection means, which are in physical contact with each other and have a dissociation constant (Kd) of about 10 µM or lower. The contact region may include all or parts of the two molecules. Therefore, the terms "substantially dissociated" and "dissociated" or "substantially unbound" or "unbound" refer to the absence or loss of contact between such regions, such that the binding constant is reduced by an amount which produces a discernable change in a signal compared to the bound state, including a total absence or loss of contact, such that the proteins are completely separated, as well as a partial absence or loss of contact, so that the body of the proteins are no longer in close proximity to each other but may still be tethered together or otherwise loosely attached, and thus have a dissociation constant greater than 10 µM (Kd). In many cases, the Kd will be in the mM range. The terms "complex" and, particularly, "dimer", "multimer" and "oligomer" as used herein, refer to the polypeptide, peptide, protein, domain or subunit and its binding partner in the associated or bound state. More than one molecule of each of the two or more proteins may be present in a complex, dimer, multimer or oligomer according to the methods of the invention.

As used herein, "post-translational modification" of a polypeptide refers to the addition or removal of a "moiety" as described herein and does not refer to other post-translational events which do not involve addition or removal of such a moiety as described herein, and thus does not include simple cleavage of the reporter molecule polypeptide backbone by hydrolysis of a peptide bond, but does include hydrolysis of an isopeptide bond (e.g., in the removal of ubiquitin).

In an assay of the invention, post-translational modification is reversible, such that a repeating cycles of addition and removal of a modifying moiety may be observed, although such cycles may not occur in a living cell found in nature.

The term "site sufficient for the addition of" refers to an amino acid sequence which is recognized by (i.e., a recognition site for) a post-translational modifying enzyme, at which sequence modification (e.g., addition or removal of a phosphate, ubiquitin, glycosyl or ADP-ribosyl moiety) occurs. It is contemplated that a site comprises a small number of amino acids, typically from 2 to 10, less often up to 30 amino acids, and further that a site comprises fewer than the total number of amino acids present in the polypeptide.

The invention encompasses assays which measure the activity of a protein-modifying enzyme as indicated by the presence or absence of or the addition or removal of a chemical or biological moiety (e.g., addition or subtraction of a ubiquitin or ADP-ribosyl group), and does not encompass methods to detect post-translational cleavage of the reporter molecule polypeptide backbone.

As used interchangeably herein, the terms "moiety" and "group" refer to one of the post-translational added or removed groups referred to herein: i.e., one of a phosphate, ubiquitin, glycosyl or ADP-ribosyl moiety. A "fluorescent tag" or "fluorescent group" refers to either a fluorophore or a fluorescent protein or fluorescent fragment thereof.

"Fluorescent protein" refers to any protein which fluoresces when excited with appropriate electromagnetic radiation. This includes proteins whose amino acid sequences are either natural or engineered. A "fluorescent protein moiety" is a fluorescent protein or fluorescent fragment thereof. By the same token, the term "linker moiety" refers to the radical of a molecular linker that is coupled to both the donor and acceptor protein molecules, such as an amino acid sequence joining two engineered sites or two Coiled-coils or a disulfide bond between two polypeptides.

Preferably, addition of at least one of the following moieties: phosphate, ubiquitin, glycosyl or ADP-ribosyl moiety permits association of the corresponding phosphorylated-, ubiquitin-, glycosyl- or ADP-ribosyl-containing polypeptide with the binding partner.

Alternatively, it is preferred that addition of at least one of the following moieties: phosphate, ubiquitin, glycosyl or ADP-ribosyl moiety prevents association of the corresponding phosphorylated-, ubiquitin-, glycosyl- or ADP-ribosyl-containing polypeptide with the binding partner.

As used herein the term "prevents association" refers to the ability of at least one of the following: ubiquitin, glycosyl or ADP-ribosyl group to inhibit the association, as defined above, of at least two isolated polypeptides, an isolated polypeptide and a binding partner thereof or at least an isolated pair of polypeptides, as defined above, by at least 10%, preferably by 25–50%, highly preferably by 75–90% and, most preferably, by 95–100% relative the association observed in the absence of such a modification under the same experimental conditions.

It is additionally preferred that the isolated or synthetic polypeptide comprises at least one "contact site" which physically contacts or binds to said binding partner, and at least one of the contact sites of the polypeptide comprises either the engineered site sufficient for the addition of at least one of the following moieties: phosphate, ubiquitin, glycosyl or ADP-ribosyl moiety, or contains the amino acid that contains a moiety as defined herein.

Preferably, the polypeptide further comprises a detection means, the polypeptide comprising the detection means being a reporter molecule, the detection means ideally comprises a light emitting detection means, and the light emitting detection means ideally emits light of at least a fluorescent wavelength emission.

It is preferred that the light emitting detection means comprises two different fluorophores.

It is additionally preferred that the fluorophores comprise fluorescein and tetramethylrhodamine or another suitable pair.

Preferably, the polypeptide comprises a cysteine amino acid through which the light emitting means is attached via a covalent bond.

In another preferred embodiment, the light emitting detection means comprises two different fluorescent proteins.

It is preferred that the two different fluorescent proteins comprise green fluoresecent protein and red fluorescent protein.

It is additionally preferred that the two different fluorescent proteins comprise green fluorescent protein and blue fluorescent protein.

Preferably, the polypeptide comprises a coiled-coil containing a site sufficient for the addition of at least one of the following moieties: phosphate ($PO_4$), ubiquitin, glycosyl or ADP-ribosyl moiety.

It is preferred that the polypeptide associates via the coiled-coil with another coiled-coil containing polypeptide and more preferred that the polypeptide contains two coiled-coils and is therefore capable of self association via the two coiled-coils.

In another preferred embodiment, addition of a least one of the following moieties: phosphate, ubiquitin, glycosyl or ADP-ribosyl moiety permits association of the corresponding phosphate-, ubiquitin-, glycosyl- or ADP-ribosyl-containing polypeptide with another coiled-coil containing polypeptide to form a dimer.

In another preferred embodiment, addition of a least one of the-following moieties: phosphate, ubiquitin, glycosyl or ADP-ribosyl moiety prevents association of the corresponding phosphate-, ubiquitin-, glycosyl- or ADP-ribosyl-containing polypeptide with another coiled-coil containing polypeptide to form a dimer.

Another aspect of the invention is a kit for determining the enzyme activity of a selected kinase, phosphatase, UDP-N-Acetylglucosamine-Dolichyl-phosphate-N-acetylsglu-cosamine phosphotransferase, O-GlcNAc transferase, ubiquitin activating enzyme E1, ubiquitin conjugating enzyme E2, ubiquitin protein ligase E3, poly (ADP-ribose) polymerase or NAD:Arginine ADP ribosyltransferase in real time comprising an isolated polypeptide, or a fragment thereof, comprising an engineered site sufficient for the addition of at least one of the following moieties: phosphate ($PO_4$), ubiquitin, glycosyl or ADP-ribosyl moiety, wherein the polypeptide binds to at least one binding partner in at least one of the following manners: phosphorylation-, ubiq-uitination-, glycosylation- or ADP-ribosylation-dependent manner, and packaging materials therefore.

Preferably, the polypeptide further comprises a site that is adapted to carry a label or a tag.

It is preferred that addition of at least one of the following moieties: phosphate, ubiquitin, glycosyl or ADP-ribosyl moiety permits association of the polypeptide with the binding partner.

Alternatively, preferably, addition of at least one of the following moieties: phosphate, ubiquitin, glycosyl or ADP-ribosyl moiety prevents association of the polypeptide with the binding partner.

It is preferred that the isolated polypeptide comprises at least one contact site which binds to the binding partner, and the at least one contact site of the polypeptide comprises the site sufficient for the addition of at least one of the following moieties: phosphate, ubiquitin, glycosyl or ADP-ribosyl moiety.

It is additionally preferred that the polypeptide further comprises a detection means, the polypeptide comprising the detection means being a reporter molecule.

Preferably, the detection means comprises a light emitting detection means.

It is preferred that the light emitting detection means emits light of at least a fluorescent wavelength emission.

In another preferred embodiment, the light emitting detection means comprises a two different fluorophores.

Preferably, the fluorophores comprise fluorescein and tetramethylrhodamine or another suitable pair.

It is preferred that the polypeptide comprises a cysteine amino acid through which the light emitting means is attached via a covalent bond.

Preferably, the light emitting detection means comprises two different fluorescent proteins.

It is preferred that the two different fluorescent proteins comprise green fluorescent protein and red fluorescent protein.

It is additionally preferred that the two different fluorescent proteins comprise green fluorescent protein and blue fluorescent protein.

Preferably, the polypeptide comprises a coiled-coil containing a site sufficient for the addition of at least one of the following moieties: phosphate ($PO_4$), ubiquitin, glycosyl or ADP-ribosyl moiety.

In a preferred embodiment, the polypeptide associates via the coiled-coil with another coiled-coil containing polypeptide.

According to a different preferred embodiment, the polypeptide contains two coiled-coils and is therefore capable of self association via the two coiled-coils.

It is preferred that addition of at least one of the following moieties: phosphate, ubiquitin, glycosyl or ADP-ribosyl moiety permits association of the corresponding phosphate-, ubiquitin-, glycosyl- or ADP-ribosyl-containing polypeptide with another coiled-coil containing polypeptide to form a dimer.

Alternatively, it is preferred that addition of at least one of the following moieties: phosphate, ubiquitin, glycosyl or ADP-ribosyl moiety prevents association of the corresponding phosphate-, ubiquitin-, glycosyl- or ADP-ribosyl-containing polypeptide with another coiled-coil containing polypeptide to form a dimer.

Another aspect of the invention is a kit for determining the enzyme activity of a selected kinase, phosphatase, UDP-N-Acetylglucosamine-dolichyl-phosphate-N-acetylsglu-cosamine phosphotransferase, O-GlcNAc transferase, ubiquitin activating enzyme E1, ubiquitin conjugating enzyme E2, ubiquitin protein ligase E3, poly (ADP-ribose) polymerase or NAD:Arginine ADP ribosyltransferase in real time comprising an isolated polypeptide, or a fragment thereof, comprising an engineered site sufficient for the addition of at least one of the following moieties: phosphate ($PO_4$), ubiquitin, glycosyl or ADP-ribosyl moiety, wherein the polypeptide binds to at least one binding partner in at least one of the following manners: phosphorylation-, ubiquitination-, glycosylation- or ADP-ribosylation-dependent manner, and packaging materials therefore.

Preferably, the polypeptide further comprises a site that is adapted to carry a label or a tag.

It is preferred that addition of at least one of the following moieties: phosphate, ubiquitin, glycosyl or ADP-ribosyl moiety permits association of the polypeptide with the binding partner.

Preferably, addition of at least one of the following moieties: phosphate, ubiquitin, glycosyl or ADP-ribosyl moiety prevents association of the polypeptide with the binding partner.

It is preferred that the isolated polypeptide comprises at least one contact site which binds to said binding partner, and the at least one contact site of the polypeptide comprises the site sufficient for the addition of at least one of the following moieties: phosphate, ubiquitin, glycosyl or ADP-ribosyl moiety.

It is additionally preferred that the polypeptide further comprises a detection means, the polypeptide comprising the detection means being a reporter molecule.

Preferably, the detection means comprises a light emitting detection means.

It is preferred that the light emitting detection means emits light of at least a fluorescent wavelength emission.

In another preferred embodiment, the light emitting detection means comprises a two different fluorophores.

Preferably, the fluorophores comprise fluorescein and tetramethylrhodamine or another suitable pair.

It is preferred that the polypeptide comprises a cysteine amino acid through which the light emitting means is attached via a covalent bond.

Preferably, the light emitting detection means comprises two different fluorescent proteins.

It is preferred that the two different fluorescent proteins comprise green fluorescent protein and red fluorescent protein.

It is additionally preferred that the two different fluorescent proteins comprise green fluorescent protein and blue fluorescent protein.

Preferably, the polypeptide comprises a coiled-coil containing a site sufficient for the addition of at least one of the following moieties: phosphate ($PO_4$), ubiquitin, glycosyl or ADP-ribosyl moiety.

In a preferred embodiment, the polypeptide associates via the coiled-coil with another coiled-coil containing polypeptide.

According to a different preferred embodiment, the polypeptide contains two coiled-coils and is therefore capable of self association via the two coiled-coils.

It is preferred that addition of at least one of the following moieties: phosphate, ubiquitin, glycosyl or ADP-ribosyl moiety permits association of the corresponding phosphate-, ubiquitin-, glycosyl- or ADP-ribosyl-containing polypeptide with another coiled-coil containing polypeptide to form a dimer.

It is preferred that addition of at least one of the following moieties: phosphate, ubiquitin, glycosyl or ADP-ribosyl moiety prevents association of the corresponding phosphate-, ubiquitin-, glycosyl- or ADP-ribosyl-containing polypeptide with another coiled-coil containing polypeptide to form a dimer.

It is additionally preferred that the polypeptide assembles to form a coiled-coil structure and which has in its assembly region a site sufficient for at least one of the following: phosphorylation, ubiquitination, glycosylation or ADP-ribosylation.

The invention further encompasses use of the isolated polypeptide, or a fragment thereof, comprising an engineered site sufficient for the addition of at least one of the following moieties: phosphate ($PO_4$), ubiquitin, glycosyl or ADP-ribosyl moiety, wherein the polypeptide binds to at least one binding partner in at least one of the following manners: phosphorylation-, ubiquitination-, glycosylation- or ADP-ribosylation-dependent manner to monitor the addition of said phosphate, ubiquitin, glycosyl or ADP-ribosyl moiety to said polypeptide.

The invention provides a method to monitor the activity of an enzyme comprising the step of monitoring the addition of at least one of the following moieties: phosphate, ubiquitin, glycosyl or ADP-ribosyl moiety to at least one polypeptide, wherein the polypeptide is an isolated polypeptide, or a fragment thereof, comprising an engineered site sufficient for the addition of at least one of the following moieties: phosphate ($PO_4$), ubiquitin, glycosyl or ADP-ribosyl moiety, wherein the polypeptide binds to at least one binding partner in at least one of the following manners: phosphorylation-, ubiquitination-, glycosylation- or ADP-ribosylation-dependent manner and wherein the polypeptide further comprises a detection means, the polypeptide comprising the detection means being a reporter molecule.

Anther aspect of the invention is a method to monitor the activity of an enzyme comprising the step of monitoring the removal of at least one of a phosphate, ubiquitin, glycosyl or ADP-ribosyl moiety from at least one polypeptide, wherein the polypeptide is an isolated polypeptide, or a fragment thereof, comprising an engineered site sufficient for the addition of at least one of the following moieties: phosphate ($PO_4$), ubiquitin, glycosyl or ADP-ribosyl moiety, wherein the polypeptide binds to at least one binding partner in at least one of the following manners: phosphorylation-, ubiquitination-, glycosylation- or ADP-ribosylation-dependent manner and wherein the polypeptide further comprises a detection means, the polypeptide comprising the detection means being a reporter molecule.

Preferably, the methods further comprise, prior to the step of monitoring, the step of mixing in an appropriate buffer and an appropriate polypeptide concentration, the polypeptide and its binding partner labeled with an appropriate combination of fluorescence emitting means to monitor association between the polypeptide and its binding partner.

As used herein, the term "appropriate buffer" refers to a medium which permits activity of the protein-modifying enzyme used in an assay of the invention, and is typically a low-ionic-strength buffer or other biocompatible solution (e.g., water, containing one or more of physiological salt, such as simple saline, and/or a weak buffer, such as Tris or phosphate, or others as described hereinbelow), a cell culture medium, of which many are known in the art, or a whole or fractionated cell lysate. An "appropriate buffer" permits dimerization of non-phosphorylated and/or non-ubiquitinated and/or non-ADP-ribosylated and/or non-glycosylated engineered sites on isolated polypeptides of the invention and, preferably, inhibits degradation and maintains biological activity or the reaction components. Inhibitors of degradation, such as protease inhibitors (e.g., pepstatin, leupeptin, etc.) and nuclease inhibitors (e.g., DEPC) are well known in the art. Lastly, an appropriate buffer may comprise a stabilizing substance such as glycerol, sucrose or polyethylene glycol.

As used herein, the term "appropriate reporter molecule concentration" refers to an amount of labeled reporter molecule (that is, a labeled polypeptide of the invention) which emits a signal within the detection limits of a measuring device used in an assay of the invention. Such an amount is great enough to permit detection of a signal, yet small enough that a change in signal emission is detectable (e.g., such that a signal is below the upper limit of the device).

As used herein with regard to fluorescent labels, the term "appropriate combination" refers to a choice of reporter labels such that the emission wavelength spectrum of one (the "donor" moiety) is within the excitation wavelength spectrum of the other (the "acceptor" moiety).

It is preferred that the methods further comprise incubating the polypeptide and said binding partner with an appropriate modifying enzyme and measuring the change in energy transfer between the polypeptide and its binding partner.

Preferably, the measuring is performed by fluorescent resonance energy transfer (FRET).

It is preferred that the fluorescence emitting means comprise two different fluorophores, and particularly preferred that the fluorophores comprise fluorescein and tetramethylrhodamine or another suitable pair.

Preferably, the polypeptide comprises a cysteine amino acid through which the fluorescence emitting means is attached via a covalent bond.

In another preferred embodiment, the light emitting means comprises two different fluorescent proteins.

It is preferred that the two different fluorescent proteins comprise green fluorescent protein and red fluorescent protein.

It is additionally preferred that the two different fluorescent proteins comprise green fluorescent protein and blue fluorescent protein.

Preferably, the method further comprises exciting the reporter molecules and monitoring fluorescence emission.

It is preferred that the modifying enzyme is selected from the group that includes a kinase, a phosphatase, a UDP-N-Acetylglucosamine-Dolichyl-phosphate-N-acetylsglucosamine phosphotransferase, an O-GlcNAc transferase, a ubiquitin activating enzyme E1, a ubiquitin conjugating enzyme E2, a ubiquitin protein ligase E3, poly (ADP-ribose) polymerase and an NAD:Arginine ADP ribosyltransferase.

In a preferred embodiment, the method further comprises the addition to the buffer of an agent which modulates the activity of the modifying enzyme.

As used herein with regard to a biological or chemical agent, the term "modulate" refers to enhancing or inhibiting the activity of a protein-modifying enzyme in an assay of the invention; such modulation may be direct (e.g. including, but not limited to, cleavage of- or competitive binding of another substance to the enzyme) or indirect (e.g. by blocking the initial production or, if required, activation of the modifying enzyme).

"Modulation" refers to the capacity to either increase or decease a measurable functional property of biological activity or process (e.g., enzyme activity or receptor binding) by at least 10%, 15%, 20%, 25%, 50%, 100% or more; such increase or decrease may be contingent on the occurrence of a specific event, such as activation of a signal transduction pathway, and/or may be manifest only in particular cell types.

The term "modulator" refers to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activities (or activity) of a modulator may be known, unknown or partially-known. Such modulators can be screened using the methods described herein.

The term "candidate modulator" refers to a compound to be tested by one or more screening method(s) of the invention as a putative modulator. Usually, various predetermined concentrations are used for screening such as 0.01 µM, 0.1 µM, 1.0 µM, and 10.0 µM, as described more fully hereinbelow. Test compound controls can include the measurement of a signal in the absence of the test compound or comparison to a compound known to modulate the target.

Preferably, the method further comprises the addition to the buffer of an agent which modulates fluorescence emission of the reporter molecules.

Another aspect of the invention is a kit comprising a fluorophore-labeled polypeptide, wherein the polypeptide is an isolated polypeptide, or a fragment thereof, comprising an engineered site sufficient for the addition of at least one of the following moieties: phosphate ($PO_4$), ubiquitin, glycosyl or ADP-ribosyl moiety, wherein the polypeptide binds to at least one binding partner in at least one of the following manners: phosphorylation-, ubiquitination-, glycosylation- or ADP-ribosylation-dependent manner, an enzyme selected from the group that includes a kinase, a phosphatase, a UDP-N-Acetylglucosamine-Dolichyl-phosphate-N-acetylsglucosamine phosphotransferase, an O-GlcNAc transferase, a ubiquitin activating enzyme E1, a ubiquitin conjugating enzyme E2, a ubiquitin protein ligase E3, a poly (ADP-ribose) polymerase, an NAD:Arginine ADP ribosyltransferase and packaging therefor.

It is preferred that the kit further comprises a reaction buffer for the enzyme.

It is additionally preferred that the kit further comprises a substrate for the enzyme.

Preferably, the substrate is selected from the group that includes MgATP, cAMP, ubiquitin, nicotinamide adenine dinucleotide ($NAD^+$), uridine-diphosphate-N-acetylglucosamine-dolichyl-phosphate (UDP-N-acetylglucosamine-dolichyl-phosphate) and UDP-N-acetylglucosamine.

It is contemplated that at least a part of a substrate of an enzyme of use in an assay of the invention is transferred to an engineered site on an isolated polypeptide of the invention. As used herein, the term "at least a part of a substrate" refers to a portion (e.g., a fragment of an amino acid sequence, a moiety or a group, as defined above) which comprises less than the whole of the substrate for the enzyme, the transfer of which portion to an engineered site on an isolated polypeptide, both as defined above, is catalyzed by the enzyme.

It is preferred that the kit further comprises a cofactor for the enzyme.

The invention also encompasses an isolated pair of polypeptides which associate to form a dimer in at least one of the following manners: phosphorylation-, ubiquitination-, glycosylation- or ADP-ribosylation-dependent manner, the pair comprising a first polypeptide comprising at least one binding domain, at least one engineered phosphorylation, ubiquitination, glycosylation or ADP-ribosylation site, and a detection means whereby the addition/removal of phosphate, ubiquitin, glycosyl or ADP-ribosyl moiety to the corresponding phosphorylation, ubiquitination, glycosylation or ADP-ribosylation site is detectable via binding of the binding domain with a binding partner; and a second polypeptide which is a binding partner of the first polypeptide, wherein dimer formation is detectable via the detection means.

Preferably, the detection means comprises a light emitting detection means.

It is preferred that the light emitting detection means emits light of at least a fluorescent wavelength emission.

It is additionally preferred that the light emitting detection means comprises a first fluorophore on the first polypeptide and a second fluorophore different from the first fluorophore on the second polypeptide, the first and second fluorophores together being operative to promote fluorescent energy transfer.

Preferably, the first and second fluorophores comprise one of fluorescein or tetramethylrhodamine or another suitable pair.

It is preferred that the fluorophores comprise fluorescein and tetramethylrhodamine or another suitable pair.

In a particularly preferred embodiment, the first polypeptide comprises a cysteine amino acid through which the light emitting means is attached via a covalent bond.

It is preferred that the light emitting detection means comprises two different fluorescent proteins, and highly preferred that the two different fluorescent proteins comprise green fluorescent protein and red fluorescent protein.

It is additionally preferred that the two different fluorescent proteins comprise green fluorescent protein and blue fluorescent protein.

The invention additionally provides a method of screening for a candidate modulator of enzymatic activity of a phosphatase, kinase, UDP-N-Acetylglucosamine-Dolichyl-phosphate-N-acetylsglucosamine phosphotransferase, O-GlcNAc transferase, ubiquitin activating enzyme E1, ubiquitin conjugating enzyme E2, ubiquitin protein ligase E3, poly (ADP-ribose) polymerase or NAD:Arginine ADP ribosyltransferase, the method comprising mixing in an appropriate buffer an appropriate amount of a polypeptide, wherein the polypeptide is an isolated polypeptide, or a fragment thereof, comprising an engineered site sufficient for the addition of at least one of the following moieties: phosphate ($PO_4$), ubiquitin, glycosyl or ADP-ribosyl moiety, wherein the polypeptide binds to at least one binding partner in at least one of the following manners: phosphorylation-, ubiquitination-, glycosylation- or ADP-ribosylation-dependent manner, and, wherein each of the polypeptide and said binding partner is suitably labelled with detection means for monitoring association/disassociation between same; and a sample of material whose enzymatic activity is to be tested; and monitoring the addition or removal of at least one of the following: a phosphate, ubiquitin, glycosyl or ADP-ribosyl group to the polypeptide, wherein the addition or removal of said phosphate, ubiquitin, glycosyl or ADP-ribosyl group is indicative of modulation by the candidate modulator of the enzymatic activity.

As used herein, the term "sample" refers to a collection of inorganic, organic or biochemical molecules which is either found in nature (e.g., in a biological- or other specimen) or in an artificially-constructed grouping, such as agents which might be found and/or mixed in a laboratory. Such a sample may be either heterogeneous or homogeneous.

As used herein, the interchangeable terms "biological specimen" and "biological sample" refer to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "Biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as proteins or nucleic acid molecules.

As used herein, the term "organism" refers to all cellular life-forms, such as prokaryotes and eukaryotes, as well as non-cellular, nucleic acid-containing entities, such as bacteriophage and viruses.

It is preferred that the detection means comprises a light emitting detection means and highly preferred that the light emitting detection means emits light of at least a fluorescent wavelength emission.

Preferably, the light emitting detection means comprises two different fluorophores.

It is preferred that the fluorophores comprise fluorescein and tetramethylrhodamine or another suitable pair.

In a particularly preferred embodiment, the polypeptide comprises a cysteine amino acid through which the light emitting detection means is attached via a covalent bond.

It is preferred that the light emitting detection means comprises two different fluorescent proteins and highly preferred that the two different fluorescent proteins comprise green fluorescent protein and red fluorescent protein.

It is additionally preferred that the two different fluorescent proteins comprise green fluorescent protein and blue fluorescent protein.

Preferably, the monitoring comprises measuring the change in energy transfer between the polypeptide and its binding partner.

It is preferred that the measuring is performed by fluorescent resonance energy transfer (FRET).

The invention additionally provides a method of screening for a candidate modulator of enzymatic activity of a phosphatase, kinase, UDP-N-Acetylglucosamine-Dolichyl-phosphate-N-acetylsglucosamine phosphotransferase, O-GlcNAc transferase, ubiquitin activating enzyme E1, ubiquitin conjugating enzyme E2, ubiquitin protein ligase E3, poly (ADP-ribose) polymerase or NAD:Arginine ADP ribosyltransferase, the method comprising mixing in an appropriate buffer an appropriate amount of an isolated pair of polypeptides which associate to form a dimer in at least one of the following manners: phosphorylation-, ubiquitination-, glycosylation- or ADP-ribosylation-dependent manner, the pair comprising a first polypeptide comprising at least one binding domain, at least one engineered phosphorylation, ubiquitination, glycosylation or ADP-ribosylation site, and a detection means whereby the addition/removal of at least one of the following groups: phosphate, ubiquitin, glycosyl or ADP-ribosyl group to the corresponding phosphorylation, ubiquitination, glycosylation or ADP-ribosylation site is detectable via binding of said binding domain with a binding partner; and a second polypeptide which is a binding partner of the first polypeptide, wherein dimer formation is detectable via the detection means, wherein each member of the pair of polypeptides is suitably labeled with detection means for monitoring association/disassociation between same; and a sample of material whose enzymatic activity is to be tested; and monitoring the addition or removal of at least one of the following groups: phosphate, ubiquitin, glycosyl or ADP-ribosyl group to the pair of polypeptides, wherein the addition or removal of said phosphate, ubiquitin, glycosyl or ADP-ribosyl group is indicative of modulation by the candidate modulator of the enzymatic activity.

It is preferred that the detection means comprises a light emitting detection means, and particularly preferred that the light emitting detection means emits light of at least a fluorescent wavelength emission.

Preferably, the light emitting detection means comprises a two different fluorophores.

In a preferred embodiment, the fluorophores comprise fluorescein and tetramethylrhodamine or another suitable pair.

It is particularly preferred that a polypeptide of the pair of polypeptides comprises a cysteine amino acid through which the light emitting detection means is attached via a covalent bond.

Preferably, the light emitting detection means comprises two different fluorescent proteins.

It is preferred that the two different fluorescent proteins comprise green fluorescent protein and red fluorescent protein.

It is additionally preferred that the two different fluorescent proteins comprise green fluorescent protein and blue fluorescent protein.

In another preferred embodiment, the monitoring comprises measuring the change in energy transfer between a first polypeptide of the pair of polypeptides and a second polypeptide of the pair of polypeptides.

Preferably, the measuring is performed by fluorescent resonance energy transfer (FRET).

It is highly preferred that a method of the methods described above comprises real-time observation of association of an isolated polypeptide and its binding partner or of an isolated pair of polypeptides.

As used herein in reference to monitoring, measurements or observations in assays of the invention, the term "real-time" refers to that which is performed contemporaneously with the monitored, measured or observed events and which yields a result of the monitoring, measurement or observation to one who performs it simultaneously, or effectively so, with the occurrence of a monitored, measured or observed event. Thus, a "real time" assay or measurement contains not only the measured and quantitated result, such as fluorescence, but expresses this in real time, that is, in hours, minutes, seconds, milliseconds, nanoseconds, picoseconds, etc. Shorter times exceed the instrumentation capability; further, resolution is also limited by the folding and binding kinetics of polypeptides.

Further features and advantages of the invention will become more fully apparent in the following description of the embodiments and drawings thereof, and from the claims.

BRIEF DESCRIPTIONS OF THE DRAWINGS

FIG. 1 diagrams the structure of single and dimerized coiled-coil peptide motifs.

FIG. 2 presents a schematic overview of FRET in an assay of the invention.

FIG. 3 presents monomer:excimer fluorescence.

FIG. 4 presents the circular dichroism (CD) spectra of Zip3 and Zip3P at 20° C. Ellipticity in mdeg is shown on the y-axis, while wavelength in nm is shown on the x-axis. Closed diamonds, Zip3; closed squares, Zip4.

Figure 8:
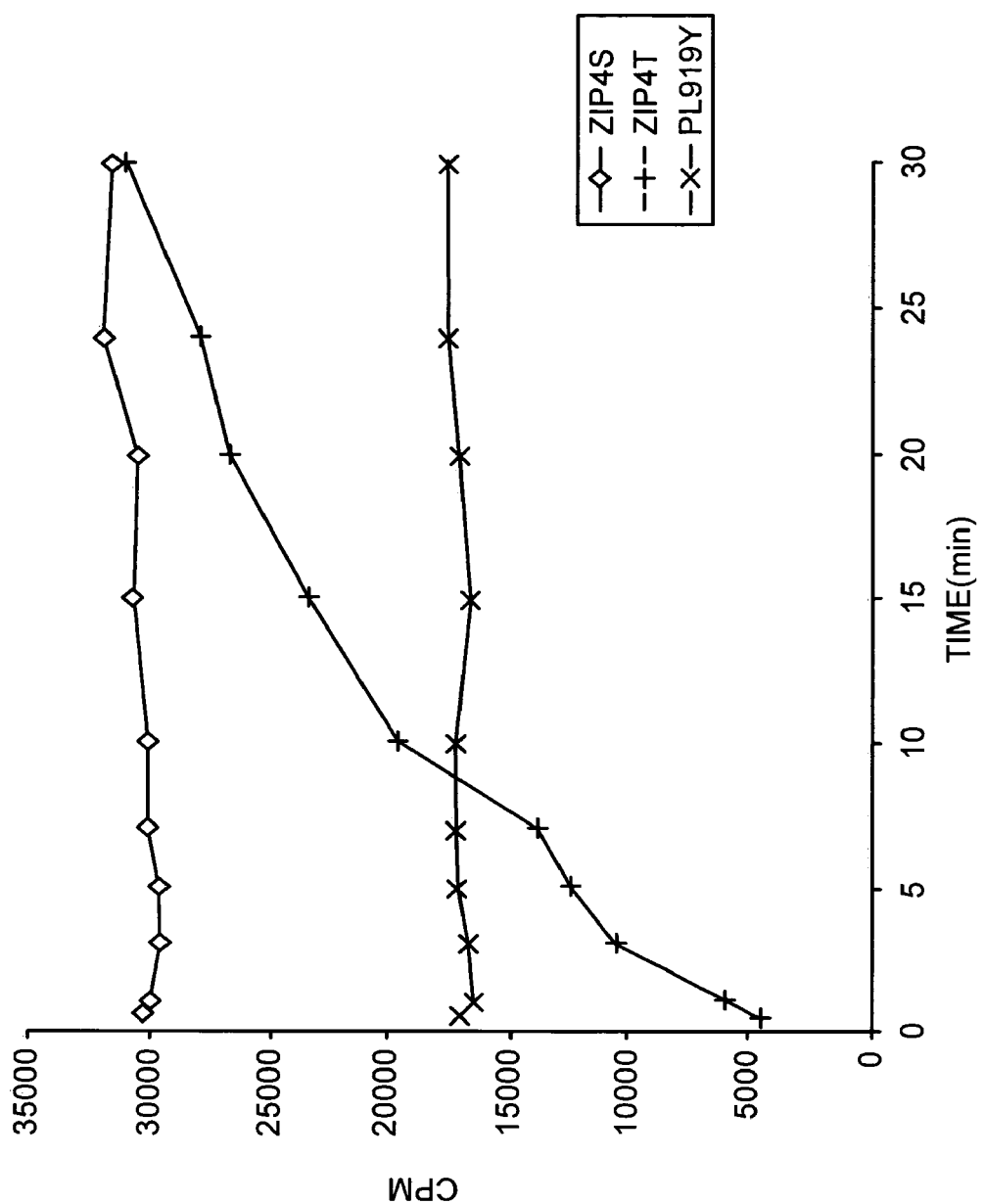

FIG. 8 presents the phosphorylation of Zip4S and Zip4T by PKA (diamonds, Zip4S; +'s, Zip4T; x's, PL919Y). Counts per minute are indicated on the y-axis; time in minutes is shown on the x-axis.

Figure 9:
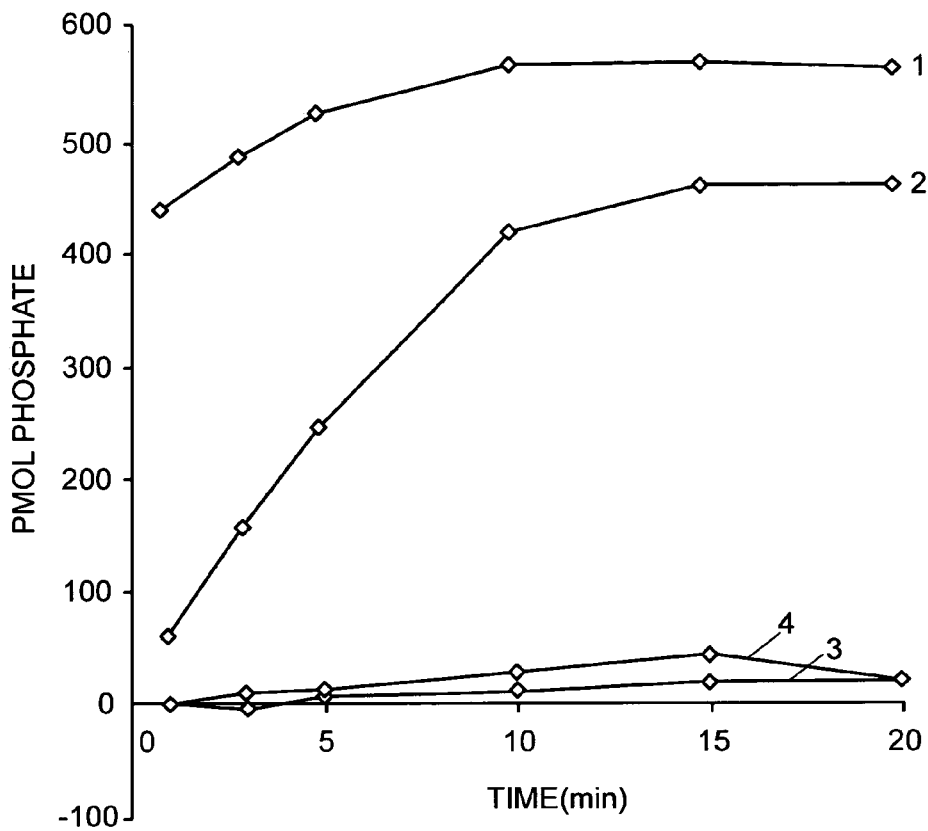

FIG. 9 shows data demonstrating the specificity of Zip4S phosphorylation. 1: Autocamtide II phosphorylated by CaMKII in the presence of $Ca^{2+}$ and calmodulin. 2: Zip4S phosphorylated by PKA. 3: Zip4S phosphorylated by CaMKII in the presence of Calmodulin and $Ca^{2+}$. 4: Autocamtide II phosphorylated by CaMKII in the presence of CaM, but absence of $Ca^{2+}$.

Figure 10:
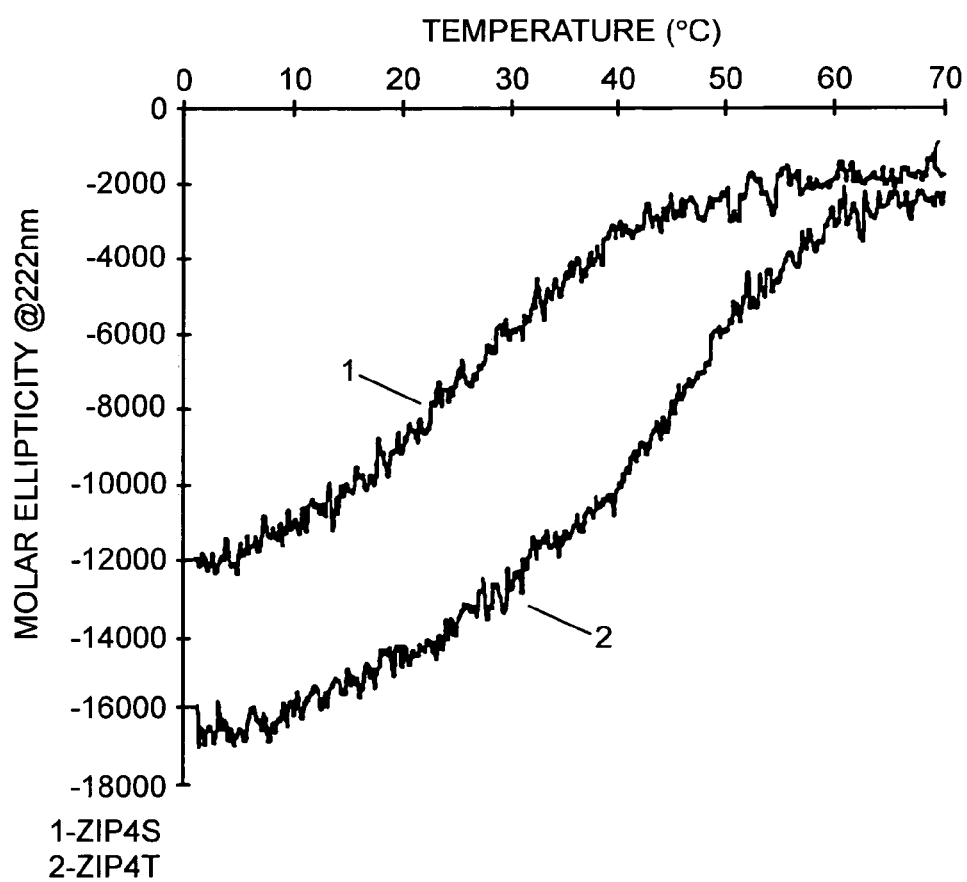

FIG. 10 shows thermal denaturation of Zip4S and Zip4T. Molar ellipticity is at 222 nm is indicated on the y-axis; temperature in ° C. is indicated on the x-axis.

Figure 11:
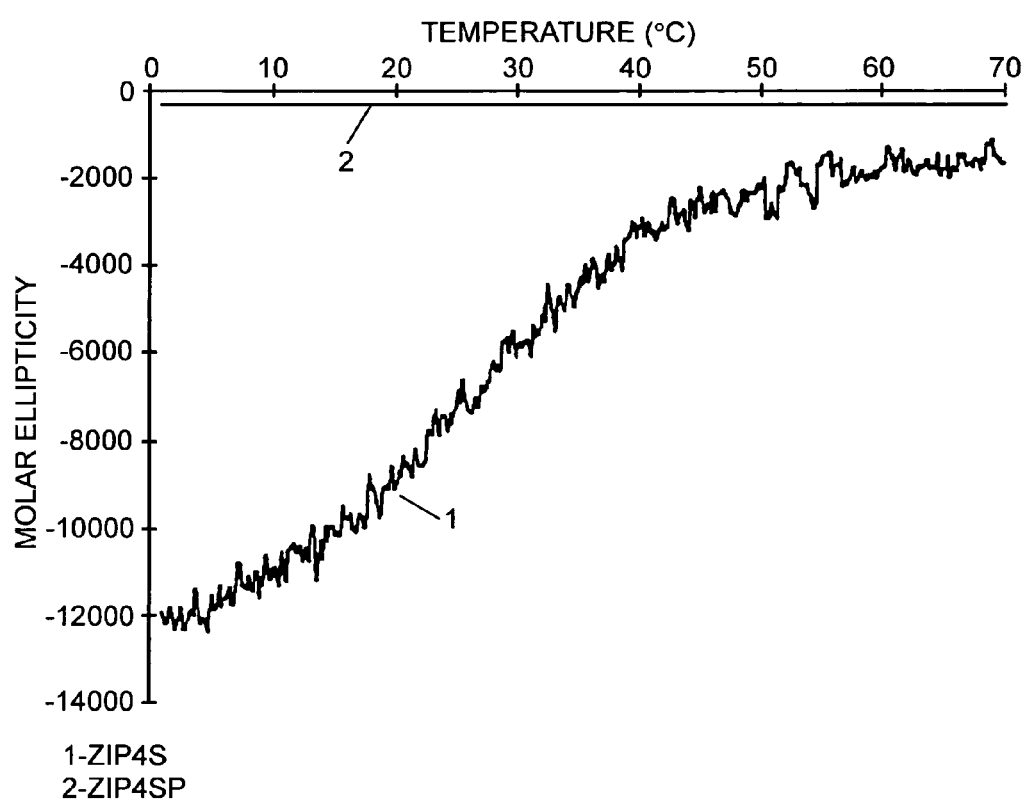

FIG. 11 presents thermal denaturation of Zip4S and Zip4SP. Molar ellipticity is indicated on the y-axis and temperature in ° C. on the x-axis.

Figure 12:
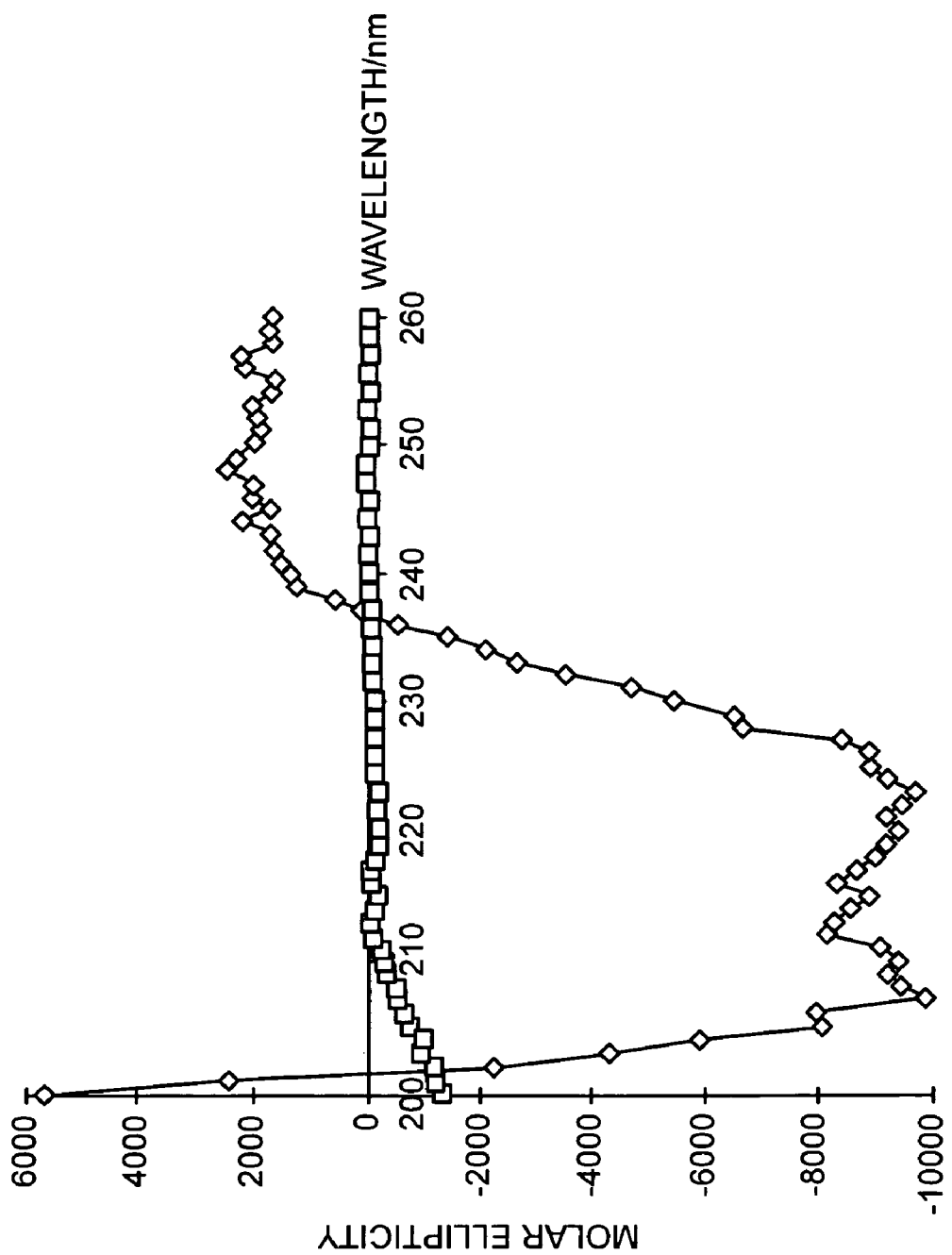

FIG. 12 presents CD spectra of Zip4S and Zip4SP at 1° C. Molar ellipticity is charted on the y-axis and wavelength in nm is shown on the x-axis (closed diamonds, Zip4S; closed squares, Zip4SP).

Figure 13:
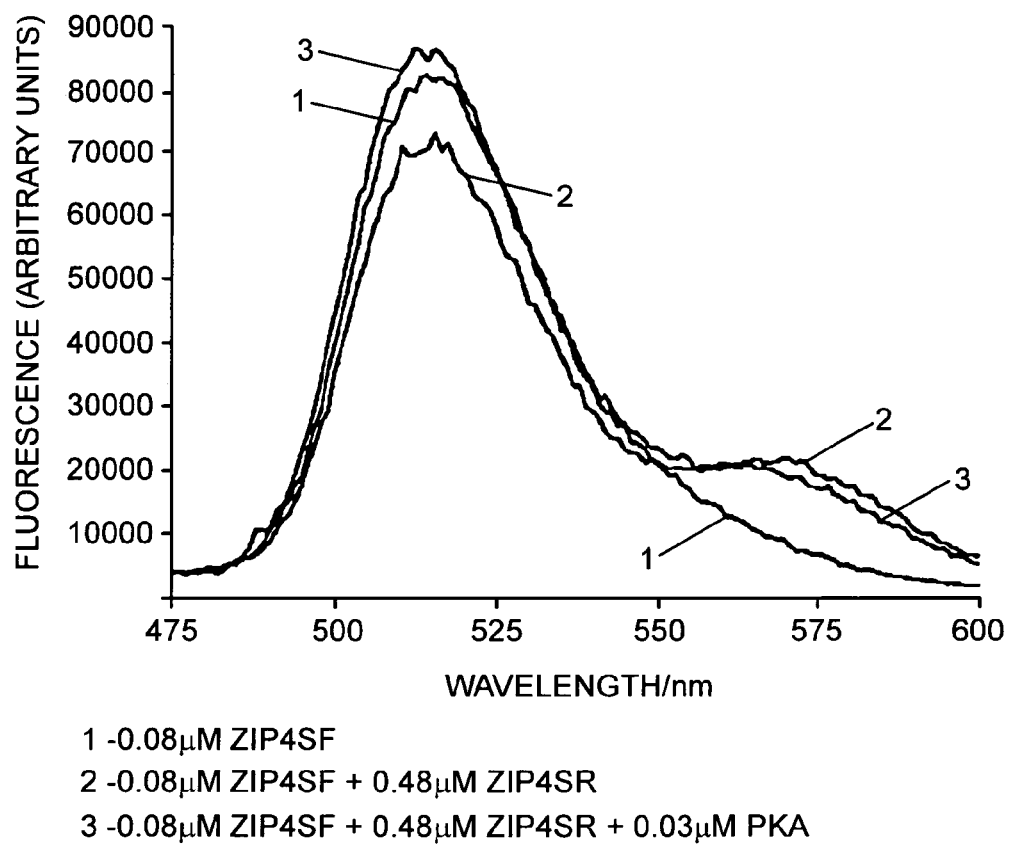

FIG. 13 presents FRET between Zip4SF and Zip4SR, reversed by phosphorylation of the polypeptide reporter group (fluorescence on y-axis; emission λ on x-axis.

Figure 14:
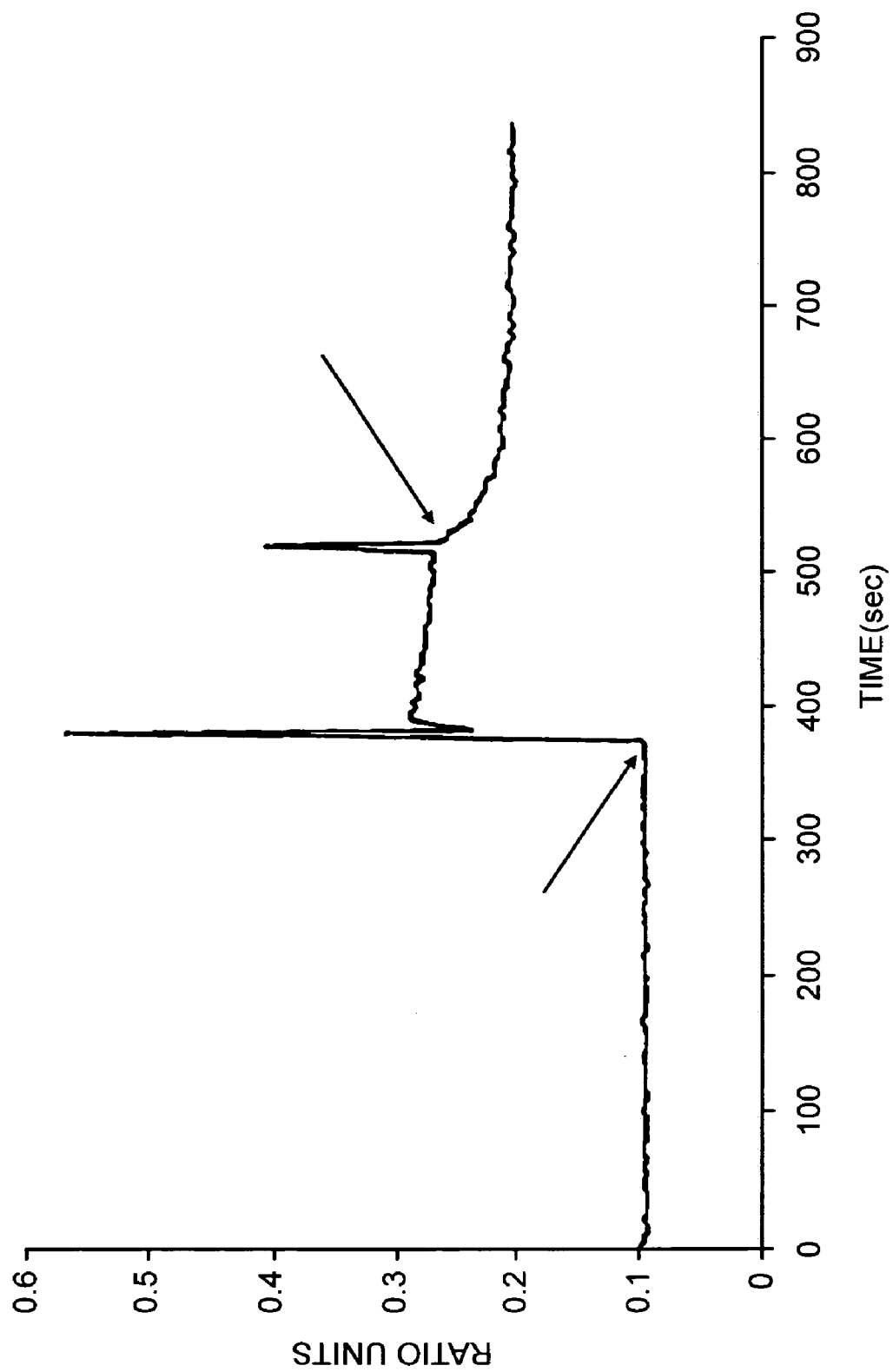

FIG. 14 presents FRET between Zip4SF and Zip4SR, lost upon phosphorylation of polypeptides by PKA. Time course of phosphorylation measured in real time. Fluorescence at 516 nm on y-axis (excitation λ, 450 nm), time in seconds on x-axis. Arrow (filled head): addition of Zip4SR. Arrow (open head): addition of PKA to Zip4SF.

Figure 15:
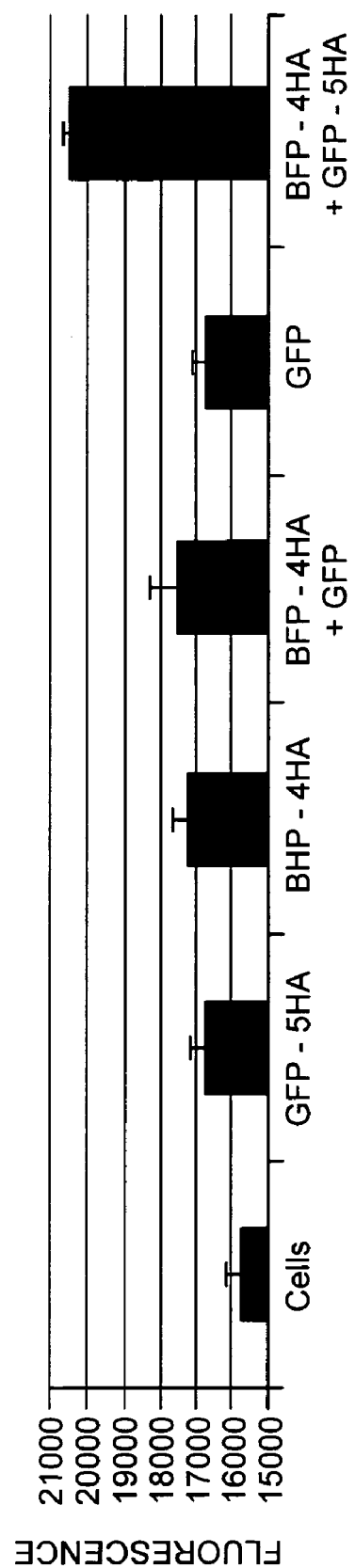

FIG. 15 is a bar graph presenting the results of an in vivo FRET assay.

Figure 16:
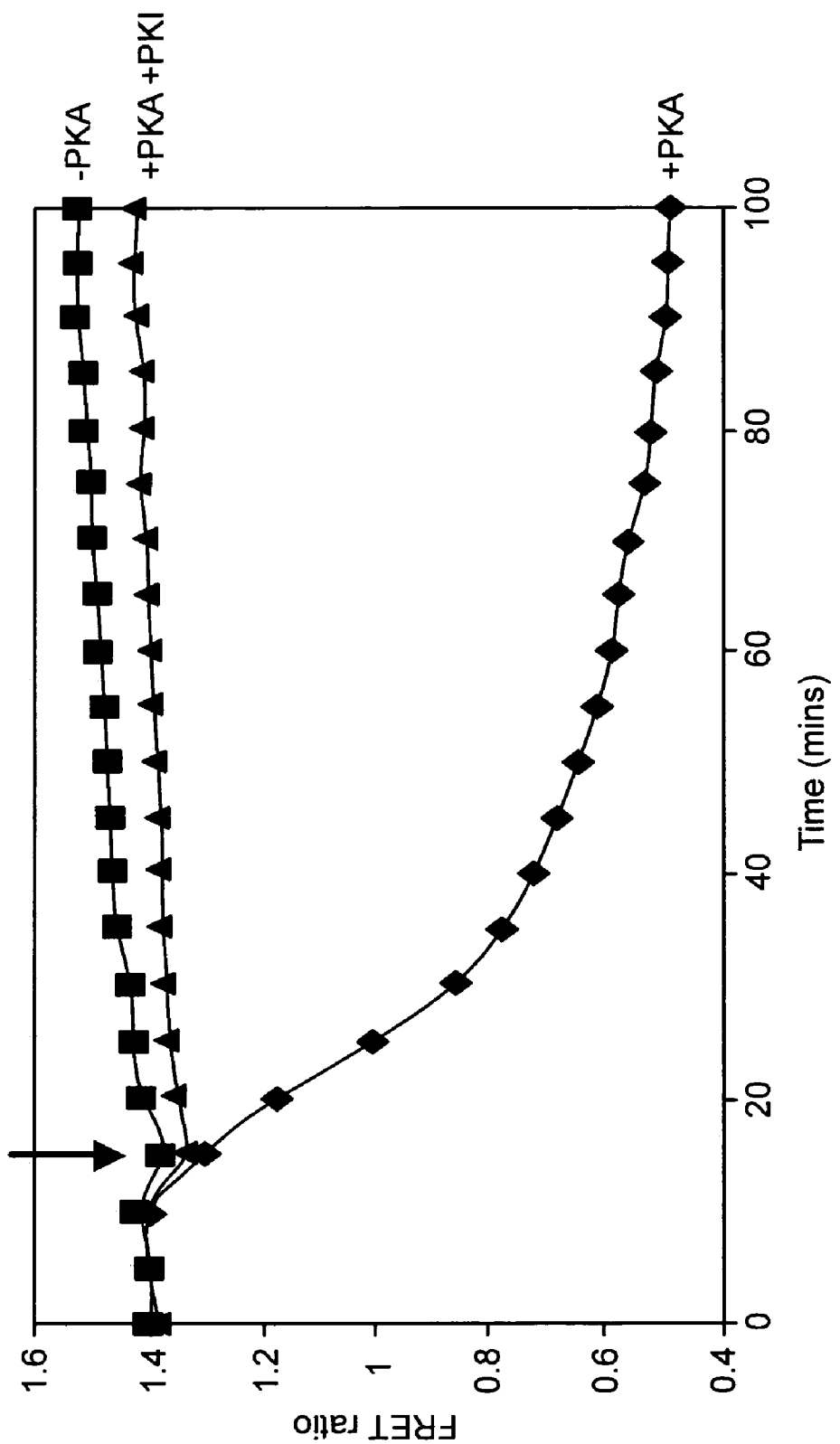

FIG. 16 is a graph demonstrating the results of a PKA assay.

DESCRIPTION

The invention is based upon the discovery that a polypeptide comprising a coiled-coil associates with a binding partner to form oligomers or dissociates from a binding partner in a manner that is dependent upon the presence or absence of a "moiety", as described herein, and that is detectable and measurable in a highly sensitive manner that may be in real time.

Coiled-Coils

The coiled-coil domain is structurally conserved among many proteins that interact to form homo- or heterodimeric oligomers. The leucine zipper provides an example of one such protein structural motif. It is found in, among other examples, a nuclear protein that functions as a transcriptional activator of a family of genes involved in the General Control of Nitrogen (GCN4) metabolism in S. cerevisiae. The protein is able to dimerize and bind promoter sequences containing the recognition sequence for GCN4, thereby activating transcription in times of nitrogen deprivation.

Coiled-coils are α-helical oligomers or bundles with between 1 and 5 polypeptide strands with the following characteristics: (i) a sequence hallmark of a predominance of hydrophobic residues (in particular alanine, isoleucine, leucine, methionine or valine) spaced 3 and 4 residues apart in the primary sequence which is repeated three or more times in near or exact succession (canonical heptad coiled-coil repeat, abbreviated to $(3,4)_n$ where n=3 or greater). The hydrophobic residues are present at the 'a' and 'd' positions within a heptad when the amino acids are identified as positions a, b, c, d, e, f and g by order of sequence. In addition, spacing of hydrophobic residues in patterns of 3,4,4 and 3,4,3 (hendecad repeat) have recently been reported (Hicks et al., 1997, *Folding and Design*, 2: 149–158) and are compatible with the coiled-coil structure. (ii) In structural terms coiled-coil helical bundles have between 2 and 5 helices which are offset at roughly 20° to adjacent strands with the hydrophobic sidechains interdigitating in the interface between helices in what is termed the "knobs into holes" packing (Crick, 1953, *Acta. Crystallogr.*, 6: 689–697). Natural and non-natural coiled-coils can have parallel and/or antiparallel helices. Both homotypic (multiple strands of identical sequence) and heterotypic bundles have been described.

Figure 1A:
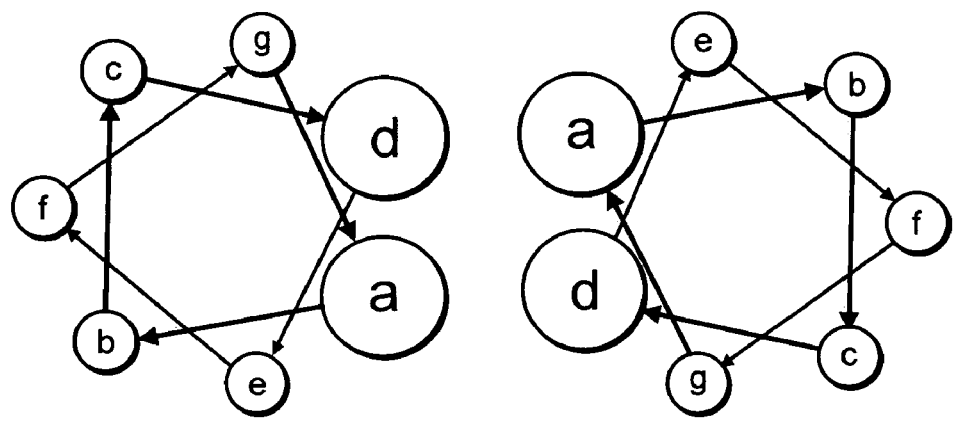
Figure 1B:
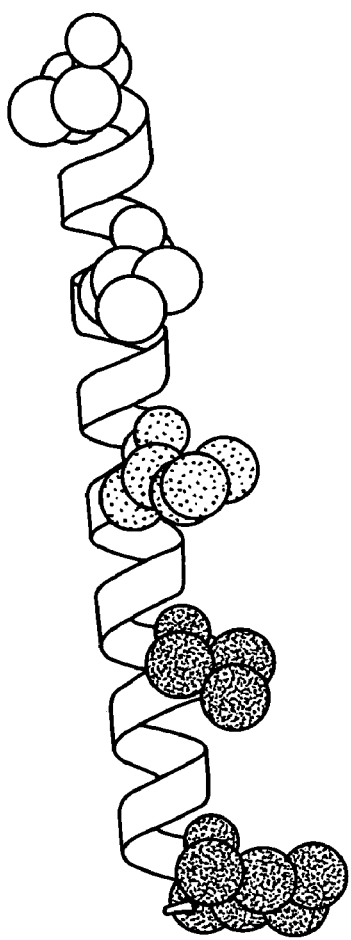
Figure 1C:
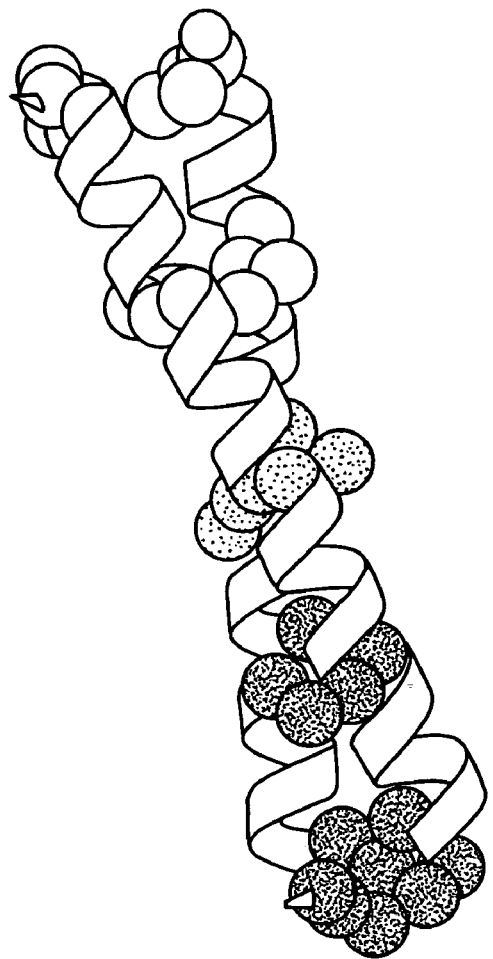

Leucine zipper sequences conform to the coiled-coil rules above and typically have leucine residues at the 'd' position of the canonical heptad repeat (FIG. 1A). As shown in FIG. 1B, these leucine residues represent a single face of the helix. Interdigitating with these leucine residues are valine residues. The combination of these residues forms a continuous hydrophobic face which associates with an equivalent region in an associating subunit (FIG. 1C). Alternatively the hydrophobic face can be discontinuous due to interruptions in the heptad repeat sequence. This, however, does not interfere with the ability of these coiled-coils to interact. The stability of the dimer thus formed is conferred by the hydrophobic interactions between the leucine and valine residues and hydrogen bonds that form between residues present on the two interacting helices. Interestingly, the coiled-coil domain of GCN4 has been shown to dimerize as an isolated peptide (Gonzalez et al., 1996, *Nature Structural Biology*, 3: 1011–1018).

Examples of naturally-occurring coiled-coils are as follows:
Coiled-coil class and example:
  fgabcdefgabcdefgabcdefgabcdefgabcdefgabcdeg (SEQ ID NO.1)
  Parallel two-stranded
  tropomyosin
  TMPA_RABIT, 10–279 (270)
  (J.BIOL.CHEM. 253, 1137–1148, 1978)
  dystropphin
  ILISLESEERGELERILADLEEENRN-LQAEYDRLKQQHEHK (SEQ ID NO.2)
  SWISS PROT:P11532 (HUMAN)
  (*Trends Biol. Sci.*, 20,133–135, 1995)
  GCN4*
  MKQLEDKVEELLSKNYHLENEVARLKKLVGER (SEQ ID NO.3)
  GCN4_YEAST, 250–281 (32)
  (*Proc. Natl. Acad. Sci. U.S.A.*, 81, 6442–6446, 1982)
  cFOS*
  TDTLQAETDQLEDEKSALQTEIAN-LLKEKEKLEFILAAH (SEQ ID NO.4)
  FOS_HUMAN, 162–199 (39)
  (*Proc. Natl. Acad. Sci, U.S.A.*, 80: 3183–3187, 198)
  cJUN*
  IARLEEKVKTLKAQNSELASTANML-REQVAQLKQKVMNH (SEQ ID NO.5)
  AP1_HUMAN, 277–315 (39)
  (*Proc. Natl. Acad. Sci. U.S.A.*, 85: 9148–9152, 1988
  antiparallel two-stranded
  Seryl-tRNA synthetase, *E.coli*
  VDKLGALEERRKVLQVKTENLQAERNSR-SKSIGQAKAR (SEQ ID NO.6)
  SYS_ECOLI, 27–64 (38)
  EPLRLEVNKLGEELDAAKAELDALQAEIRDIA (SEQ ID NO.7)
  *NUCLEIC ACIDS RES.*, 15, 1005–1017,1987
  SYS ECOLI, 69–100 (32)
  Seryl-tRNA synthetase,
  DLEALLALDREVQELKKRLQEVQTERNQVAKRV (SEQ ID NO.8)
  Thermus thermophilus*
  EALIARGKALGEEAKRLEEALREKEARLEALL (SEQ ID NO.9)
  SYS_THERM, 26–58 (33)
  (*Science*, 263: 1404–141)
  SYS_THERM, 67–98 (32)
  Transcript cleavage factor GreA*
  LRGAEKLREELDFLKSvFRPEIIAAIAEAR (SEQ ID NO.10)
  GREA_ECOLI, 8–37 (30) AEYHAAREQQGFCE-GRIKDIEAKLSN (SEQ II) NO.11)
  *Nature*, 373: 636–640, 1995)
  GREA_ECOLI, 46–71 (26)
  Parallel three-stranded
  GCN4 Zip mutant pll* MKQIEDKIEEILSKIYHIENE-IARIKKLIGER (SEQ ID NO.12)
  GCN4 Zip mutant pll*
  (*Nature*, 371: 80–83)
  Antiparallel three-stranded
  synthetic peptide coil-Ser* EWEALEKK-LAALESKLQALEKKLEALEHG (SEQ ID NO.13)
  (*Science*, 259: 1288–1293)
  Parallel four-stranded
  GCN4 Zip mutant pL1*
  MKQIEDKLEEILSKLYHIENELARIKKLLGER (SEQ ID NO.14)
  (*Nature*, 371: 80–83)
  Antiparallel four-stranded
  Repressor of primer ROP* QEKTALNMARFIR-SQTLTLLEKLNE (SEQ ID NO.15)
  ROP_ECOLI, 4–28 (25) DEQADICESLHDHADELYR-SCLAR (SEQ ID NO.16)
  (*Proc. Natl. Acad. Sci. U.S.A.*, 79: 6313–6317 1982)
  ROP_ECOLI, 32–55 (24)
  Parallel five-stranded
  phospholamban LILICLLLICIIVMLL (SEQ ID NO.17)
  PPLA_HUMAN, 37–52 (16)
  (JBC 271, 5941–5946, 1996)

Dimerization of coiled-coils is not disrupted by modifications occurring at specific amino acids; however, as disclosed herein, phosphorylation of the "a" amino acid of the central heptad repeat is not tolerated, in that it destabilizes the coiled-coil structure. The present invention contemplates the use of polypeptides comprising coiled-coils in order to assay the activity of a protein modifying enzyme which influences the state of post-translational protein modification.

General guidelines (assuming, in this instance, a 4.5-heptad coiled-coil structure) for placement of a protein modification site within a polypeptide comprising a coiled-coil for use in an assay of the invention are as follows:

1. It is preferable to insert a protein modification site into the interface between coiled-coil strands (i.e., positions a, d, e or g of the canonical heptad repeat structure or corresponding positions in non-canonical coiled-coil structures; Hicks et al., 1997, *Folding & Design*, 2: 149–158).

2. Modification at the 'a' site is preferable to that which occurs at the 'd' site, as the 'a site tolerates the presence of a polar amino acid better than does the 'd' site (Woolfson and Alber, 1995, *Protein Sci.*, 4: 1596–1607).

3. Positions 'a' and 'd' of the heptad repeat usually contain residues V, I, L, M, or A (canonical residues); however certain other residues can be tolerated at these positions and often modulate oligomeric assembly. The stability of the coiled-coil oligomer reduces with each substitution of a non-canonical residue at positions 'a' or 'd', measured as a reduction in Tm (mid-point of the thermal unfolding transition of approximately 40° C. per non-canonical residue at the 'a' or 'd' position in the GCN4 sequence background (Harbury, P. B., Zhang, T., Kim, P. S., and Alter, T., (1993) *Science* 262, 1401–1407).

4. It is preferable to insert the polar residue for modification within the central 3 heptads of the 4.5-heptad coiled-coil structure for maximum impact on the stability of the oligomer upon modification of the polar residue.

5. The covalent linkage of two coiled-coil strands increases the stability of the interaction between strands considerably. This can be used to facilitate the incorporation of more extreme changes from the canonical sequence pattern, and/or to reduce the number of repeating structures (heptad or other non-canonical repeats) needed for a stable interface.

6. Modification elsewhere in the coiled-coil (away from the hydrophobic interface) might affect the kinetics of folding of secondary structure and thereby inhibit coiled-coil oligomer formation. This will be chemical-moiety-dependent, having the greatest effect if the moiety in question is large and highly solvated.

Methods by which assays of the invention are performed are described in detail in the following sections and in the Examples.

Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., *Molecular Cloning: A Laboratory Manual*, 2d ed. (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described herein are those well known and commonly employed in the art. Standard techniques are used for chemical syntheses, chemical analyses, pharmaceutical formulation and delivery, and treatment of patients. As employed throughout the disclosure, terms, unless otherwise indicated, shall be understood to have commonly understood meanings.

Fluorescence Energy Resonance Transfer (FRET)

A tool with which to assess the distance between one molecule and another (whether protein or nucleic acid) or between two positions on the same molecule is provided by the technique of fluorescence resonance energy transfer (FRET), which is now widely known in the art (for a review, see Matyus, 1992, *J. Photochem. Photobiol. B: Biol.*, 12: 323–337, which is herein incorporated by reference). FRET is a radiationless process in which energy is transferred from an excited donor molecule to an acceptor molecule; the efficiency of this transfer is dependent upon the distance between the donor an acceptor molecules, as described below. Since the rate of energy transfer is inversely proportional to the sixth power of the distance between the donor and acceptor, the energy transfer efficiency is extremely sensitive to distance changes. Energy transfer is said to occur with detectable efficiency in the 1–10 nm distance range, but is typically 4–6 nm for favorable pairs of donor and acceptor.

Radiationless energy transfer is based on the biophysical properties of fluorophores. These principles are reviewed elsewhere (Lakowicz, 1983, *Principles of Fluorescence Spectroscopy*, Plenum Press, New York; Jovin and Jovin, 1989, *Cell Structure and Function by Microspectrofluorometry*, eds. E. Kohen and J. G. Hirschberg, Academic Press, both of which are incorporated herein by reference). Briefly, a fluorophore absorbs light energy at a characteristic wavelength. This wavelength is also known as the excitation wavelength. The energy absorbed by a flurochrome is subsequently released through various pathways, one being emission of photons to produce fluorescence. The wavelength of light being emitted is known as the emission wavelength and is an inherent characteristic of a particular fluorophore. Radiationless energy transfer is the quantum-mechanical process by which the energy of the excited state of one fluorophore is transferred without actual photon emission to a second fluorophore. That energy may then be subsequently released at the emission wavelength of the second fluorophore. The first fluorophore is generally termed the donor (D) and has an excited state of higher energy than that of the second fluorophore, termed the acceptor (A). The essential features of the process are that the emission specturm of the donor overlap with the excitation spectrum of the acceptor, and that the donor and acceptor be sufficiently close. The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorophores. In addition to having an optimum emission range overlapping the excitation wavelength of the other fluorophore, the distance between D and A must be sufficiently small to allow the radiationless transfer of energy between the fluorophores.

FRET may be performed either in vivo or in vitro. Proteins are labeled either in vivo or in vitro by methods known in the art. According to the invention, two coiled-coil domains comprised either by the same or by different polypeptide molecules are differentially labeled, one with a donor and the other with an acceptor moiety, and differences in fluorescence between a test assay, comprising a protein modifying enzyme, and a control, in which the modifying enzyme is absent, are measured using a fluorimeter or laser-scanning microscope. It will be apparent to those skilled in the art that excitation/detection means can be augmented by the incorporation of photomultiplier means to enhance detection sensitivity. The differential labels may comprise either two different fluorescent moieties (e.g., fluorescent proteins as described below or the fluorophores rhodamine, fluorescein, SPQ, and others as are known in the art) or a fluorescent moiety and a molecule known to quench its signal; differences in the proximity of the coiled-coil domains with and without the protein-modifying enzyme can be gauged based upon a difference in the fluorescence spectrum or intensity observed.

This combination of protein-labelling methods and devices confers a distinct advantage over prior art methods for determining the activity of protein-modifying enzymes, as described above, in that results of all measurements are observed in real time (i.e., as a reaction progresses). This is significantly advantageous, as it allows both for rapid data collection and yields information regarding reaction kinetics under various conditions.

A sample, whether in vitro or in vivo, assayed according to the invention therefore comprises a mixture at equilibrium of polypeptides comprising labeled coiled-coil domains which, when disassociated from one another, fluoresce at one frequency and, when complexed together, fluoresce at another frequency or, alternatively, of molecules which either do or do not fluoresce depending upon whether or not they are associated.

Figure 2:
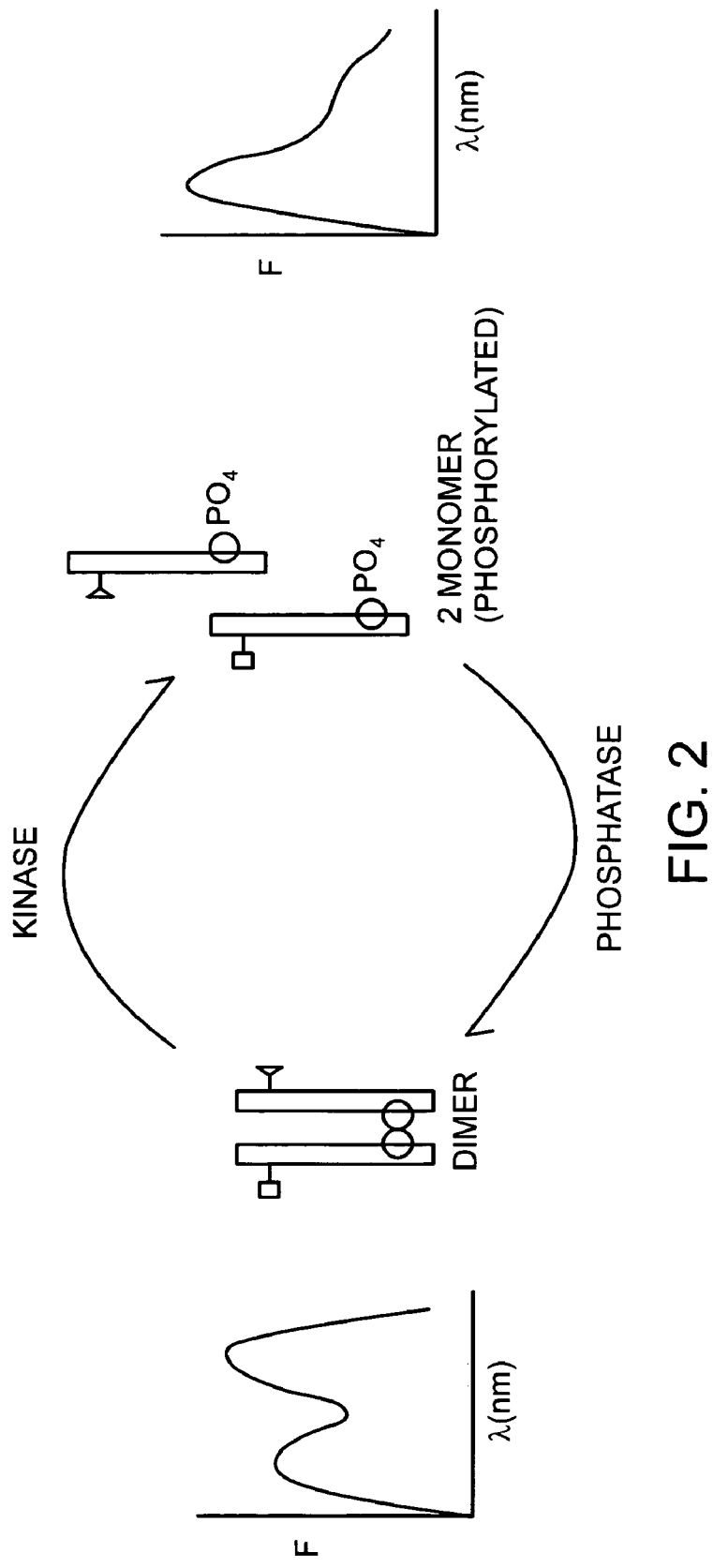

The coiled-coil portion of a polypeptide comprising a coiled-coil is modified to allow the attachment of a fluorescent moiety to the surface of the α-helix or is fused in-frame with a fluorescent protein, as described below. The choice of fluorescent moiety will be such that upon excitation with light, labeled peptides which are associated will show optimal energy transfer between fluorophores. In the presence of a protein modifying enzyme (e.g., a ubiquitinating-, ADP-ribosylating- or glycosylating enzyme), the polypeptides comprising coiled-coils dissociate due to disruption of the coiled-coil structure which occurs as a consequence of modification of the enzyme recognition site, thereby leading to a decrease in energy transfer and increased emission of light by the donor fluorophore. In this way, the state of polypeptide modification can be monitored and quantitated in real-time. This scheme, which represents the broadest embodiment of the invention, is shown in FIG. 2.

As used herein, the terms "fluorophore" and "fluorochrome" refer interchangeably to a molecule which is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelength that the fluorophore releases energy or fluoresces.

A non-limiting list of chemical fluorophores of use in the invention, along with their excitation and emission wavelengths, is presented in Table 1.

TABLE 1

| Fluorophore | Excitation (nm) | Emission (nm) | Color |
| --- | --- | --- | --- |
| PKH2 | 490 | 504 | green |
| PKH67 | 490 | 502 | green |
| Fluorescein (FITC) | 495 | 525 | green |
| Hoechst 33258 | 360 | 470 | blue |
| R-Phycoerythrin (PE) | 488 | 578 | orange-red |

TABLE 1-continued

| Fluorophore | Excitation (nm) | Emission (nm) | Color |
| --- | --- | --- | --- |
| Rhodamine (TRITC) | 552 | 570 | red |
| Quantum Red™ | 488 | 670 | red |
| PKH26 | 551 | 567 | red |
| Texas Red | 596 | 620 | red |
| Cy3 | 552 | 570 | red |

Examples of fluorescent proteins which vary among themselves in excitation and emission maxima are listed in Table 1 of WO 97/28261 (Tsien et al., 1997, supra). These (each followed by [excitation max./emission max.] wavelengths expressed in nanometers) include wild-type Green Fluorescent Protein [395(475)/508] and the cloned mutant of Green Fluorescent Protein variants P4 [383/447], P4-3 [381/445], W7 [433(453)/475(501)], W2 [432(453)/480], S65T [489/511], P4-1 [504(396)/480], S65A [471/504], S65C [479/507], S65L [484/510], Y66F [360/442], Y66W [458/480], 10c [513/527], W1B [432(453)/476(503)], Emerald [487/508] and Sapphire [395/511]. This list is not exhaustive of fluorescent proteins known in the art; additional examples are found in the Genbank and SwissProt public databases.

A number of parameters of fluorescence output are envisaged including
1) measuring fluoresence emitted at the emission wavelength of the acceptor (A) and donor (D) and determining the extent of energy transfer by the ratio of their emission amplitudes;
2) measuring the fluoresence lifetime of D;
3) measuring the rate of photobleaching of D;
4) measuring the anistropy of D and/or A; or
5) measuring the Stokes shift monomer; eximer fluorescence.

Fluorescent Protein Moieties in Assays of the Invention

In a FRET assay of the invention, the fluorescent protein moieties are chosen such that the excitation spectrum of one of the moieties (the acceptor moiety) overlaps with the emission spectrum of the excited fluorescent moiety (the donor moiety). The donor moiety is excited by light of appropriate intensity within the donor's excitation spectrum. The donor then emits some of the absorbed energy as fluorescent light and dissipates some of the energy by FRET to the acceptor fluorescent moiety. The fluorescent energy it produces is quenched by the acceptor fluorescent protein moiety. FRET can be manifested as a reduction in the intensity of the fluorescent signal from the donor, reduction in the lifetime of its excited state, and re-emission of fluorescent light at the longer wavelengths (lower energies) characteristic of the acceptor. When the donor and acceptor moieties become spatially separated, FRET is diminished or eliminated.

One can take advantage of the FRET exhibited by two polypeptides comprising coiled-coils labeled with different fluorescent protein moieties, wherein one coiled-coil of a polypeptide comprising a coiled-coil is linked to a donor and another to an acceptor moiety, in monitoring protein modification according to the present invention. A single polypeptide may comprises a blue fluorescent protein donor moiety and a green fluorescent protein acceptor moiety, wherein each is fused to a different coiled-coil within a polypeptide comprising a coiled-coil; such a construct is herein referred to as a "tandem" fusion protein. Alternatively, two distinct polypeptides ("single" fusion proteins) each comprising a coiled-coil may be differentially labeled with the donor and acceptor fluorescent protein moieties, respectively. The construction and use of tandem fusion proteins in the invention can reduce significantly the molar concentration of peptides necessary to effect an association between differentially-labeled coiled-coils within one of more polypeptides comprising a coiled-coil relative to that required when single fusion proteins are instead used. The labeled coiled-coils comprised by polypeptides comprising a coiled-coil may be produced via the expression of recombinant nucleic acid molecules comprising an in-frame fusion of sequences encoding a coiled-coil within a polypeptide comprising a coiled-coil and a fluorescent protein moiety either in vitro (e.g., using a cell-free transcription/translation system, as described below, or instead using cultured cells transformed or transfected using methods well known in the art) or in vivo, for example in a trangenic animal including, but not limited to, insects, amphibians and mammals. A recombinant nucleic acid molecule of use in the invention may be constructed and expressed by molecular methods well known in the art, and may additionally comprise sequences including, but not limited to, those which encode a tag (e.g., a histidine tag) to enable easy purification, a secretion signal, a nuclear localization signal or other primary sequence signal capable of targeting the construct to a particular cellular location, if it is so desired.

The means by which two polypeptides comprising coiled-coils are assayed for association using fluorescent protein moiety labels according to the invention may be briefly summarized as follows:

Whether or not the two coiled-coils are present on a single polypeptide molecule, one is labeled with a green fluorescent protein, while the other is preferably labeled with a red or, alternatively, a blue fluorescent protein. Useful donor: acceptor pairs of flurescent proteins (see Tsien et al., 1997, supra) include, but are not limited to:

Donor: S72A, K79R, Y145F, M153A and T203I (excitation λ 395 nm; emission λ 511)

Acceptor: S659, S72A, K79R and T203Y (wavelengths not noted), or

T203Y/S65G, V68L, Q69K or S72A (excitation λ 515 nm; emission λ 527 nm).

An example of a blue:green pairing is P4-3 (shown in Table 1 of Tsien et al., 1997, supra) as the donor moiety and S65C (also of Table 1 of Tsien et al., 1997, supra) as the acceptor moiety. The polypeptides comprising coiled-coils are exposed to light at, for example, 368 nm, a wavelength that is near the excitation maximum of P4-3. This wavelength excites S65C only minimally. Upon excitation, some portion of the energy absorbed by the blue fluorescent protein moiety is transferred to the acceptor moiety through FRET if the two polypeptides comprising coiled-coils are in close association. As a result of this quenching, the blue fluorescent light emitted by the blue fluorescent protein is less bright than would be expected if the blue fluorescent protein existed in isolation. The acceptor moiety (S65C) may re-emit the energy at longer wavelength, in this case, green fluorescent light.

After modification (e.g., phosphorylation, ADP-ribosylation, ubiquitination or glycosylation, all as described below) of one or both of the coiled-coils of a polypeptide comprising a coiled-coil by an enzyme, the two polypeptides comprising coiled-coils (and, hence, the green and red or, less preferably, green and blue fluorescent proteins) physically separate or associate, accordingly inhibiting or promoting FRET. For example, if activity of the modifying enzyme results in dissociation of a protein:protein dimer, the intensity of visible blue fluorescent light emitted by the blue fluorescent protein increases, while the intensity of visible green light emitted by the green fluorescent protein as a result of FRET, decreases.

Such a system is useful to monitor the activity of enzymes that modify the coiled-coils of one or more polypeptides comprising a coiled-coil to which the fluorescent protein moieties are fused as well as the activity of modulators or candidate modulators of those enzymes.

In particular, this invention contemplates assays in which the amount- or activity of a modifying enzyme in a sample is determined by contacting the sample with a pair of polypeptides comprising coiled-coil motifs differentially labeled with fluorescent proteins, as described above, and measuring changes in fluorescence of the donor moiety, the acceptor moiety or the relative fluorescence of both. Fusion proteins, as described above, which comprise either one or both labeled polypeptides comprising coiled-coils of an assay of the invention can be used for, among other things, monitoring the activity of a modifying enzyme inside the cell that expresses the recombinant tandem construct or two different recombinant constructs.

Advantages of single- and tandem fluorescent protein/ polypeptide comprising a coiled-coil fusion constructs include the greater extinction coefficient and quantum yield of many of these proteins compared with those of the Edans fluorophore. Also, the acceptor in such a construct or pair of constructs is, itself, a fluorophore rather than a non-fluorescent quencher like Dabcyl. Thus, the enzyme's substrate, i.e., the unmodified coiled-coils of the construct(s) and products (i.e., the coiled-coils after modification) are both fluorescent but with different fluorescent characteristics.

In particular, the substrate and modified products exhibit different ratios between the amount of light emitted by the donor and acceptor moieties. Therefore, the ratio between the two fluorescences measures the degree of conversion of substrate to products, independent of the absolute amount of either, the optical thickness of the sample, the brightness of the excitation lamp, the sensitivity of the detector, etc. Furthermore, *Aequorea*-derived or -related fluorescent protein moieties tend to be protease resistant. Therefore, they are likely to retain their fluorescent properties throughout the course of an experiment.

Polypeptide Comprising a Coiled-Coil/Fluorescent Protein Fusion Constructs According to the Invention As stated above, recombinant nucleic acid constructs of particular use in the invention are those which comprise in-frame fusions of sequences encoding a polypeptide comprising a coiled-coil motifs and a fluorescent protein. If two coiled-coils are to be expressed as part of a single polypeptide, the nucleic acid molecule additionally encodes, at a minimum, a donor fluorescent protein moiety fused to one coiled-coil, an acceptor fluorescent protein moiety fused to a second coiled-coil, a linker moiety that couples the two coiled-coils and is of sufficient length and flexibility to allow for folding of the polypeptide and pairing of the two coiled-coils and gene regulatory sequences operatively linked to the fusion coding sequence. If single fusion proteins are instead encoded (whether by one or more nucleic acid molecules), each nucleic acid molecule need only encode a polypeptide comprising a coiled-coil fused either to a donor or acceptor fluorescent protein moiety and operatively linked to gene regulatory sequences.

"Operatively-linked" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

As described above, the donor fluorescent protein moiety is capable of absorbing a photon and transferring energy to another fluorescent moiety. The acceptor fluorescent protein moiety is capable of absorbing energy and emitting a photon. If needed, the linker moiety connects the two polypeptides comprising coiled-coils either directly or indirectly, through an intermediary linkage with one or both of the donor and acceptor fluorescent protein moieties. Regardless of the relative order of the first and second polypeptides comprising coiled-coils and the donor and acceptor fluorescent protein moieties on a polypeptide molecule, it is essential that sufficient distance be placed between the donor and acceptor by the linker and/or the polypeptides comprising coiled-coils to ensure that FRET does not occur unless the two coiled-coils dimerize. It is desirable, as described in greater detail in WO97/28261, to select a donor fluorescent protein moiety with an emission spectrum that overlaps with the excitation spectrum of an acceptor fluorescent protein moiety. In some embodiments of the invention the overlap in emission and excitation spectra will facilitate FRET. Such an overlap is not necessary, however, if intrinsic fluorescence is measured instead of FRET. A fluorescent protein of use in the invention includes, in addition to those with intrinsic fluorescent properties, proteins that fluoresce due intramolecular rearrangements or the addition of cofactors that promote fluorescence.

For example, green fluorescent proteins ("GFPs") of cnidarians, which act as their energy-transfer acceptors in bioluminescence, can be used in the invention. A green fluorescent protein, as used herein, is a protein that fluoresces green light, and a blue fluorescent protein is a protein that fluoresces blue light. GFPs have been isolated from the Pacific Northwest jellyfish, *Aequorea victoria*, from the sea pansy, *Renilla reniformis*, and from *Phialidium gregarium*. (Ward et al., 1982, *Photochem. Photobiol.*, 35: 803–808; Levine et al., 1982, *Comp. Biochem. Physiol.*, 72B: 77–85).

A variety of *Aequorea*-related GFPs having useful excitation and emission spectra have been engineered by modifying the amino acid sequence of a naturally occurring GFP from *Aequorea victoria*. (Prasher et al., 1992, *Gene*, 111: 229–233; Heim et al., 1994, *Proc. Natl. Acad. Sci. USA.*, 91: 12501–12504; PCT/US95/14692). As used herein, a fluorescent protein is an *Aequorea*-related fluorescent protein if any contiguous sequence of 150 amino acids of the fluorescent protein has at least 85% sequence identity with an amino acid sequence, either contiguous or non-contiguous, from the wild-type *Aequorea* green fluorescent protein (SwissProt Accession No. P42212). More preferably, a fluorescent protein is an *Aequorea*-related fluorescent protein if any contiguous sequence of 200 amino acids of the fluorescent protein has at least 95% sequence identity with an amino acid sequence, either contiguous or noncontiguous, from the wild type *Aequorea* green fluorescent protein of SwissProt Accession No. P42212. Similarly, the fluorescent protein may be related to *Renilla* or *Phialidium* wild-type fluorescent proteins using the same standards.

*Aequorea*-related fluorescent proteins include, for example, wild-type (native) *Aequorea victoria* GFP, whose nucleotide and deduced amino acid sequences are presented in Genbank Accession Nos. L29345, M62654, M62653 and others *Aequorea*-related engineered versions of Green Fluorescent Protein, of which some are listed above. Several of these, i.e., P4, P4-3, W7 and W2 fluoresce at a distinctly shorter wavelength than wild type.

Recombinant nucleic acid molecules encoding single- or tandem fluorescent protein/polypeptide comprising a coiled-coil fusion proteins useful in the invention may be expressed either for in vivo assay of the activity of a modifying enzyme on the encoded products. Alternatively, the encoded fusion protiens may be isolated prior to assay, and instead assayed in a cell-free in vitro assay system, as described elsewhere herein.

As used herein, the terms "protein", "subunit" and "domain" refer to a linear sequence of amino acids which exhibits biological function. This linear sequence includes full-length amino acid sequences (e.g. those encoded by a full-length gene), or a portion or fragment thereof, provided the biological function is maintained by that portion or fragment. The terms subunit and domain also may refer to polypeptides and peptides having biological function. A peptide useful in the invention will at least have a binding capability, i.e, with respect to binding as or to a binding partner, and also may have another biological function that is a biological function of a protein or domain from which the peptide sequence is derived.

Protein Modifications in Assays of the Invention

ADP-ribosylation

Mono-ADP-ribosylation is a post-translational modification of proteins which is currently thought to play a fundamental role in cellular signalling. A number of mono-ADP-ribosyl-transferases have been identified, including endogenous enzymes from both bacterial and eukaryotic sources and bacterial toxins. A mono-ADP-riboylating enzyme, using as substrates the protein to be modified and nicotinamide adenine dinucleotide (NAD$^+$), is NAD:Arginine ADP ribosyltransferase (Zolkiewska et al., 1992, *Proc. Natl. Acad. Sci. U.S.A.*, 89: 11352–11356). The reactions catalysed by bacterial toxins such as cholera and pertussis toxin are well understood, the activity of these toxins result in the permanent modification of heterotrimeric G proteins.

Endogenous transferases are also thought to modify G proteins and therefore to play a role in signal transduction in the cell (de Murcia et al., 1995, *Trends Cell Biol.*, 5: 78–81). The extent of the effects that ADP-ribosylation can mediate in the cell is illustrated by the example of brefeldin A, a fungal toxin metabolite of palmitic acid. This toxin induces the mono-ADP-ribosylation of BARS-S0 (a G protein involved in membrane transport) and glyceraldehyde-3-phosphate dehydrogenase. The cellular effects of brefeldin A include the blocking of constitutive protein secretion and the extensive disruption of the Golgi apparatus. Inhibitors of the brefeldin A mono-ADP-ribosyl-transferase reaction have been shown to antagonise the disassembly of the Golgi apparatus induced by the toxin (Weigert et al., 1997, *J. Biol. Chem.*, 272: 14200–14207). A number of amino acid residues within proteins have been shown to function as ADP-ribose acceptors. Bacterial transferases have been identified which modify arginine, asparagine, cysteine and diphthamide residues in target proteins. Endogenous eukaryotic transferases are known which also modify these amino acids, in addition there is evidence that serine, threonine, tyrosine, hydroxyproline and histidine residues may act as ADP-ribose acceptors but the relevant transferases have not yet been identified (Cervantes-Laurean et al., 1997, *Methods Enzymol.*, 280: 275–287 and references therein).

Poly-ADP-ribosylation is thought to play an important role in events such as DNA repair, replication, recombination and packaging and also in chromosome decondensation. The enzyme responsible for the poly-ADP-ribosylation of proteins involved in these processes is poly (ADP-ribose) polymerase (PARP; for *Drosophila melanogaster* PARP, see Genbank Accession Nos. D13806, D13807 and D13808). The discovery of a leucine zipper in the self-poly(ADP-ribosyl)ation domain of the mammalian PARP (Uchida et al., 1993, *Proc. Natl. Acad. Sci. U.S.A.*, 90: 3481–3485) suggested that this region may be important for the dimerisation of PARP and also its interaction with other proteins (Poly(ADP-ribose) polymerase is a catalytic dimer and the automodification reaction is intermolecular, Mendoza-Alvarez et al., 1993, *J. Biol. Chem.*, 268: 22575–22580).

"Specific examples of ADP ADP-ribosylation sites are those found at $Cys_3$ and $Cys_4$ (underlined) of the B-50 protein (Coggins et al., 1993, *J. Neurochem.*, 60: 368–371; SwissProt Accession No. P06836):

MLCCMRRTKQVEKNDDD (SEQ ID NO. 18)

and PY(the Y subunit of cycylic CMP phophodiesterase; Bondarenko et al., 1997, *J. Biol. Chem.*, 272: 15856–15864; Genbank Accession No. X04270):

FKQRQTRQFK (SEQ ID NO. 19)."

A survey of the literature suggests that ADP-ribosylation is a very important post-translational modification whose significance has only relatively recently been appreciated and that as the field develops, the scope for applying this concept to the study ADP-ribosylation will increase.

Ubiquitination

Ubiquitination of a protein targets the protein for destruction by the proteosome. This process of destruction is very rapid ($t_{1/2}$~60 seconds), and many proteins with rapid turnover kinetics are destroyed via this route. These include cyclins, p53, transcription factors and transcription regulatory factors, among others. Thus, ubiquitination is important in processes such as cell cycle control, cell growth, inflammation, signal transduction; in addition, failure to ubiquitinate proteins in an appropriate manner is implicated in malignant transformation. Ubiquitin is a 76-amino-acid protein which is covalently attached to a target protein by an isopeptide bond, between the ∈-amino group of a lysine residue and the C-terminal glycine residue of ubiquitin. Such modification is known as mono-ubiquitination, and this can occur on multiple Lys residues within a target protein. Once attached, the ubiquitin can itself be ubiquitinated, thus forming extended branched chains of polyubiquitin. It is this latter state which signals destruction of the target protein by the proteosome. In the process of destruction, it appears that the polyubiquitinated protein is taken to the proteosome via a molecular chaperone protein, the ubiquitin molecules are removed undamaged (and recycled) and the target is degraded.

Ubiquitination is a complex process, which requires the action of three enzymes: Ubiquitin activating enzyme E1, (for human, Genbank Accession No. X56976), ubiquitin conjugating enzyme E2, also referred to as the ubiquitin carrier protein, (for human 17 kDa form, Genbank Accession No. X78140) and Ubiquitin protein ligase E3α (UBR1; human, Genbank Accession No. AF061556). There are multiple forms of each of these enzymes in the cell, and the above examples are, therefore, non-limiting.

The signals contained within a protein which determine whether the protein is subject to the process of ubiquitination and destruction are two-fold: first, the identity of the N-terminal amino acid (so called N-end rule, Varshavsky, 1996, *Proc. Natl. Acad. Sci. U.S.A.*, 93: 12142–12149), and secondly the presence of a suitably positioned Lys residue in the protein (Varshavsky, 1996, supra). This Lys can be up to ~30 amino acids away from the N-terminus in experimental examples studied where the N-terminus is a flexible, poorly-structured element of the protein (Varshavsky, 1996, supra) or could potentially be anywhere in the sequence where this presents it at an appropriate location relative to the N-terminus. An appropriate location is one which allows interaction of both the N-terminal residue and this integral lysine with the enzyme(s) responsible for ubiquitination, presumably simultaneously. The Lys residue becomes ubiquitinated, and the process of destruction is initiated. N-terminal residues can be classed as stabilizing (s) or destabilizing (d), and the inclusion of an amino acid in one of these broad classes is species-dependent (prokaryotes differ from yeast, which differs from mammals; Varshavsky, 1996, supra).

In a dimeric (or other oligomeric protein) the destabilizing N-terminal residue and the internal Lys can be in cis (on a single peptide), but may also be in trans (on two different polypeptides). The trans-recognition event will only take place while the complex is physically associated. Only the ubiquitinated subunit is proteolyzed (Varsharsky, 1996, supra).

"Two examples of ubiquitination sites from natural proteins, IκB (Dai et al., 1998, *J. Biol. Chem*, 273: 3562–3573; Genbank Accession No. M69043) and β-galactosidase (Johnson et al., 1990, *Nature*, 346: 287–291) are as follows:

IκB $NH_3$-MFQAAERPQEWAMEGPRDGLKKERLLD-DRH-COOH (SEQ ID NO. 20)

β-galactosidase $NH_3$-HGSGAWLLPVSLVKRKTTLAP-COOH (SEQ ID NO. 21)

where the ubiquitinated lysine residue is underlined for each (e.g., $Lys_{15}$ and $Lys_{17}$ for β-galactosidase)."

According to the invention, a ubiquitination assay measures the addition of ubiquitin to—, rather than the destruction of—, a polypeptide comprising a coiled-coil.

Glycosylation

N-linked glycosylation is a post-translational modification of proteins which occurs in the endoplasmic reticulum and golgi apparatus and is utilized with some proteins en route for secretion or destined for expression on the cell surface or in another organelle. The carbohydrate moiety is attached to Asn residues in the non-cytoplasmic domains of the target proteins, and the consensus sequence (Shakineshleman, 1996, *Trends Glycosci. Glycotech.*, 8: 115–130) for a glycosylation site is:

NxS/T, where x cannot be proline or aspartic acid. An enzyme known to mediate N-glycosylation at the initial step of synthesis of dolichol-P-P-oligosaccharides is UDP-N-Acetylglucosamine-Dolichyl-phosphate-N-acetylglucosamine phosphotransferase (for mouse, Genbank Accession Nos. X65603 and S41875).

Oxygen-linked glycosylation also occurs in nature with the attachment of various sugar moieties to Ser or Thr residues (Hansen et al., 1995, *Biochem. J.*, 308: 801–813). Intracellular proteins are among the targets for O-glycosylation through the dynamic attachment and removal of O-N-Acetyl-D-glucosamine (O-GlcNAc; reviewed by Hart, 1997, *Ann. Rev. Biochem.*, 66: 315–335). Proteins known to be O-glycosylated include cytoskeletal proteins, transcription factors, the nuclear pore protein complex, and tumor-suppressor proteins (Hart, 1997, supra). Frequently these proteins are also phosphoproteins, and there is a suggestion that O-GlcNAc and phosphorylation of a protein play reciprocal roles. Furthermore, it has been proposed that the glycosylation of an individual protein regulates protein:protein interactions in which it is involved.

"Specific sites for the addition of O-GlcNAc are found, for example, at $Ser_{277}$, $Ser_{316}$ and $Ser_{383}$ of $p67^{SRF}$ (Reason et al., 1992, *J. Biol. Chem.*, 267: 16911–16921; Genbank Accession No. J03161). The recognition sequences encompassing these residues are shown below:

$^{274}$GTTSTIQTAP (SEQ ID NO. 22)
$^{313}$SAVSSADGTVLK (SEQ ID NO. 23)
$^{374}$DSSTDLTQTSSSGTVTLP (SEQ ID NO. 24)"

"The identity of sites of O-GlcNAc is additionally known for a small number of proteins including c-myc ($Thr_{58}$, also a phosphorylation site; Chou et al., 1995, *J. Biol. Chem.*, 270: 18961–18965), the nucleopore protein p62 (see Reason et al., 1992, supra):

MAGGPADTSDPL (SEQ ID NO. 25)

and band 4.1 of the erythrocyte (see Reason et al., 1992, supra):

AQTITSETPSSTT (SEQ ID NO. 26).

The site at which modification occurs is, in each case, underlined. The reaction is mediated by O-GlcNAc transferase (Kreppel et al., 1997, *J. Biol. Chem.* 272: 9308–9315). These sequences are rich in helix breaking residues (e.g., G and P) and may therefore be difficult to incorporate into the coiled-coil framework, as it is an α-helical structure."

Phosphorylation

Protein phosphorylation is described at some length above and in the sections following.

Methods for Detection of Protein Modification in Real Time

A. In vitro Protein Modification and Detection Thereof

Modifying Enzymes

The invention requires the presence of a modifying enzyme which catalyzes either the addition or removal of a modifying group. A range of kinases, phosphatases and other modifying enzymes are available commercially (e.g. from Sigma, St. Louis, Mo.; Promega, Madison, Wis.; Boehringer Mannheim Biochemicals, Indianapolis, Ind.; New England Biolabs, Beverly, Mass.; and others). Alternatively, such enzymes may be prepared in the laboratory by methods well known in the art.

The catalytic sub-unit of protein kinase A (c-PKA) can be purified from natural sources (e.g. bovine heart) or from cells/organisms engineered to heterologously express the enzyme. Other isoforms of this enzyme may be obtained by these procedures. Purification is performed as previously described from bovine heart (Peters et al., 1977, *Biochemistry*, 16: 5691–5697) or from a heterologous source (Tsien et al., WO92/00388), and is in each case briefly summarized as follows:

Bovine ventricular cardiac muscle (2 kg) is homogenized and then centrifuged. The supernatant is applied to a strong anion exchange resin (e.g. Q resin, Bio-Rad) equilibrated in a buffer containing 50 mM Tris-HCl, 10 mM NaCl, 4 mM EDTA pH 7.6 and 0.2 mM 2-mercaptoethanol. The protein is eluted from the resin in a second buffer containing 50 mM Tris-HCl, 4 mM EDTA pH 7.6, 0.2 mM 2-mercaptoethanol, 0.5M NaCl. Fractions containing c-PKA are pooled and ammonium sulphate added to 30% saturation. Proteins precipitated by this are removed by centrifugation and the ammonium sulphate concentration of the supernatant was increased to 75% saturation. Insoluble proteins are collected by centrifugation (included c-PKA) and are dissolved in 30 mM phosphate buffer pH 7.0, 1 mM EDTA, 0.2 mM 2-mercaptoethanol. These proteins are then dialysed against the same buffer (500 volume excess) at 4° C. for two periods of 8 hours each. The pH of the sample is reduced to 6.1 by addition of phosphoric acid, and the sample is mixed sequentially with 5 batches of CM-Sepharose (Pharmacia, ~80 ml resin each) equilibrated in 30 mM phosphate pH 6.1, 1 mM EDTA, 0.2 mM 2-mercaptoethanol. Cyclic AMP (10 µM) is added to the material which fails to bind to the CM-Sepharose, and the sample-cAMP mix is incubated with a fresh resin of CM-Sepharose (~100 ml) equilibrated as before. c-PKA is eluted from this column following extensive washing in equilibration buffer by addition of 30 mM phosphate pH 6.1, 1 mM EDTA, 1M KCl, 0.2 mM 2-mercaptoethanol. Fractions containing c-PKA are pooled and concentrated by filtration through a PM-30 membrane (or similar). The c-PKA sample is then subjected to gel-filtration chromatography on a resin such as Sephacryl 200HR (Pharmacia).

The purification of recombinant c-PKA is as described in WO 92/00388. General methods of preparing pure and partially-purified recombinant proteins, as well as crude cellular extracts comprising such proteins, are well known in the art. Molecular methods useful in the production of recombinant proteins, whether such proteins are the enzymes to be assayed according to the invention or the labeled reporter polypeptides comprising a coiled-coil of the invention, are well known in the art (for methods of cloning, expression of cloned genes and protein purification, see Sambrook et al., 1989, *Molecular Cloning. A Laboratory Manual.*, 2nd Edition, Cold Spring Harbor Laboratory Press, Cold Spring Harbor, N.Y.; Ausubel et al., *Current Protocols in Molecular Biology*, copyright 1987–1994, Current Protocols, copyright 1994–1998, John Wiley & Sons, Inc.). The sequences of the catalytic subunit of several PKA molecules are found in the Genbank database (see PKA Cα, bovine, Genbank Accession Nos. X67154 and S49260; PKA Cβ1, bovine, Genbank Accession No. J02647; PKA Cβ2, bovine, M60482, the form most likely purified from bovine heart by the protocol described above).

According to the invention, assays of the activity of protein-modifying enzymes may be performed using crude cellular extracts, whether to test the activity of a recombinant protein or one which is found in nature, such as in a biological sample obtained from a test cell line or animal or from a clinical patient. In the former case, use of a crude cell extract enables rapid screening of many samples, which potentially finds special application in high-throughput screening methods, e.g. of candidate modulators of protein-modifying enzyme activity. In the latter case, use of a crude extract with the labeled reporter polypeptide comprising a coiled-coil of the invention facilitates easy and rapid assessment of the activity of an enzyme of interest in a diagnostic procedure, e.g., one which is directed at determining whether a protein-modifying enzyme is active at an a physiologically-appropriate level, or in a procedure designed to assess the efficacy of a therapy aimed at modulating the activity of a particular enzyme.

Synthesis of Polypeptides Comprising a Coiled-Coil

Polypeptides comprising a coiled-coil may be synthesised by Fmoc or Tboc chemistry according to methods known in the art (e.g., see Atherton et al., 1981, *J. Chem. Soc. Perkin I*, 1981(2): 538–546; Merrifield, 1963, *J. Am. Chem. Soc.*, 85: 2149–2154, respectively). Following deprotection and cleavage from the resin, peptides are desalted by gel filtration chromatography and analysed by mass spectroscopy, HPLC, Edman degradation and/or other methods as are known in the art for protein sequencing using standard methodologies.

Alternatively, nucleic acid sequences encoding such peptides may be expressed either in cells or in an in vitro transcription/translation system (see below) and, as with enzymes to be assayed according to the invention, the proteins purified by methods well known in the art.

Labelling Polypeptides Comprising a Coiled-Coil with Fluorophores

Polypeptides comprising coiled-coils are labeled with thiol reactive derivatives of fluorescein and tetramethylrhodamine (isothiocyanate or iodoacetamide derivatives, Molecular Probes, Eugene, Oreg., USA) using procedures described by Hermanson G. T., 1995, *Bioconjugate Techniques*, Academic Press, London. Alternatively, primary-amine-directed conjugation reactions can be used to label lysine sidechains or the free peptide N-terminus (Hermason, 1995, supra).

Purification of Fluorescent Peptides

Fluorescent peptides are separated from unreacted fluorophores by gel filtration chromatography or reverse phase HPLC.

Phosphorylation of Peptides in vitro

Peptides (0.01–1.0 µM) are phosphorylated by purified c-PKA in 50 mM Histidine buffer pH 7.0, 5 mM $MgSO_4$, 1 mM EGTA, 0.1–1.0 µM c-PKA, and 0.2 mM [$^{32}$P] γ-ATP (specific activity ~2Bq/pmol) at 30–37° C. for periods of time ranging from 0 to 60 minutes. Where the chemistry of the peptide is appropriate (i.e. having a basic charge) the phosphopeptide is captured on a cation exchange filter paper (e.g. phosphocellulose P81 paper; Whatman), and reactants are removed by extensive washing in 1% phosphoric acid (see Casnellie, 1991, *Methods Enzymol.*, 200: 115–120). Alternatively, phosphorylation of samples is terminated by the addition of SDS-sample buffer (Laemmli, 1970, *Nature*, 227: 680–685) and the samples analysed by SDS-PAGE electrophoresis, autoradiography and scintillation counting of gel pieces.

Dephosphorylation of Peptides in vitro

The dephosphorylation of peptides phosphorylated as above is studied by removal of ATP (through the addition of 10 mM glucose and 30 U/ml hexokinase; Sigma, St. Louis, Mo.) and addition of protein phosphatase-1 (Sigma). Dephosphorylation is followed at 30–37° C. by quantitation of the remaining phosphopeptide component at various time points, determined as above.

Fluorescence Measurements of Protein Modification in vitro in Real Time

Donor and acceptor fluorophore-labeled polypeptides comprising coiled-coils (molar equivalents of fluorophore-labeled polypeptide or molar excess of acceptor-labeled polypeptide) are first mixed (if the two coiled-coils are present on separate polypeptides). Samples are analyzed in a fluorimeter using excitation wavelengths relevant to the donor fluorescent moiety and emission wavelengths relevant to both the donor and acceptor moieties. A ratio of emission from the acceptor over that from the donor following excitation at a single wavelength is used to determine the efficiency of fluorescence energy transfer between fluorophores, and hence their spatial proximity. Typically, measurements are performed at 0–37° C. as a function of time following the addition of the modifying enzyme (and, optionally, a modulator or candidate modulator of function for that enzyme, as described below) to the system in 50 mM histidine pH 7.0, 120 mM KCl, 5 mM $MgSO_4$, 5 mM NaF, 0.05 mM EGTA and 0.2 mM ATP. The assay may be performed at a higher temperature if that temperature is compatible with the enzyme(s) under study.

Alternative Cell-Free Assay Systems of the Invention

A cell-free assay system according to the invention is required to permit dimerization of unmodified, labeled polypeptides comprising coiled-coils to occur. As indicated herein, such a system may comprise a low-ionic-strength buffer (e.g., physiological salt, such as simple saline or phosphate- and/or Tris-buffered saline or other as described above), a cell culture medium, of which many are known in the art, or a whole or fractionated cell lysate. The components of an assay of protein modification according to the invention may be added into a buffer, medium or lysate or may have been expressed in cells from which a lysate is derived. Alternatively, a cell-free transcription- and/or translation system may be used to deliver one or more of these components to the assay system. Nucleic acids of use in cell-free expression systems according to the invention are as described for in vivo assays, below.

An assay of the invention may be peformed in a standard in vitro transcription/translation system under conditions which permit expression of a recombinant or other gene. The TNT® T7 Quick Coupled Transcription/Translation System (Cat. #L1170; Promega) contains all reagents necessary for in vitro transcription/translation except the DNA of interest and the detection label; as discussed below, polypeptides comprising coiled-coils may be encoded by expression constructs in which their coding sequences are fused in-frame to those encoding fluorescent proteins. The TNT® Coupled Reticulocyte Lysate Systems (comprising a rabbit reticulocyte lysate) include: TNT® T3 Coupled Reticulocyte Lysate System (Cat. # L4950; Promega); TNT® T7 Coupled Reticulocyte Lysate System (Cat. #L4610; Promega); TNT® SP6 Coupled Reticulocyte Lysate System (Cat. #L4600; Promega); TNT® T7/SP6 Coupled Reticulocyte Lysate System (Cat. #L5020; Promega); TNT® T7/T3 Coupled Reticulocyte Lysate System (Cat. #L5010; Promega).

An assay involving a cell lysate or a whole cell (see below) may be performed in a cell lysate or whole cell preferably eukaryotic in nature (such as yeast, fungi, insect, e.g., *Drosophila*), mouse, or human). An assay in which a cell lysate is used is performed in a standard in vitro system under conditions which permit gene expression. A rabbit reticulocyte lysate alone is also available from Promega, either nuclease-treated (Cat. #L4960) or untreated (Cat. #L4151).

Candidate Modulators of Protein-Modifying Enzymes to be Screened According to the Invention Whether in vitro or in an in vivo system (see below), the invention encompasses methods by which to screen compositions which may enhance, inhibit or not affect (e.g., in a cross-screening procedure in which the goal is to determine whether an agent intended for one purpose additionally affects general cellular functions, of which protein modification is an example) the activity of a protein-modifying enzyme.

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N. J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

Candidate modulators which may be screened according to the methods of the invention include receptors, enzymes, ligands, regulatory factors, and structural proteins. Candidate modulators also include nuclear proteins, cytoplasmic proteins, mitochondrial proteins, secreted proteins, plasmalemma-associated proteins, serum proteins, viral antigens, bacterial antigens, protozoal antigens and parasitic antigens. Candidate modulators additionally comprise proteins, lipoproteins, glycoproteins, phosphoproteins and nucleic acids (e.g., RNAs such as ribozymes or antisense nucleic acids). Proteins or polypeptides which can be screened using the methods of the present so invention include hormones, growth factors, neurotransmitters, enzymes, clotting factors, apolipoproteins, receptors, drugs, oncogenes, tumor antigens, tumor suppressors, structural proteins, viral antigens, parasitic antigens, bacterial antigens and antibodies (see below).

Candidate modulators which may be screened according to the invention also include substances for which a test cell or organism might be deficient or that might be clinically effective in higher-than-normal concentration as well as those that are designed to eliminate the translation of unwanted proteins. Nucleic acids of use according to the invention not only may encode the candidate modulators described above, but may eliminate or encode products which eliminate deleterious proteins. Such nucleic acid sequences are antisense RNA and ribozymes, as well as DNA expression constructs that encode them. Note that antisense RNA molecules, ribozymes or genes encoding them may be administered to a test cell or organism by a method of nucleic acid delivery that is known in the art, as described below. Inactivating nucleic acid sequences may encode a ribozyme or antisense RNA specific for the a target mRNA. Ribozymes of the hammerhead class are the smallest known, and lend themselves both to in vitro synthesis and delivery to cells (summarized by Sullivan, 1994, *J. Invest. Dermatol.*, 103: 85–98S; Usman et al., 1996, *Curr. Opin. Struct. Biol.*, 6: 527–533).

As stated above, antibodies are of use in the invention as modulators (specifically, as inhibitors) of protein-modifying enzymes. Methods for the preparation of antibodies are well known in the art, and are briefly summarized as follows:

Either recombinant proteins or those derived from natural sources can be used to generate antibodies using standard techniques, well known to those in the field. For example, the proteins are administered to challenge a mammal such as a monkey, goat, rabbit or mouse. The resulting antibodies can be collected as polyclonal sera, or antibody-producing cells from the challenged animal can be immortalized (e.g. by fusion with an immortalizing fusion partner) to produce monoclonal antibodies.

1. Polyclonal Antibodies.

The antigen protein may be conjugated to a conventional carrier in order to increases its immunogenicity, and an antiserum to the peptide-carrier conjugate is raised. Coupling of a peptide to a carrier protein and immunizations may be performed as described (Dymecki et al., 1992, *J. Biol. Chem.*, 267: 4815–4823). The serum is titered against protein antigen by ELISA (below) or alternatively by dot or spot blotting (Boersma and Van Leeuwen, 1994, *J. Neurosci. Methods*, 51: 317). At the same time, the antiserum may be used in tissue sections prepared as described below. The serum is shown to react strongly with the appropriate peptides by ELISA, for example, following the procedures of Green et al., 1982, *Cell*, 28: 477–487.

2. Monoclonal antibodies.

Techniques for preparing monoclonal antibodies are well known, and monoclonal antibodies may be prepared using a candidate antigen whose level is to be measured or which is to be either inactivated or affinity-purified, preferably bound to a carrier, as described by Arnheiter et al., *Nature*, 294, 278–280 (1981).

Monoclonal antibodies are typically obtained from hybridoma tissue cultures or from ascites fluid obtained from animals into which the hybridoma tissue is introduced. Nevertheless, monoclonal antibodies may be described as being "raised to" or "induced by" a protein.

Monoclonal antibody-producing hybridomas (or polyclonal sera) can be screened for antibody binding to the target protein. By antibody, we include constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

Determination of Activity of Candidate Modulator of a Protein-Modifying Enzyme

A candidate modulator of the activity of a protein-modifying enzyme may be assayed according to the invention as described herein, is determined to be effective if its use results in a difference of about 10% or greater relative to controls in which it is not present (see below) in FRET resulting from the association of labeled polypeptides comprising coiled-coils in the presence of a protein-modifying enzyme.

The level of activity of a candidate modulator may be quantified using any acceptable limits, for example, via the following formula:

$$\text{Percent Modulation} = \frac{(\text{Index}_{Control} - \text{Index}_{Sample})}{(\text{Index}_{Control})} \times 100$$

where $\text{Index}_{Control}$ is the quantitative result (e.g., amount of FRET, rate of change in FRET) obtained in assays that lack the candidate inhibitor (in other words, untreated controls), and $\text{Index}_{Sample}$ represents the result of the same measurement in assays containing the candidate inhibitor. As described below, control measurements are made with differentially labeled polypeptides comprising coiled-coils only and with these molecules plus a protein-modifying enzyme which recognizes a site present on them.

Such a calculation is used in either in vitro or in vivo assays performed according to the invention.

B. In vivo Assays of Enzymatic Activity According to the Invention

Reporter Group Protein Modification in Living Cells

Differentially-labeled polypeptides comprising coiled-coils of the invention are delivered (e.g., by microinjection) to cells, such as smooth muscle cells (DDT1) or ventricular cardiac myocytes as previously described (Riabowol et al., 1988, *Cold Spring Harbor Symposia on Quantitative Biology*, 53: 85–90). The ratio of emission from the labeled molecule(s) is measured as described above via a photomultiplier tube focused on a single cell. Activation of a kinase (e.g., PKA by the addition of dibutyryl cAMP or β-adrenergic agonists) is performed, subsequent inhibition is performed by removal of stimulus and by addition of a suitable antagonist (e.g., cAMP antagonist Rp-cAMPS). As described elsewhere herein, an ADP ribosylating enzyme may be stimulated with cholera toxin (G-protein recognition feature) or with brefeldin A.

Heterologous Expression of Peptides

Polypepitides comprising coiled-coils can be synthesized from the heterologous expression of DNA sequences for coiled-coil motifs of interest modified to include the sequence for enzmyatic modification as appropriate, or synthetic gene of the same.

Expression can be in procaryotic or eukaryotic cells using a variety of plasmid vectors capable of instructing heterologous expression. Purification of these products is achieved by destruction of the cells (e.g. French Press) and chromatographic purification of the products. This latter procedure can be simplified by the inclusion of an affinity purification tag at one extreme of the peptide, separated from the peptide by a protease cleavage site if necessary.

The Use of Cells or Whole Organisms in Assays of the Invention

When performed using cells, the assays of the invention are broadly applicable to a host cell susceptible to transfection or transformation including, but not limited to, bacteria (both gram-positive and gram-negative), cultured- or explanted plant (including, but not limited to, tobacco, arabidopsis, carnation, rice and lentil cells or protoplasts), insect (e.g., cultured *Drosophila* or moth cell lines) or vertebrate cells (e.g., mammalian cells) and yeast.

Organisms are currently being developed for the expression of agents including DNA, RNA, proteins, non-proteinaceous compounds, and viruses. Such vector microorganisms include bacteria such as *Clostridium* (Parker et al., 1947, *Proc Soc. Exp. Biol. Med.*, 66: 461–465; Fox et al., 1996, *Gene Therapy*, 3: 173–178; Minton et al., 1995, *FEMS Microbiol. Rev.*, 17: 357–364), *Salmonella* (Pawelek et al., 1997, *Cancer Res.*, 57: 4537–4544; Saltzman et al., 1996, *Cancer Biother. Radiopharm.*, 11: 145–153; Carrier et al., 1992, *J. Immunol.*, 148: 1176–1181; Su et al., 1992, *Microbiol. Pathol.*, 13: 465–476; Chabalgoity et al., 1996, *Infect. Immunol.*, 65: 2402–2412), *Listeria* (Schafer et al., 1992, *J. Immunol.*, 149: 53–59; Pan et al., 1995, *Nature Med.*, 1: 471–477) and *Shigella* (Sizemore et al., 1995, *Science*, 270: 299–302), as well as yeast, mycobacteria, slime molds (members of the taxa Dictyosteliida—such as of the genera *Polysphondylium* and *Dictystelium*, e.g. *Dictyostelium discoideum*—and Myxomycetes—e.g. of the genera *Physarum* and *Didymium*) and members of the Domain Arachaea (including, but not limited to, archaebacteria), which have begun to be used in recombinant nucleic acid work, members of the phylum Protista, or other cell of the algae, fungi, or any cell of the animal or plant kingdoms.

Plant cells useful in expressing polypeptides of use in assays of the invention include, but are not limited to, tobacco (*Nicotiana plumbaginifolia* and *Nicotiana tabacum*), arabidopsis (*Arabidopsis thaliana*), *Aspergillus niger*, *Brassica napus*, *Brassica nigra*, *Datura innoxia*, *Vicia narbonensis*, *Vicia faba*, pea (*Pisum sativum*), cauliflower, carnation and lentil (*Lens culinaris*). Either whole plants, cells or protoplasts may be transfected with a nucleic acid of choice. Methods for plant cell transfection or stable transformation include inoculation with *Agrobacterium tumefaciens* cells carrying the construct of interest (see, among others, Turpen et al., 1993, *J. Virol. Methods*, 42: 227–239), administration of liposome-associated nucleic acid molecules (Maccarrone et al., 1992, *Biochem. Biophys. Res. Commun.*, 186: 1417–1422) and microparticle injection (Johnston and Tang, 1993, *Genet. Eng. (N.Y.)*, 15: 225–236), among other methods. A generally useful plant transcriptional control element is the cauliflower mosaid virus (CaMV) 35S promoter (see, for example, Saalbach et al., 1994, *Mol. Gen. Genet.*, 242: 226–236). Non-limiting examples of nucleic acid vectors useful in plants include pGSGLUC1 (Saalbach et al., 1994, supra), pGA492 (Perez et al., 1989, *Plant Mol. Biol.*, 13: 365–373), pOCA18 (Olszewski et al., 1988, *Nucleic Acids Res.*, 16: 10765–10782), the Ti plasmid (Roussell et al., 1988, *Mol. Gen. Genet.*, 211: 202–209) and pKR612B1 (Balazs et al., 1985, *Gene*, 40: 343–348).

Mammalian cells are of use in the invention. Such cells include, but are not limited to, neuronal cells (those of both primary explants and of established cell culture lines) cells of the immune system (such as T-cells, B-cells and macrophages), fibroblasts, hematopoietic cells and dendritic cells. Using established technologies, stem cells (e.g. hematopoietic stem cells) may be used for gene transfer after enrichment procedures. Alternatively, unseparated hematopoietic cells and stem cell populations may be made susceptible to DNA uptake. Transfection of hematopoietic stem cells is described in Mannion-Henderson et al., 1995, *Exp. Hematol.*, 23: 1628; Schiffmann et al., 1995, *Blood*, 86: 1218; Williams, 1990, *Bone Marrow Transplant*, 5: 141; Boggs, 1990, *Int. J. Cell Cloning*, 8: 80; Martensson et al., 1987, *Eur. J. Immunol.*, 17: 1499; Okabe et al., 1992, *Eur. J. Immunol.*, 22: 37–43; and Banerji et al., 1983, *Cell*, 33: 729. Such methods may advantageously be used according to the present invention.

ii. Nucleic Acid Vectors for the Expression of Assay Components of the Invention in Cells or Multicellular Organisms A nucleic acid of use according to the methods of the invention may be either double- or single stranded and either naked or associated with protein, carbohydrate, proteoglycan and/or lipid or other molecules. Such vectors may contain modified and/or unmodified nucleotides or ribonucleotides. In the event that the gene to be transfected may be without its native transcriptional regulatory sequences, the vector must provide such sequences to the gene, so that it can be expressed once inside the target cell. Such sequences may direct transcription in a tissue-specific manner, thereby limiting expression of the gene to its target cell population, even if it is taken up by other surrounding cells. Alternatively, such sequences may be general regulators of transcription, such as those that regulate housekeeping genes, which will allow for expression of the transfected gene in more than one cell type; this assumes that the majority of vector molecules will associate preferentially with the cells of the tissue into which they were injected, and that leakage of the vector into other cell types will not be significantly deleterious to the recipient mammal. It is also possible to design a vector that will express the gene of choice in the target cells at a specific time, by using an inducible promoter, which will not direct transcription unless a specific stimulus, such as heat shock, is applied.

A gene encoding a component of the assay system of the invention or a candidate modulator of protein-modifying enzyme activity may be transfected into a cell or organism using a viral or non-viral DNA or RNA vector, where non-viral vectors include, but are not limited to, plasmids, linear nucleic acid molecules, artificial chromomosomes and episomal vectors. Expression of heterologous genes in mammals has been observed after injection of plasmid DNA into muscle (Wolff J. A. et al., 1990, *Science*, 247: 1465–1468; Carson D. A. et al., U.S. Pat. No. 5,580,859), thyroid (Sykes et al., 1994, *Human Gene Ther.*, 5: 837–844), melanoma (Vile et al., 1993, *Cancer Res.*, 53: 962–967), skin (Hengge et al., 1995, *Nature Genet.*, 10: 161–166), liver (Hickman et al., 1994, *Human Gene Therapy*, 5: 1477–1483) and after exposure of airway epithelium (Meyer et al., 1995, *Gene Therapy*, 2: 450–460).

In addition to vectors of the broad classes described above and the polypeptide comprising a coiled-coil/fluorescent protein fusion gene expression constructs described above (see "Fluorescent resonance energy transfer"), microbial plasmids, such as those of bacteria and yeast, are of use in the invention.

Bacterial Plasmids:

Of the frequently used origins of replication, pBR322 is useful according to the invention, and pUC is preferred. Although not preferred, other plasmids which are useful according to the invention are those which require the presence of plasmid encoded proteins for replication, for example, those comprising pT181, FII, and FI origins of replication.

Examples of origins of replication which are useful in assays of the invention in *E. coli* and *S. typhimurium* include but are not limited to, pHETK (Garapin et al., 1981, *Proc. Natl. Acad. Sci. U.S.A.*, 78: 815–819), p279 (Talmadge et al., 1980, *Proc. Natl. Acad. Sci. U.S.A.*, 77: 3369–3373), p5–3 and p21A-2 (both from Pawalek et al., 1997, *Cancer Res.*, 57: 4537–4544), pMB1 (Bolivar et al., 1977, *Gene*, 2: 95–113), ColE1 (Kahn et al., 1979, *Methods Enzymol.*, 68: 268–280), p15A (Chang et al., 1978, *J. Bacteriol.*, 134: 1141–1156); pSC101 (Stoker et al., 1982, *Gene*, 18: 335–341); R6K (Kahn et al., 1979, supra); R1 (temperature dependent origin of replication, Uhlin et al., 1983, *Gene*, 22: 255–265); lambda dv (Jackson et al., 1972, *Proc. Nat. Aca. Sci. U.S.A.*, 69: 2904–2909); pYA (Nakayama et al., 1988, infra). An example of an origin of replication that is useful in Staphylococcus is pT181 (Scott, 1984, *Microbial Reviews* 48: 1–23). Of the above-described origins of replication, pMB1, p15A and ColE1 are preferred because these origins do not require plasmid-encoded proteins for replication.

Yeast Plasmids:

Three systems are used for recombinant plasmid expression and replication in yeasts:

1. Integrating. An example of such a plasmid is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells. Regardless of the type of plasmid used, yeast cells are typically transformed by chemical methods (e.g. as described by Rose et al., 1990, *Methods Yeast Genetics*, Cold Spring Harbor Laboratory Press, Cold Spring Harbor, N.Y.). The cells are treated with lithium acetate to achieve transformation efficiencies of approximately $10^4$ colony-forming units (transformed cells)/µg of DNA. Yeast perform homologous recombination such that the cut, selectable marker recombines with the mutated (usually a point mutation or a small deletion) host gene to restore function. Transformed cells are then isolated on selective media.

2. Low copy-number ARS-CEN, of which YCp is an example. Such a plasmid contains the autonomous replicating sequence (ARS1), a sequence of approximately 700 bp which, when carried on a plasmid, permits its replication in yeast, and a centromeric sequence (CEN4), the latter of which allows mitotic stability. These are usually present at 1–2 copies per cell. Removal of the CEN sequence yields a YRp plasmid, which is typically present in 100–200 copes per cell; however, this plasmid is both mitotically and meiotically unstable.

3. High-copy-number 2µ circles. These plasmids contain a sequence approximately 1 kb in length, the 2µ sequence, which acts as a yeast replicon giving rise to higher plasmid copy number; however, these plasmids are unstable and require selection for maintenance. Copy number is increased by having on the plasmid a selection gene operatively linked to a crippled promoter. This is usually the LEU2 gene with a truncated promoter (LEU2-d), such that low levels of the Leu2p protein are produced; therefore, selection on a leucine-depleted medium forces an increase in copy number in order to make an amount of Leu2p sufficient for cell growth.

As suggested above, examples of yeast plasmids useful in the invention include the YRp plasmids (based on autonomously-replicating sequences, or ARS) and the YEp plasmids (based on the 2µ circle), of which examples are YEp24 and the YEplac series of plasmids (Gietz and Sugino, 1988, *Gene*, 74: 527–534). (See Sikorski, "Extrachromsomoal cloning vectors of *Saccharomyces cerevisiae*", in *Plasmids, A Practical Approach*, Ed. K. G. Hardy, IRL Press, 1993; and *Yeast Cloning Vectors and Genes, Current Protocols in Molecular Biology*, Section II, Unit 13.4, Eds., Ausubel et al., 1994).

In addition to a yeast origin of replication, yeast plasmid sequences typically comprise an antibiotic resistance gene, a bacterial origin of replication (for propagation in bacterial cells) and a yeast nutritional gene for maintenance in yeast cells. The nutritional gene (or "auxotrophic marker") is most often one of the following (with the gene product listed in parentheses and the sizes quoted encompassing the coding sequence, together with the promoter and terminator elements required for correct expression):

TRP1 (PhosphoADP-ribosylanthranilate isomerase, which is a component of the tryptophan biosynthetic pathway).

URA3 (Orotidine-5'-phosphate decarboxylase, which takes part in the uracil biosynthetic pathway).

LEU2 (3-Isopropylmalate dehydrogenase, which is involved with the leucine biosynthetic pathway).

HIS3 (Imidazoleglycerolphosphate dehydratase, or IGP dehydratase).

LYS2 (α-aminoadipate-semialdehyde dehydrogenase, part of the lysine biosynthetic pathway).

Alternatively, the screening system may operate in an intact, living multicellular organism, such as an insect or a mammal. Methods of generating transgenic *Drosophila*, mice and other organisms, both transiently and stably, are well known in the art; detection of fluorescence resulting from the expression of Green Fluorescent Protein in live *Drosophila* is well known in the art. One or more gene expression constructs encoding one or more of a labeled polypeptide comprising a coiled-coil, a protein-modifiying enzyme and, optionally, a candidate modulator thereof are introduced into the test organism by methods well known in the art (see also below). Sufficient time is allowed to pass after administration of the nucleic acid molecule to allow for gene expression, for dimerization of polypeptides comprising a coiled-coil and for chromophore maturation, if necessary (e.g., Green Fluorescent Protein matures over a period of approximately 2 hours prior to fluorescence) before FRET is measured. A reaction component (particularly a candidate modulator of enzyme function) which is not administered as a nucleic acid molecule may be delivered by a method selected from those described below.

Alternative Fluorescence Output—Monomer:Excimer Fluorescence

Figure 3:
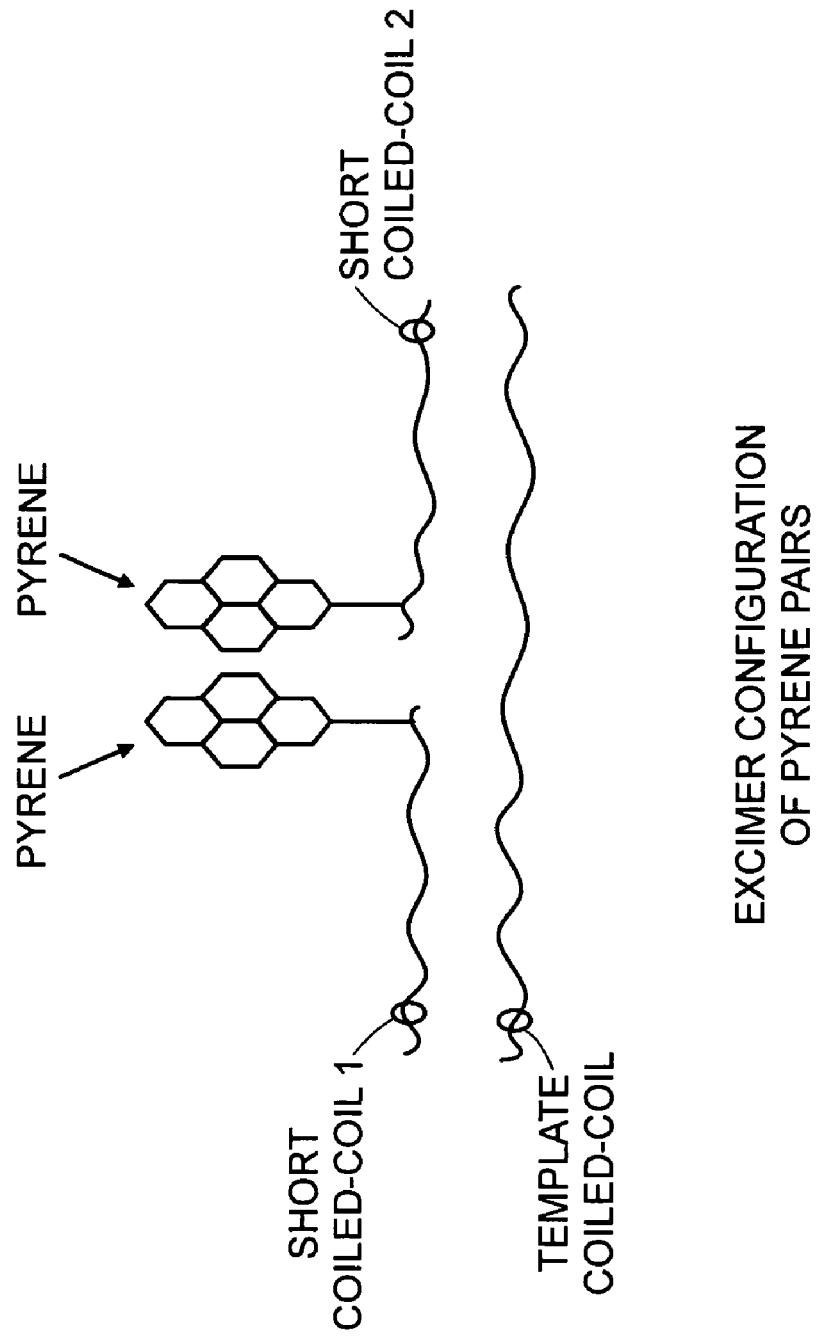

A second embodiment of the technology can utilize monomer:excimer fluorescence as the output. The assembly of polypeptides comprising a coiled-coil motif in this format is shown in FIG. 3.

The fluorophore pyrene when present as a single copy displays fluorescent emission of a particular wavelength significantly shorter than when two copies of pyrene form a planar dimer (excimer), as depicted. As above, excitation at a single wavelength (probably 340 nm) is used to review the excimer fluorescence (~470 nm) over monomer fluorescence (~375 nm) to quantify assembly:disassembly of the reporter molecule.

Dosage and Administration of a Labeled Polypeptide Comprising a Coiled-Coil, Protein-Modifying Enzyme or Candidate Modulator Thereof for use in an in vivo assay of the invention i. Dosage When the amount of a protein, nucleic acid or other agent to be administered to a test cell or animal is considered, it will be apparent to those of skill in the art that the effective amount of a composition administered in the invention will depend, inter alia, upon the efficiency of cellular uptake of a composition, the administration schedule, the unit dose administered, whether the compositions are administered in combination with other agents, the health of the recipient, and the biological activity of the particular composition.

The precise amount of a protein, nucleic acid or agent to be delivered as a component of an assay system of the invention (and/or, if an effective modulator of enzymatic activity is uncovered, administered to an organism, such as a human, in which it is desired to modulate the activity of the enzyme influenced by that modulator) depends on the judgment of one of skill in the art and may be peculiar to each subject or cell-based test system, within a limited range of values. For example, the amount of each labeled polypeptide species comprising a coiled-coil must fall within the detection limits of the fluorescence-measuring device employed. The amount of an enzmye or candidate modulator thereof will typically be in the range of about 1 µg–100 mg/kg body weight. Where the candidate modulator is a peptide or polypeptide, it is typically administered in the range of about 100–500 µg/ml per dose. A single dose of a candidate modulator, or multiple doses of such a substance, daily, weekly, or intermittently, is contemplated according to the invention.

A candidate modulator is tested in a concentration range that depends upon the molecular weight of the molecule and the type of assay. For example, for inhibition of protein/protein or protein/DNA complex formation or transcription initiation (depending upon the level at which the candidate modulator is thought or intended to modulate the activity of a protein-modifying enzyme according to the invention), small molecules (as defined above) may be tested in a concentration range of 1 pg–100 µg/ml, preferably at about 100 pg–10 ng/ml; large molecules, e.g., peptides, may be tested in the range of 10 ng–100 µg/ml, preferably 100 ng–10 µg/ml.

Generally, nucleic acid molecules are administered in a manner compatible with the dosage formulation, and in such amount as will be effective. In the case of a recombinant nucleic acid comprising a labeled polypeptide comprising a coiled-coil, such an amount should be sufficient to result in production of a detectable amount of the labeled protein or peptide, as discussed above. In the case of a modifying enzyme, the amount produced by expression of a nucleic acid molecule should be sufficient to ensure that at least 10% of coiled-coils will undergo modification if they comprise a target site recognized by the enzyme being assayed. Lastly, the amount of a nucleic acid encoding a candidate modulator of a modifying enzyme of the invention must be sufficient to ensure production of an amount of the candidate modulator which can, if effective, produce a change of at least 10% in the effect of the target modifying enzyme on FRET resulting from dimerization of coiled-coils comprised by polypeptides comprising a coiled-coil or, if administered to a patient, an amount which is prophylactically and/or therapeutically effective.

When the end product (e.g. an antisense RNA molecule or ribozyme) is administered directly, the dosage to be administered is directly proportional to the amount needed per cell and the number of cells to be transfected, with a correction factor for the efficiency of uptake of the molecules. In cases in which a gene must be expressed from the nucleic acid molecules, the strength of the associated transcriptional regulatory sequences also must be considered in calculating the number of nucleic acid molecules per target cell that will result in adequate levels of the encoded product. Suitable dosage ranges are on the order of, where a gene expression construct is administered, 0.5- to 1 µg, or 1–10 µg, or optionally 10–100 µg of nucleic acid in a single dose. It is conceivable that dosages of up to 1 mg may be advantageously used. Note that the number of molar equivalents per cell vary with the size of the construct, and that absolute amounts of DNA used should be adjusted accordingly to ensure adequate gene copy number when large constructs are injected.

If no effect (e.g., of a modifying enzyme or an inhibitor thereof) is seen within four orders of magnitude in either direction of the starting dosage, it is likely that a modifying enzyme does not recognize the target site present on the coiled-coils comprised by polypeptides comprising a coiled-coil according to the invention, or that the candidate modulator thereof is not of use according to the invention. It is critical to note that when high dosages are used, the concentration must be kept below harmful levels, which may be known if an enzyme or candidate modulator is a drug that is approved for clinical use. Such a dosage should be one (or, preferably, two or more) orders of magnitude below the $LD_{50}$ value that is known for a laboratory mammal, and preferably below concentrations that are documented as producing serious, if non-lethal, side effects. If it is determined that an enzyme or candidate modulator is optimally useful at levels that are harmful if achieved systemically, that agent should be used for local administration only, and then only at such doses where diffusion of the agent from the target site reduces its concentration to safe levels.

ii. Administration

Components of screening assays of the invention may be formulated in a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art. Administration of labeled polypeptides comprising coiled-coils, a protein-modifying enzyme or a candidate modulator as described herein may be either localized or systemic.

Localized Administration:

It is contemplated that global administration of a component of an assay system of the invention to an animal is not needed in order to achieve a highly localized effect. Localized administration of a nucleic acid is preferably by via injection or by means of a drip device, drug pump or drug-saturated solid matrix from which the nucleic acid can diffuse implanted at the target site. When a tissue that is the target of delivery according to the invention is on a surface of an organism, topical administration of a pharmaceutical composition is possible. For example, antibiotics are commonly applied directly to surface wounds as an alternative to oral or intravenous administration, which methods necessitate a much higher absolute dosage in order to counter the effect of systemic dilution, resulting both in possible side-effects in otherwise unaffected tissues and in increased cost.

Compositions comprising a composition of- or of use in the invention which are suitable for topical administration can take one of several physical forms, as summarized below:

(i) A liquid, such as a tincture or lotion, which may be applied by pouring, dropping or "painting" (i.e. spreading manually or with a brush or other applicator such as a spatula) or injection.

(ii) An ointment or cream, which may be spread either manually or with a brush or other applicator (e.g. a spatula), or may be extruded through a nozzle or other small opening from a container such as a collapsible tube.

(iii) A dry powder, which may be shaken or sifted onto the target tissue or, alternatively, applied as a nebulized spray.

(iv) A liquid-based aerosol, which may be dispensed from a container selected from the group that comprises pressure-driven spray bottles (such as are activated by squeezing), natural atomizers (or "pump-spray" bottles that work without a compressed propellant) or pressurized canisters.

(v) A carbowax or glycerin preparation, such as a suppository, which may be used for rectal or vaginal administration of a therapeutic composition.

In a specialized instance, the tissue to which a candidate modulator of a modifying enzyme is to be delivered for assay (or, if found effective, for therapeutic use) is the lung. In such a case the route of administration is via inhalation, either of a liquid aerosol or of a nebulized powder of. Drug delivery by inhalation, whether for topical or systemic distribution, is well known in the art for the treatment of asthma, bronchitis and anaphylaxis. In particular, it has been demonstrated that it is possible to deliver a protein via aerosol inhalation such that it retains its native activity in vivo (see Hubbard et al., 1989, *J. Clin. Invest.*, 84: 1349–1354).

Systemic Administration:

Systemic administration of a protein, nucleic acid or other agent according to the invention may be performed by methods of whole-body drug delivery are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a-reservoir of exogenously-produced protein, nucleic acid or other material or may, instead, comprise cells that produce and secrete a polypeptide comprising a coiled-coil, protein-modifying enzyme or candidate modulator thereof. Note that injection may be performed either by conventional means (i.e. using a hypodermic needle) or by hypospray (see Clarke and Woodland, 1975, *Rheumatol Rehabil*, 14: 47–49).

Systemic administration is advantageous when the components of an assay system of the invention must be delivered to a target tissue that is widely-dispersed, inaccessible to direct contact or, while accessible to topical or other localized application, is resident in an environment (such as the digestive tract) wherein the native activity of the protein, nucleic acid or other agent might be compromised, e.g. by digestive enzymes or extremes of pH.

Components of assays of the invention, but particularly candidate modulators to be screened according to the invention, can be given in a single- or multiple dose. A multiple dose schedule is one in which a primary course of administration can include 1–10 separate doses, followed by other doses given at subsequent time intervals required to maintain and or reinforce the cellular level of the transfected nucleic acid. Such intervals are dependent on the continued need of the recipient for the candidate modulator; in the case of a nucleic acid molecule, its ability to self-replicate in a test cell if it does not become integrated into the recipient's genome and the half-life of a non-renewable nucleic acid (e.g. a molecule that will not self-replicate) are important factors to consider.

Delivery of a nucleic acid may be performed using a delivery technique selected from the group that includes, but is not limited to, the use of viral vectors and non-viral vectors, such as episomal vectors, artificial chromosomes, liposomes, cationic peptides, tissue-specific cell transfection and transplantation, administration of genes in general vectors with tissue-specific promoters, etc.

EXAMPLE 1

"Use of a Polypeptide Comprising a Coiled-Coil as a Phosphorylation Reporter According to the Invention a. Peptide modified by chemical phosphorylation Zip 3, a polypeptide which comprises a leucine zipper motif and which has a phosphorylation site in the center of the molecule, has the following amino acid sequence:

R MKQLEDK VEELLSK TYHLENE VACLKKL VGERAAK (SEQ ID NO. 27)

This sequence is derived from that of amino acids 249–281 of GCN4 (Genbank Accession No. K02205; the sequence AAK has been added to the C-terminus of that polypeptide sequence, $N_{264}$ has been changed to T and $R_{273}$ has been changed to C. The threonine residue (shown here in bold type) is the residue which is to be phosphorylated. The cysteine residue (also shown in bold type) provides the site for attachment of thiol-directed fluorescent labels. Spaces in the sequence separate the heptad motifs (a, b, c, d, e, f and g, repeated). In other experiments presented below, this sequence was adapted to contain the recognition motif for protein kinase A (PKA), positioned such that the threonine residue could be enzymatically phosphorylated. This was accomplished while still preserving the leucine zipper structure."

Figure 4:
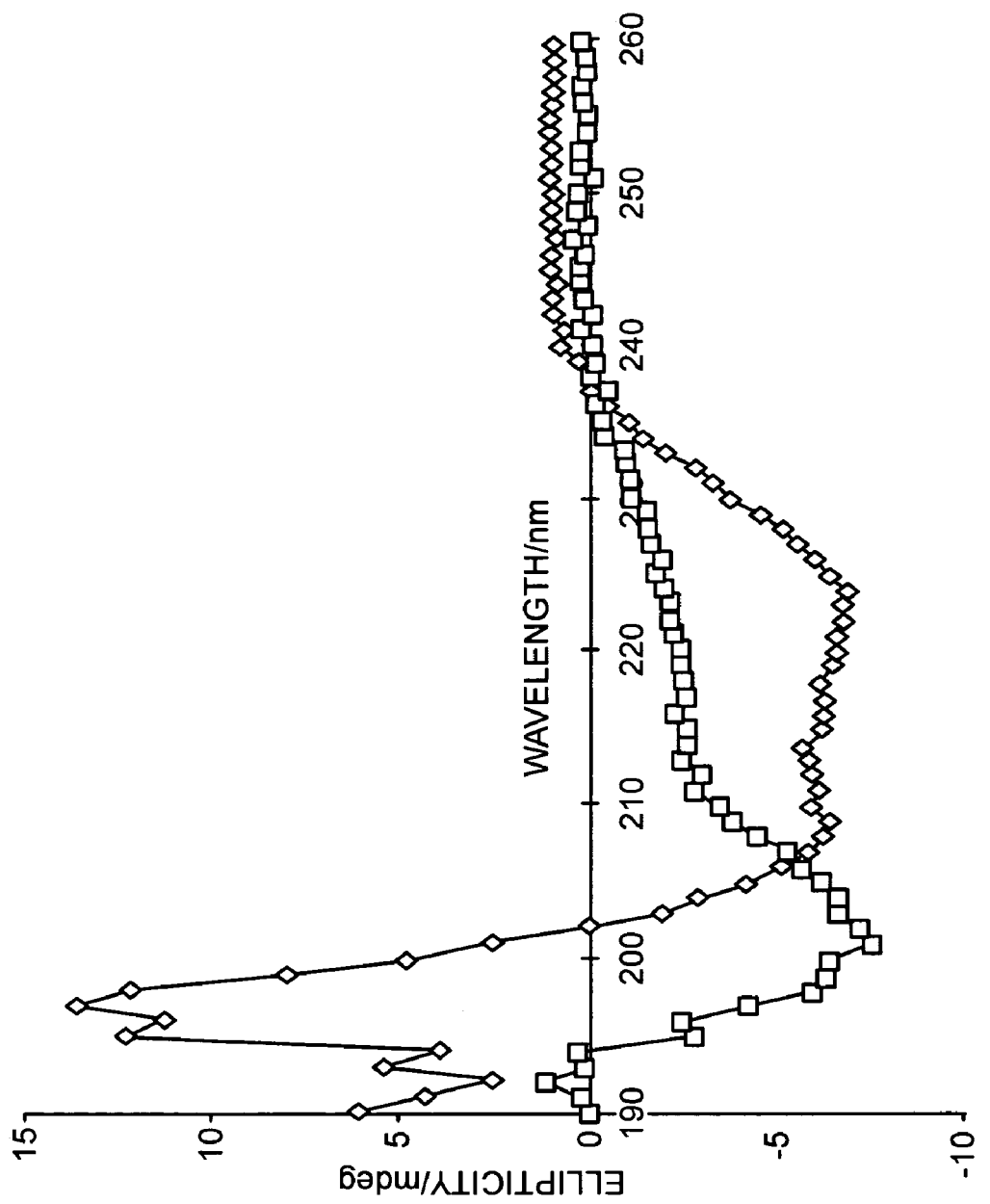
Figure 5:
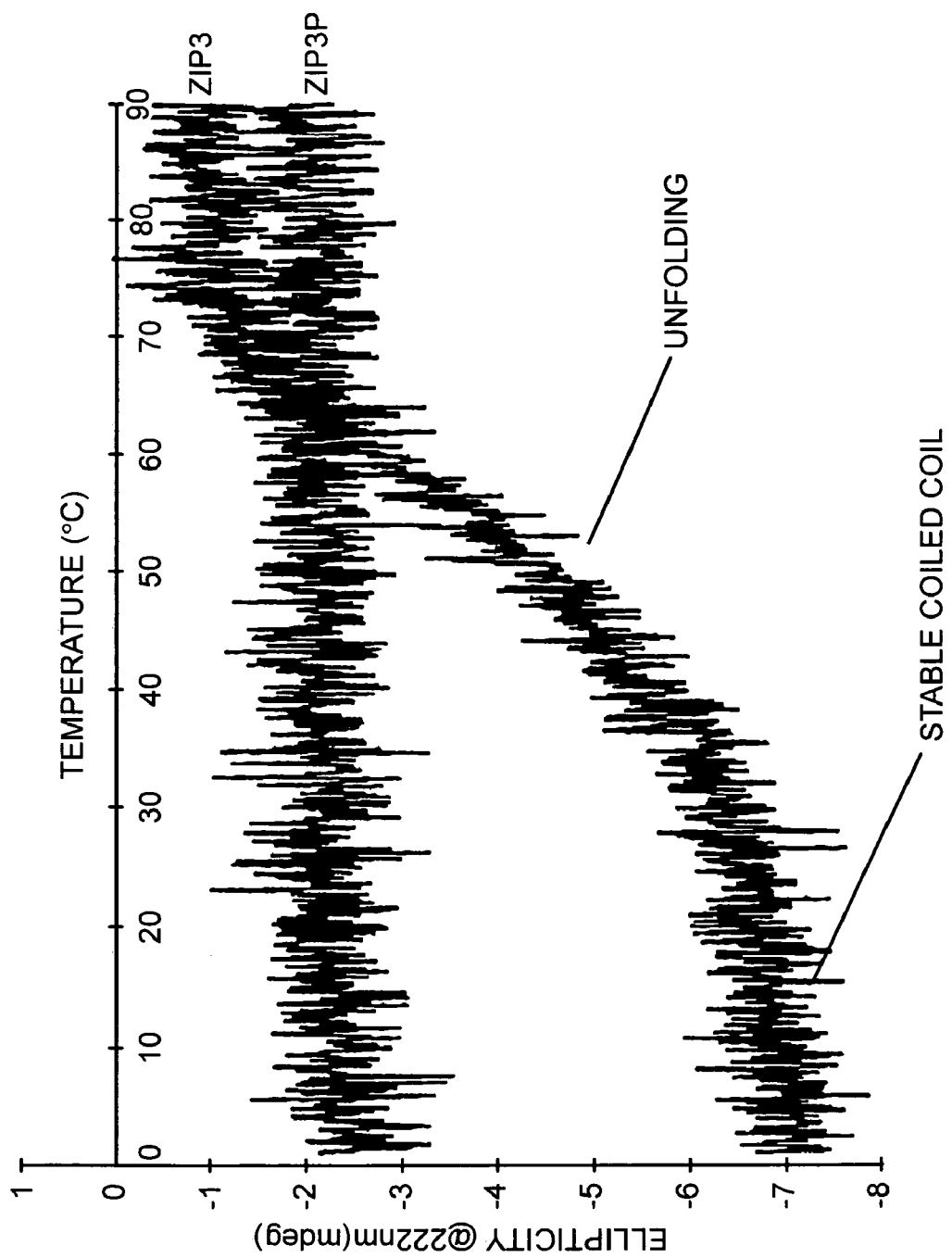
FIG. 5 shows thermal melting of Zip3 and Zip3P. Ellipticity at 222 nm is shown in mdeg on the y-axis, while temperature in ° C. is shown on the x-axis.

FIGS. 4 and 5 present data showing that phosphorylation of Zip3 at the central threonine residue destabilized the coiled-coil structure. The experiments may be summarized as follows:

The circular dichroism (measured in units of ellipticity) of proteins at 222 nm provides a measure of the amount of α-helix present in the structure, with a large, negative ellipticity indicting a high level of helicity. The coiled-coil has a distinctive α-helical CD spectrum with minima at 222 nm and 208 nm (O'Shea et al., 1989, *Science*, 243: 538–542). The CD spectra of the unmodified Zip3 and its phosphorylated form (Zip3P) were determined at a sample concentration of 10 µM in 150 mM KCl, 42.2 mM $K_2HPO_4$, 7.8 mM $KH_2PO_4$, pH 7.0 at 20° C.; spectra were recorded in a 1 mm pathlength cell in a Jasco J-715 spectropolarimeter with a Jasco PTC-348W Peltier temperature control unit. In all experiments described herein, peptide concentration was determined by tyrosine absorbance at 280 nm in 6M GuHCl. The results are shown in FIG. 4. The spectrum of Zip3 which was observed was that of a classic coiled-coil (O'Shea et al., 1989, supra), while that of Zip3P produced by was indicative of random coil, unfolded. As shown in FIG. 5, the ellipticity of Zip3 and Zip3P at 222 nm with increasing temperature was measured. The steep portion of the sigmoid curve seen for Zip3 indicated the unfolding of the molecule. It is clear that this leucine zipper peptide began to unfold at around 35° C. and was completely unfolded by 70° C. The ellipticity of Zip3P fluctuated around a small negative value, suggesting that this structure was unfolded even at the starting temperature of 1° C. and remained unfolded at all temperatures considered.

Peptides were then labeled using a method adapted from one known in the art (Hermanson, 1997, *Bioconjugate Techniques*, Academic Press). 20 mM fluorescein iodoacetamide (FAM) in DMSO and 0.23 mM peptide in 20 mM TES buffer, pH 7.0 were prepared. These were mixed in a molar ratio of 0.9:1 (peptide:label) and incubated at 4° C. in the dark for a minimum of 2 hours. Initially, this method was also applied to labelling with rhodamine maleimide at a ratio of 0.9:2; however, in other experiments, good labelling has been obtained using rhodamine iodoacetamide at a ratio of 0.9:1. Labelling was assessed by reverse phase HPLC (C18 column; solvent A: $H_2O$/0.1% TFA; solvent B: acetonitrile/0.1% TFA) and MALDI-TOF mass spectrometry. Zip3 peptides labeled with fluorescein (Zip3F) and rhodamine (Zip3R) were thus generated.

Figure 6:
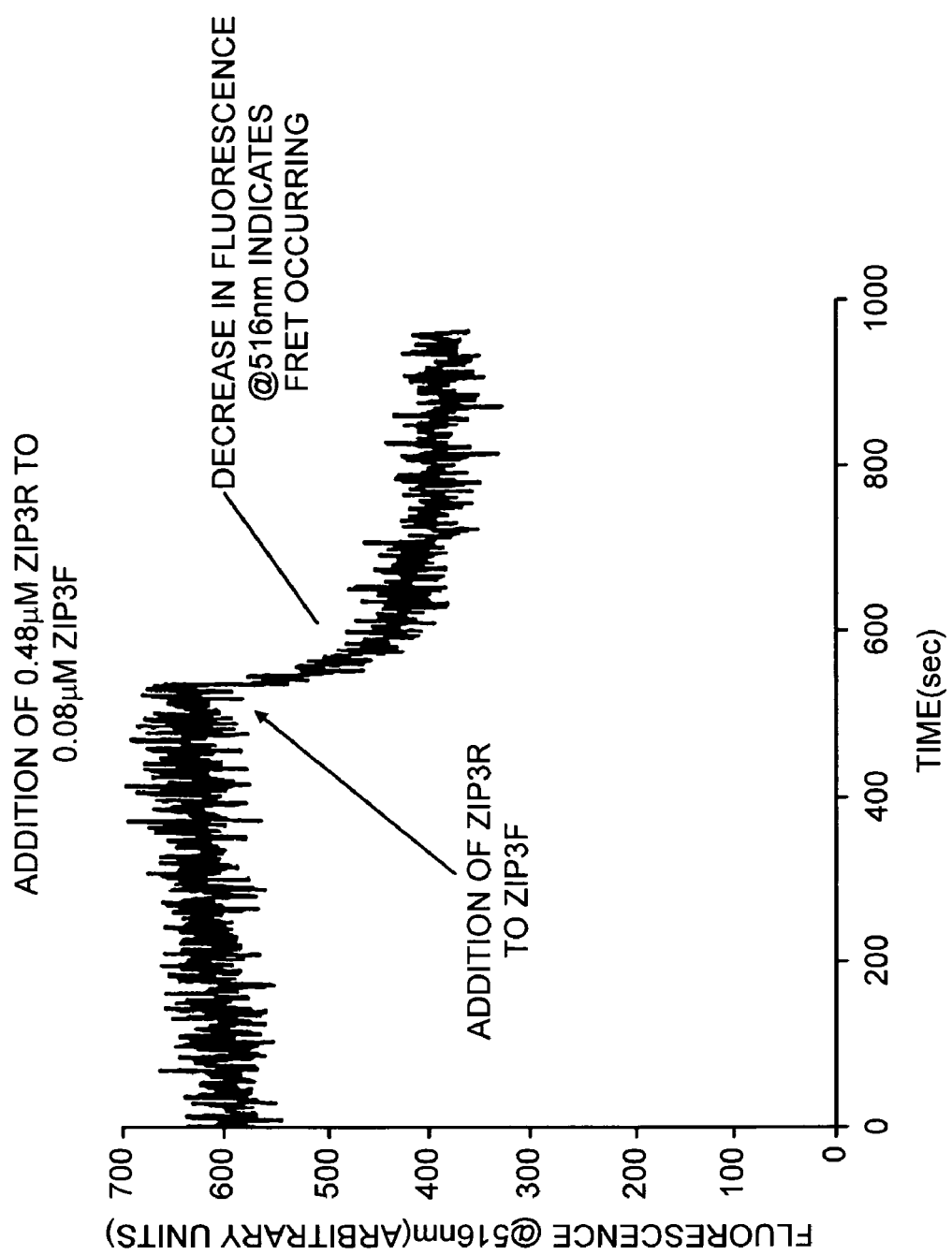
FIG. 6 shows the effect of the addition of 0.48 µM Zip3R to 0.08 µM Zip3F. Fluorescence at 516 nm is shown on the y-axis; time in seconds is charted on the x-axis.
Figure 7:
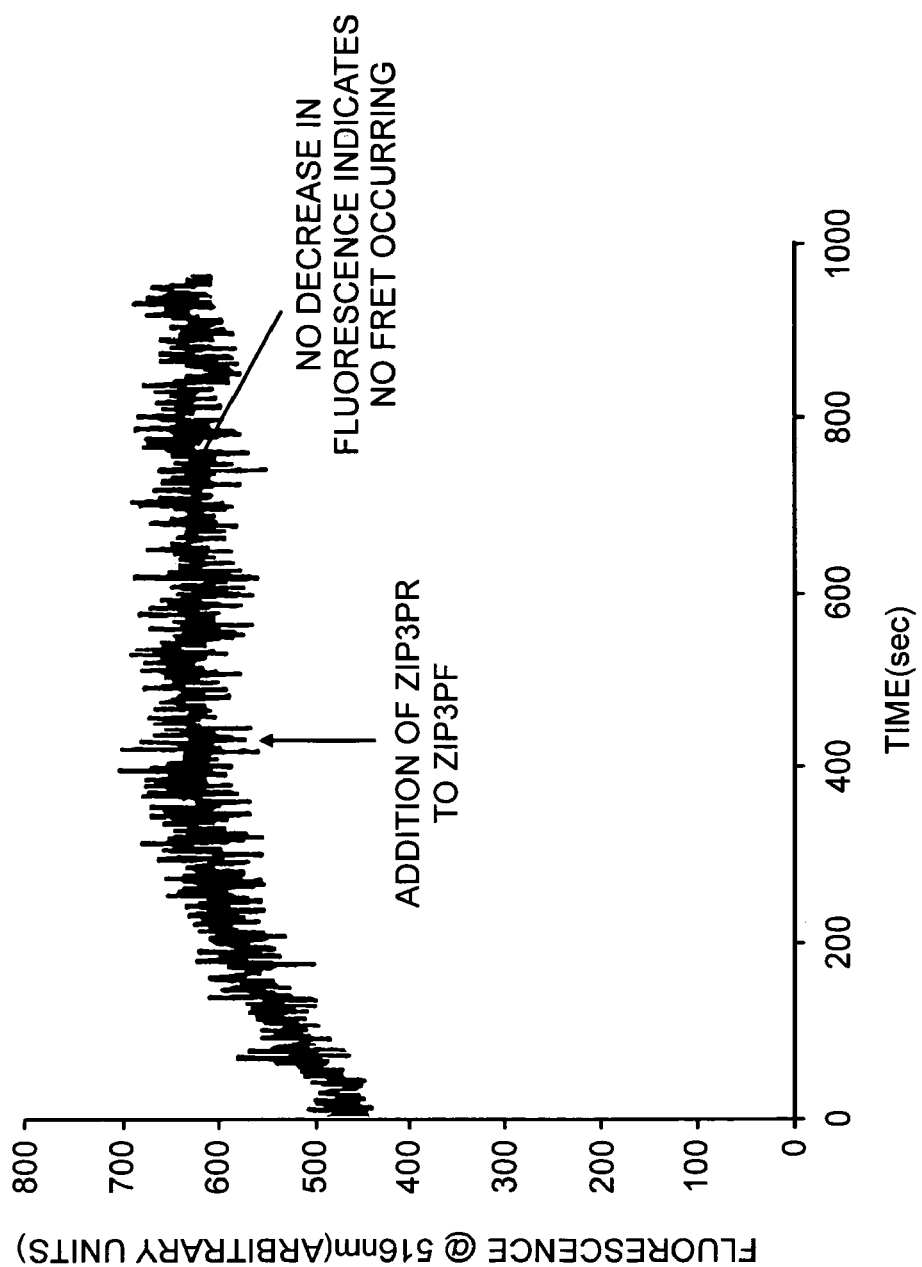
FIG. 7 shows the effect of the addition of 0.48 µM Zip3PR to 0.08 µM Zip3PF. Fluorescence at 516 nm is shown on the y-axis; time in seconds is charted on the x-axis.

The data presented in FIGS. 6 and 7 demonstrate that FRET occurs between fluorophores attached to unphosphorylated peptides, which interact with each other, but not between phosphorylated peptides, which do not interact (evidenced by loss of structure in CD experiments; see FIG. 4). Only the fluorescence emission quench of the donor fluorophore is displayed in these figures.

Fluorescence at 516 nm was measured for labeled Zip3 proteins in a 1 cm pathlength cell at peptide concentrations of 0.08 µM Zip3F and 0.48 µM Zip3R in 50 mM KCl, 42.2 mM $K_2HPO_4$, 7.8 mM $KH_2PO_4$, pH 7.0 at 37° C. in a PTI fluorimeter system with temperature controlled by a waterbath. Upon addition of Zip3R to Zip3F, fluorescence in the region of fluorescein emission decreased. This was accompanied by an increase in fluorescence detected in the rhodamine emission region (not shown). These data suggest that energy transfer was taking place and that some of the energy emitted by the fluorescein was directly exciting the rhodamine label on the partner peptide. The fluorescence at 516 nm showed no decrease upon addition of Zip3PR (the phosphorylated form of Zip3R, added at time 500 seconds) to Zip3PF (the phosphorylated form of Zip3F) (FIG. 7). In addition, no FRET was observed when Zip3F was mixed with Zip3PR (not shown), indicating that when even one peptide partner is phosphorylated, formation of the coiled-coil structure and, hence, protein:protein heterodimerization (with respect to fluorophore composition), cannot occur.

Together, these results, that FRET did not occur between the phosphorylated molecules or between a phosphorylated and an unphosphorylated molecule, indicated that FRET using labeled, polypeptides comprising a coiled-coil, may be used successfully in the invention to report on the phosphorylation state of peptides.

EXAMPLE 2

Assaying the Activity of a Protein Modifying Enzyme According to the Invention

In Example 1, the suitability of fluorescently labeled, non-naturally-occurring polypeptides comprising a coiled-coil as reporters on protein phosphorylation using FRET was demonstrated. In the present Example, the tailoring of such peptides to render them functional reporters of enzymatic activity of a protein modifying enzyme (in this case, a protein kinase) is illustrated.

"Peptide Modified by Enzymatic phorphorylation

Two variants of the peptide Zip4 (derived from amino acids 249–281 of GCN4; Genbank Accession No. K02205) were synthesized. The amino acid sequence of these peptides (Zip4S and Zip4T) were as follows:

R MKQLEDQ VRRLRRK SYHLENE VACLKKL VGERAAK (SEQ ID NO. 28) (as Zip3, but also $E_{258} \to R$, $E_{259} \to R$, $L_{261} \to R$, $S_{262} \to R$ and $N_{264} \to S$), and R MKQLEDQ VRRLRRK TYHLENE VACLKKL VGERAAK (SEQ ID NO. 29) (as Zip4S, but $N_{264} \to T$).

The italicized arginine residues form the recognition site for PKA (Pearson and Kemp, 1991, *Methods Enzymol.*, 200: 62–81)."

A timecourse of phosphorylation of these peptides by PKA was run in 50 mM histidine/HCl (pH 7.0), 5 mM $MgSO_4$, 5 mM NaF, 0.05 mM EGTA, 120 mM KCl with 0.2 mM ATP (30.9 cpm/pmol $^{32}$P-ATP) and 0.5 µM PKA. The results, presented in FIG. 8, showed that Zip 4S is a good substrate for this enzyme, with a rate of phosphorylation comparable to that seen with a known substrate (PL919Y, a phospholamban peptide; Drago and Colyer, 1994, *J. Biol. Chem.*: 269: 25073–25077). Zip4T is also phosphorylated, but at a slower rate, with full phosphorylation achieved in 30 minutes in this assay. In this assay, the difference in cpm recovered between the Zip4 peptides and PL919Y was due to the difference in recovery of these peptides on P81 paper; however, a plateau was taken to indicate full phosphorylation.

A second set of timecourses of phosphorylation was performed on Zip4S using PKA and $Ca^{2+}$/Calmodulin-dependent Protein Kinase (CaMKII), together with positive and negative controls for CaMKII (used to confirm that the crude preparation of CaMKII had the expected characteristics of that enzyme). PKA phosphorylation was performed in 50 mM histidine/HCl (pH 7.0), 5 mM $MgSO_4$, 5 mM NaF, 0.05 mM EGTA, 120 mM KCl with 0.2 mM ATP (39.72 cpm/pmol $^{32}$P-ATP) and 0.25 µM PKA. CaMKII phosphorylation was performed in 50 mM histidine/HCl (pH 7.0), 5 mM $MgSO_4$, 5 mM NaF, 120 mM KCl, 0.5 mM $Ca^{2+}$, 0.037 mg/ml calmodulin with 0.2 mM ATP (39.72 cpm/pmol $^{32}$P-ATP) and 10% crude CaMKII. In the $Ca^{2+}$-free experiment, $Ca^{2+}$ was replaced by 0.05 mM EGTA. As shown in FIG. 9, the results indicated that the phosphorylation site in Zip4S was recognized only by C-PKA. CaMKII was unable to phosphorylate Zip4S, while PKA mediated complete phosphorylation of that protein. Such specificity of a modification site included in a polypeptide comprising a coiled-coil is critical for use of the invention in an intracellular environment.

As in Example 1, circular dichroism was used to assess the coiled-coil structure of the Zip4 polypeptides and the disruption of that structure by phosphorylation. Both of the Zip4 peptides were found to be less thermostable than Zip3 (FIG. 10) when assayed under the same condition (see above), which is likely due to the introduction of a positively charged region to form the PKA recognition site. Zip4T was more stable than was Zip4S (FIG. 10). Thermal denaturation, again performed as described above, of enzymatically phosphorylated Zip4S showed that this modification disrupted coiled-coil formation and led to an unfolded polypeptide in solution (FIG. 11). This was confirmed by the CD spectra of Zip4S and Zip4SP at 1° C. (FIG. 12).

Fluorescence was used to report on the phosphorylation status of these peptides (FIG. 13). A loss of emission at 516 nm was seen on addition of Zip4SR to Zip4SF, as FRET occurred when the differentially-labeled polypeptide comprising a coiled-coil partners were allowed to associate. Emission at around 575 nm also increased; while a large portion of this increase may have been attributable to direct excitation of the rhodamine label, the increase was consistently above that seen in the phosphorylated scan, suggesting that a small proportion of the increase was due to excitation by FRET. On addition of PKA, emission at 516 run returned to above the level produced by Zip4SF alone, while emission at 573 nm decreased slightly; this decrease accounted for the amount of FRET-derived emission which was lost. No loss of FRET was observed on addition of PKA in the absence of ATP (data not shown).

Calculation of the ratio of fluorescence output is important, particularly for in vivo applications, thereby avoiding error due to high local concentrations of reporter in the system and enhancing the ability to observe meaningful change. Initial inspection of the data in these experiments led to a calculation of the ratio of fluorescence outputs at 573 nm and 516 nm; as shown in FIG. 14, FRET is seen as an increase in the 573/516 nm ratio. A decrease was seen in the ratio following phosphorylation by PKA, although the value did not return to the baseline because of the contribution of the 573 nm emission caused by direct excitation of the rhodamine label.

These several results demonstrate the applicability of the invention to the assessment of enzymatic activity on a target site present for that enzyme on a coiled-coil of a polypeptide comprising a coiled-coil, and further indicate that Zip4S is a suitable molecule upon which to base an assay system of the invention.

"Initial Unsuccessful Trials

Two potential reporter peptides were synthesized. The first, Zip 1, had a PKA phosphorylation site at the C-terminus while the second, Zip2s had such a site at the N-terminus (underlined).

Zip 1: HMKQLEDKVEELLSKNYCLENEVRRLRRASFSLQ (SEQ ID NO.30)

Zip 2: RRIRRASIDKVEELKSKNYCLENEVARLKKLVGER (SEQ ID NO.31)

The characterization of these peptides aimed to answer a number of questions regarding their oligomeric state, their suitability as substrates for PKA and a relevant phosphatase and the ability of phosphorylation to disrupt any oligomers formed. A number of techniques were used to assess the oligomeric state of the peptides. MALDI-TOF and electrospray mass spectrometry both yielded no useful results. Analytical ultracentrifugation gave ambiguous data (later shown to be due to the fact that the peptide dimers were unstable at the temperature used for analysis). The most successful technique used was circular dicbroism (CD)."

The coiled-coil motif has a characteristic CD spectrum. As described above, measurement of circular dichroism is useful to distinguish monomeric polypeptides from oligomers and to assess the stability of the structure present, although the technique cannot give information regarding the number of monomers making up the coiled-coil structure. These peptides (Zip1 and Zip2) were shown to form stable coiled-coils only at low (<20° C.) temperatures. Importantly, these peptides shown only have 4.5 leucine zipper heptads, and the incomplete nature of the final heptad is likely to compromise the stability of the coiled-coil structure.

The peptides were both shown to be good substrates for PKA by reverse-phase HPLC and radioactive assay. Phosphorylated peptides were purified by HPLC and analysed by CD. The phosphorylation caused no significant change in the stability of the peptides, suggesting that neither peptide was likely to be useful as a reporter molecule. Attempts to dephosphorylate the peptides using protein phosphatase I were unsuccessful. Both peptides were successfully labeled separately with donor and acceptor fluorophores. FRET was not convincingly seen, most likely due to the unstable nature of dimers formed.

In summary, the positioning of a PKA phosphorylation site in the C-terminal one and a half heptads (target S in the 'a' position) or the N-terminal heptad (target S in the 'd' position) of a GCN4 peptide produces an unstable coiled-coil whose stability is not affected by phosphorylation of the target serine. These findings are consistent with the guidelines provided above for the placement of a protein modification site in a coiled-coil of a polypeptide comprising a coiled-coil used in an assay of the invention: Zip 2 has polar residues at 4 of 10 possible 'a' and 'd' positions (which renders it very unstable even before phosphorylation), has the phosphorylation site at a 'd' site (itself, a good design decision), but one which is outside of the central 3 heptads (thereby limiting the contribution to oligomer stability). Zip 1 incorporates two polar residues in the ten possible 'a' and 'd' positions, which destabilizes the dimer and, additionally, has its phosphorylation site outside of the three central heptads, although it is in an 'a' position. While not being bound by any theory, it is likely that the packing of the interface is less tight at these marginal heptads, and thus they are more tolerant of the altered chemistry (addition of a phosphate group in this case) than a would be comparable position in a central heptad.

EXAMPLE 3

"A peptide sequence shown below is based upon the p67$^{SRF}$ glycosylation acceptor site S-316 (Reason et al., 1992, supra) and the adaptor of that sequence, which have been modified to improve their compliance with a coiled-coil sequence pattern:
  abcdefg abcdefg abcdefg abcdefg abcdefg (SEQ ID NO.32)
  SAV SSADGTV LK (SEQ ID NO.33) p67$^{SRF}$ (313–324)
  IAALEQK IAALSAV SSDLGTV LKCLQQK IAAIEQK (SEQ ID NO.34) p67$^{SRF}$ (313–324), coiled-coil (Zip5).

In this peptide, the site of O-glycosylation is S-316 ('a' position of heptad3), and the reporter polypeptide (Zip 5) comprising a coiled-coil has had introduced a single change in p67 sequence ($D_{319} \rightarrow L$), plus has undergone an extension of its sequence which complies with the canonical coiled-coil sequence to complete five heptads. This reporter polypeptide comprising a coiled-coil motif is expected to form stable oligomers in the absence of a glycosylated serine, which is assessed by FRET between appropriate fluorophores attached to the single Cys residue (shown in bold) in each partner peptide. Appropriate chemical fluorophores are attached to the single Cys (e.g., fluorescein and tetramethyirhodamine). O-glycosylation of Zip5 occurs upon exposure of thie peptide to a source of a protein-modifying enzyme which mediates O-GlcNAcylation of peptides (e.g. uridine diphospho-N-acetylglucosamine: peptide b N-acetylglucosaminyltransferase) and the appropriate conditions (defined in Haltiwanger et al., 1990, *J. Biol. Chem.*, 265: 2563–2568) causes modification of the Ser residue shown in bold and, consequently, the dissociation of these polypeptides comprising coiled-coils and loss of FRET."

N-Linked Glosylation Assay

The N-glycosylation of Asn residues occurs within the consensus sequence NxS/T (where x is any residue other than Pro or Asp; Shakineshleman, 1996, supra) of the target protein post-translationally in the lumen of the endoplasmic reticulum and golgi apparatus, hence limiting the identity of substrate proteins to those destined for secretion and those which are bound for the cell surface or another organelle in the cell.

"The coiled-coil structure readily accommodates the sequence NxS or NxT; for example, the N residue to be labeled is placed in the 'a' position of heptad 3. Thus, a candidate coiled-coil sequence modified from that of GCN4 peptide p1 (amino acids 249–280, Genbank Accession No. K02205, plus the C-terminal extension LEQK (SEQ ID NO.35)),
  R MKQLEDK VEELLSK NYSLENE VACLKKL VGELEQK (SEQ ID NO.36)
  R MKQLEDK VEELLSK NYTLENE VACLKKL VGELEQK (SEQ ID NO.37)
displayed, for clarity showing the heptad repeat pattern and the consensus glycosylation sequence (underlined) in each case, as well as the site of carbohydrate attachment (N) in bold. These sequences are anticipated to form homo-oligomers and also are capable of forming hetero-oligomers if combined."

The assay occurs in the endoplasmic reticulum and golgi apparatus; therefore, the molecule is translated from a nucleic acid template and includes a signal sequence to facilitate transport of the nascent chain into the ER. A proteinaceous fluorophore such as GFP (or other) is required in fusion with the coiled-coil sequence (see above) as either an N- or C-terminal extension of the sequence. A second fluorescent polypeptide comprising a coiled-coil construct is needed (again with leader sequence) to obtain a FRET measurement of coiled-coil heterodimerization. Such a pair of constructs includes:
Leader Sequence: GFP1: coiled-coil sequence, and
Leader Sequence: GFP2: coiled-coil sequence The assay format is:

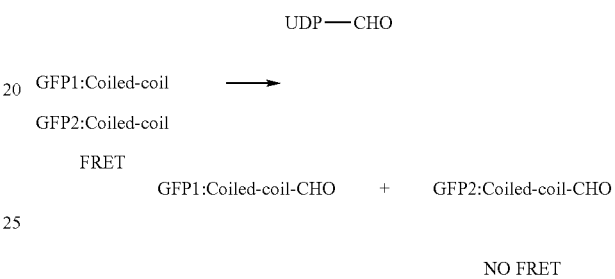

where CHO represents carbohydrate and UDP-CHO an activated form of the carbohydrate appropriate for enzymatic transfer to the target protein. Alternatively, a tandem fusion construct, in which the sequences of the two labeled polypeptides comprising coiled-coils are connected by a linker amino acid sequence on a single polypeptide molecule, is used.

A leader sequence useful in constructs of the glycosylation assays of the invention is provided by residues 1–20 of Folate Receptor β (Genbank Acc. No. X69516). GFP1 and GFP2 sequences are as indicated in WO 97/28261 and WO98/06737 (see SwissProt Accession No. P42212 for GFP; other Genbank and SwissProt accessions list GFP variants of different excitation/emission wavelengths).

The time required for GFP chromophore maturation (Cubitt et al., 1995, *Trends Biol. Sci.*, 20: 448–455) is somewhat extended (up to 2 hours). In instances in which glycosylation occurs prior to this time, a protein fluorophore with more rapid chromophore maturation properties is employed or a strategy to delay transit or processing of the reporter protein through the ER and golgi is devised.

As an alternative to the use of GFP fusion constructs, polypeptides comprising a coiled-coil motif are labeled in vitro by incorporating fluorescent amino acids into the nascent polypeptide chain. In such a case, GFP is not used; rather, the construct is altered to contain at least one (but, preferably, only one) lysine residue. This lysine residue is fluorescently labeled in the in vitro translation experiment (see above) using a pool of fluorophore-Lys:tRNA. If possible, two different fluorophore-Lys:tRNA sources are used where the fluorophores are paired for FRET. A single lysine in the reporter molecule precludes the situation of intramolecular FRET and ensures that only intermolecular FRET is observed. FRET-active pairs of fluorophore-Lys:tRNA are produced using fluorophores such as are described above. Alternatively, a non-FRET fluorescence endpoint could be used where only a single source of fluorescent amino acid is available for the in vitro translation experiment. In this case, numerous Lys residues are placed within the sequence of one of the partner polypeptides (see below). NBD-Lys:tRNA is a fluorescent Lys derivative used extensively in experiments to define protein synthesis and import into the ER (Crowley et al., 1993, Cell, 73: 1101–1115). This is used in an assay of polypeptide glycosylation in the following manner:

Leader Sequence: large protein: coiled-coil sequence 1, plus
Leader Sequence: coiled-coil sequence 2;

where the coiled-coil sequence 1 contains the site of glycosylation at the 'a' position of heptad 3 (as above), does not homodimerize and the entire construct is devoid of Lys residues (large protein and coiled-coil 1 sequence at least); in addition, the coiled-coil sequence 2 is lysine-rich and will not homodimerize, but will heterodimerize with coiled-coil 1, but does not contain a glycosylation site. In this situation, the incorporation of NBD-Lys occurs in the in vitro translation system in coiled-coil 2 only. The heterodimer forms in the absence of glycosylation, and the large size of the complex results in a protein of slow rotational movement, which can be measured by fluorescence anisotrophy techniques and fluorescence correlation spectroscopy. Glycosylation of coiled-coil 1 provokes dissociation of coiled-coil 2 from the large fusion protein, with a concomitant increase in the speed of motion of the fluorescent coiled-coil 2 protein. This is detectable by time-resolved fluorescence anisotrophy measurements and/or fluorescence correlation spectroscopy and forms the basis of an assay for N-glycosylation of proteins according to the invention.

EXAMPLE 4

Detection of ADP-Ribosylation According to the Invention

As discussed above, poly(ADP-ribose) polymerase (PARP from *Drosophila*, Genbank Accession No. D13806) is a nuclear protein capable of poly-ADP-ribosylation of protein targets which performs a control function in DNA repair, replication and other events. The enzyme is an active dimer and contains a putative leucine zipper domain (residues 385–419, Uchida et al., 1993, Proc. Natl. Acad. Sci. USA 90, 3481–3485) which is proposed to mediate protein:protein interactions. The auto-ADP-ribosylation of this enzyme has been noted in a domain containing the leucine zipper motif, which also contains two glutamic acid residues within the leucine zipper which are conserved across PARP from five species. This has raised the possibility that these glutamic acid residues represent the sites of ADP-ribosylation and perhaps control of protein:protein interactions by modulation of coiled-coil partner formation (Uchida et al., 1993).

"According to the invention, an assay for ADP-ribosylation of proteins comprises as the reporter peptide the *Drosophilia* PARP leucine zipper sequence (385–419), adapted to include a site of chemical label attachment:

abcdefg abcdefg abcdefg abcdefg abcdefg (SEQ ID NO.38)
LYNLKFS IICLKNQ HKELRKR IENLGGK FEVKISE$^{419}$ (SEQ ID NO.39)

where the sites of ADP-ribosylation are glutamic acid residues 401, 407, and where the mutation G394C has been introduce to provide an unique site of chemical fluorophore attachment. A coiled-coil dimer is predicted in the absence of ADP-ribosylation, but not in the presence of ADP-ribosylated E-401 or E407. FRET between appropriately labeled peptides of this sequence does not occur prior to ADP-ribosylation and is reduced or eliminated following ADP-ribosylation."

As this protein is normally nuclear located, the reporter peptide is best targeted to the nucleus by inclusion of a nuclear localization sequence (NLS) as an extension to the peptide sequence. Such NLS are well known to those skilled in the art.

Proteinaceous fluorophores are incorporated as extensions of the peptide sequence and serve in combination with or as replacements of chemical fluorophores. Measurements of FRET with and without a modifying enzyme and/or in the presence of a candidate modulator of the modifying enzyme are performed and quantitated as described above.

EXAMPLE 5

A Kit for Assaying the Activity of a Protein-Modifying Enzyme According to the Invention In order to facilitate convenient and widespread use of the invention, a kit is provided which contains the essential components for screening for modulators of the activity of a protein-modifying enzyme, in this case of an enzyme which mediates a change in protein modification, as described above. A pair of differentially-labeled polypeptides comprising a coiled-coil motif, as defined above, is provided, as is a suitable reaction buffer for in vitro assay or, alternatively, cells or a cell lysate. A reaction buffer which is "suitable" is one which is permissive of the activity of the enzyme to be assayed and which permits dimerization of unmodified coiled-coil motifs. The labeled coiled-coil components are, provided as peptide/protein or a nucleic acid comprising a gene expression construct encoding the one or more of a peptide/protein, as discussed above. Polypeptides comprising coiled-coils in a kit of the invention are supplied either in solution (preferably refrigerated or frozen) in a buffer which inhibits degradation and maintains biological activity, or are provided in dried form, i.e., lyophilized. In the latter case, the components are resuspended prior to use in the reaction buffer or other biocompatible solution (e.g. water, containing one or more of physiological salts, a weak buffer, such as phosphate or Tris, and a stabilizing substance such as glycerol, sucrose or polyethylene glycol); in the latter case, the resuspension buffer should not inhibit dimerization of an unmodified polypeptide comprising a coiled-coil when added to the reaction buffer in an amount necessary to deliver sufficient protein for an assay reaction. Polypeptides comprising coiled-coils provided as nucleic acids are supplied- or resuspended in a buffer which permits either transfection/transformation into a cell or organism or in vitro transcription/translation, as described above. Each of these components is supplied separately contained or in admixture with one or more of the others in a container selected from the group that includes, but is not limited to, a tube, vial, syringe or bottle.

Optionally, the kit includes cells. Eukaryotic or prokaryotic cells, as described above, are supplied in- or on a liquid or solid physiological buffer or culture medium (e.g. in suspension, in a stab culture or on a culture plate, e.g. a Petri dish). For ease of shipping, the cells are typically refrigerated, frozen or lyophilized in a bottle, tube or vial. Methods of cell preservation are widely known in the art; suitable buffers and media are widely known in the art, and are obtained from commercial suppliers (e.g., Gibco/LifeTechnologies) or made by standard methods (see, for example Sambrook et al., 1989, *Molecular Cloning. A Laboratory Manual.*, 2nd Edition, Cold Spring Harbor Laboratory Press, Cold Spring Harbor, N.Y.).

An enzyme being assayed according to the invention is added to the assay system either as a protein (isolated, partially-purified or present in a crude preparation such as a cell extract or even a living cell) or a recombinant nucleic acid. Methods of expressing a nucleic acid comprising an enzyme or other protein are well known in the art (see again above).

An assay of the invention is carried out using the kit according to the methods described above in the Examples and elsewhere.

EXAMPLE 6

A Kit for Screening a Candidate Modulator of Protein-Modifying Enzyme Activity According to the Invention A candidate modulator of post-translational modification may be assayed using a kit of the invention. A kit as described in Example 5 is used for this application, with the assay performed further comprising the addition of a candidate modulator of the modifying enzyme which is present to the reaction system. Optionally, a protein-modifying enzyme is supplied with the kit, either as a protein or nucleic acid as described above.

Assays of protein activity are performed as described above. At a minimum, three detections are performed, one in which the labeled polypeptides comprising coiled-coils are present without the modifying enzyme or candidate modulator thereof (control reaction A), one in which the polypeptides comprising coiled-coils are incubated with the modifying enzyme under conditions which permit the modification reaction to occur (control reaction B) and one in which the modifying enzyme and candidate inhibitor are both incubated with the labeled polypeptides comprising coiled-coils under conditions which permit the modification reaction to occur (Test reaction). The result of the last detection procedure is compared with those of the first two controls; the candidate inhibitor is judged to be efficacious if there is a shift in either of the observed amount of FRET or the rate at which FRET changes of at least 10% away from that observed in control reaction B toward that observed in control reaction A.

EXAMPLE 7

In vivo FRET Analysis

A FRET assay according to the invention was performed in vivo in a mammalian cell line as follows.

DNA primers were designed to encode each coil, a stop codon and unique restriction sites (BamHI and EcoRI) at each end to facilitate cloning. Codon usage was selected in order to allow both mammalian and bacterial expression. Two coiled coil peptides were used for in vivo analysis: 4HA, an acidic coiled coil with four heptad repeats and 5HB, a basic coiled coil with five heptad repeats.

The following primers and peptides were utilized.

4HA forward primer:
GGATCCTCTACAAGGGTATTGCTCAGT-TGGAGCAGGAAATCGCCCAAT TAG AACAA-GAAAATGCACAACTTGAA (SEQ ID NO:40)

4HA reverse primer:
GAATTCTTAAAGCTTTTCCTGCT-CAAGCTGAGCGATCTCTTGTTCAAGT TGTG-CATTTTCTTGTTCTAATTGGGCGAT (SEQ ID NO:41)

4HA peptide:
YRILYKGIAQLEQELAQLEQENAQLEQEIAQLEQE (SEQ ID NO:42)

5HB forward primer:
GGATCCTCTATAAGGTATCTGTCAACT-TCGTCAACGTATCGCTCAACTT CGTCAAA-GAAACGCTCAACTCCGC (SEQ ID NO:43)

5FIB Reverse Primer:
GAATTCTTAAAGCYrACGTTGTCGGAGT-TGGGCAATGCGCTGACGGAG CTGGGCAATACGTTGGCGGAGT-TGAGCGTTTCTTTG (SEQ ID NO:44)

5HB peptide:
YKGICQLRQRTAQLRQRNAQLRQRIAQL-RQRIAQLRQR (SEQ ID NO:45)

Plasmids encoding the autofluorescent proteins (AFPs) GFP (red shifted) and BFP (a mutant form of the 28 kDa red shifted GFP) were purchased from Quantum Biotechnologies Inc. The mammalian expression vectors pQBI25 and pQBI50 encode GFP and BFP, respectively. rsGFP has an excitation peak of 473 nm and an emission peak of 509 nm. BFP has an excitation peak of 387 nm and an emission peak of 450 nm.

AFP constructs were prepared by annealing the primers (sequence recited above) by heating to 96° C. followed by slow cooling to room temperature. Complete double stranded DNA was generated by "filling in" the single stranded 5' overhangs using Sequenase enzyme (Amersham). The resulting DNA fragment was purified by electrophoresis in a 1.2% agarose gel and DNA was extracted from an isolated gel band using a Qiagen spin column (Qiagen). The purified fragment was digested with BamHI and EcoRI and purified as above. The purified fragment was ligated into the mammalian expression vectors (digested with BamHI and EcoRI) pQBI25-fc1 and pQBI50-fc1 to generate the vectors FS2 (GFP-5HB) and FS3 (BFP-4HA).

For FRET analysis in mammalian cells, vectors expressing GFP (Quantum Biotechnologies, Inc., QBI25-fc1), GFP-5HB (FS2) and BFP-4HA (FS3) were used. Vectors capable of expressing these proteins were transfected into COS-7 cells (a well-established cell-line derived from monkey kidney cells) individually and in combinations. Transfections were performed using Lipofectamine 2000 (Gibco-BRL) and the transfected cells were incubated at 37° C. for 48 hours to allow the expressed proteins to accumulate to a detectable level.

For each set of transfected cells, FRET was determined by analysis in a BMG Galaxy fluorescent plate reader using the following regime: excitation at 370 nm (excitation for BFP) and emission at 520 nm (emission for GFP). The results from a typical experiment are presented in FIG. 15.

When the vectors were transfected individually, FRET did not occur and there was only a small increase in the amount of background fluorescence resulting from the expressed proteins as compared to the untransfected cells. However, if the two vectors, each expressing a different coiled-coil fusion protein were transfected together, there was a 1.2–1.3 fold increase in the detectable level of FRET as compared to both untransfected cells or cells transfected with only one of the coiled-coil fusion protein expression vectors (FIG. 15, column 6). Significantly, when a vector expressing BFP-4HA was transfected with a vector expressng GFP alone, the transfected cells demonstrated only background levels of fluorescence (FIG. 15, column 4). The results of this control transfection suggest that the increase in fluorescence detected in cells transfected with both BFP-4HA and GFP-5HB expression vectors is a direct result of FRET and is not due to background fluorescence produced by the two expressed AFP fusion proteins (FIG. 15, column 6).

EXAMPLE 8

Assaying PKA Activity in vitro with AFP Labelled Coiled-Coil Heterodimers

Assays are performed to demonstrate the use of GFP and BFP labelled coiled-coil heterodimers for assaying PKA activity in vitro. Constructs equivalent to those described below can be expressed in mammalian cell cultures and FRET can be monitored.

Vector Construction

DNA primers are designed encoding each coil with a stop codon and unique restriction sites (BamHI & EcoRI) at each end to facilitate cloning. Codon usage is selected in order to allow both mammalian and bacterial expression. Two such coiled coil peptides are used for this study, 4HA-P, an acidic coiled coil with 4 heptad repeats and 5HB-P, a basic coiled coil with 5 heptad repeats.

| Coiled coil | Sequence |
|---|---|
| 4HA-P Forward primer | GGATCCTCTACAAGGGTATTGCTCAGTTGGAGCAGGA AATCCGCCGCCTTCGCCGCAAAAGCGCACAACTTGAA (SEQ ID NO.46) |
| 4HA-P Reverse primer | GAATTCTTAAAGCTTTTCCTGCTCAAGCTGAGCGATC TCTTGTTCAAGTTGTGCGCTTTTGCGGCGAAGGCGGC GGAT (SEQ ID NO.47) |
| 4HA-P Peptide | YRILYKGIAQLEQEIRRLRRKSAQLEQEIAQLEQE (SEQ ID NO.48) |
| 5HB-P Forward primer | GGATCCTCTATAAAGGCATCTGTCAGCTTCGCCAACG CATCCGCCGCCTTCGCCGCAAAAGCGCTCAGCTCCGC (SEQ ID NO.49) |
| 5HB-P Reverse primer | GAATTCTTAAAGCTTGCGCTGGCGGAGCTGGGCAATG CGCTGGCGGAGCTGGGCAATGCGTTGGCGGAGCTGAG CGCTTTTGCG (SEQ ID NO.50) |
| 5HB-P Peptide | YKGICQLRQRIRRLRRKSAQLRQRIAQLRQRIAQLRQ R |

The primers are annealed together by heating to 96° C. followed by slow cooling to room temperature. Complete double-stranded DNA is generated by "filling in" the single stranded 5' overhangs using Sequenase (Amersham). The DNA fragments are purified by electrophoresis in 1.2% agarose gel and DNA is extracted from an isolated gel band using Qiagen spin columns. The DNA fragments are digested with the restriction enzymes BamHI and EcoRI and purified as above prior to ligation into pQBI25-fC1 (GFP) and pQBI50-fC1 (BFP) to generate mammalian expression vectors for GFP-5HB-P (pFS59) and BFP-4HA-P (pFS72). To generate equivalent bacterial expression vectors, DNA is isolated from pFS59 and pFS72 by digestion with NheI and EcoRI, gel purified as above and ligated into pET28a (Novagen) to generate the vectors pFS84 and pFS82 respectively. These vectors allow bacterial expression of the AFP-coiled coil with an N-terminal hexa-His tag, under the control of a T7 promoter.

Bacterial Expression and Protein Purification.

Vectors pFS84 and pFS82 are transformed into BLR (DE3) pLysS (Novagen) and single colonies are used to inoculate 3 ml LB/kanamycin (100 μg/ml). The starter cultures are incubated overnight at 37° C. with shaking. From these starter cultures 1 ml is used to inoculate 400 ml Terrific Broth/kanamycin (100 μg/ml) in a 2L, baffled flask. Cultures are incubated at 37° C. at 200 rpm for approximately 5 hr until the OD600 nm reaches 0.5 Abs units. At this point cultures are induced by adding IPTG to a concentration of 1 mM. The cultures are then incubated at room temperature overnight with gentle shaking on a benchtop rotator.

Bacteria are harvested by centrifugation at 3000 rpm for 20 min. The bacterial pellet is resuspended in 25 ml lysis buffer (50 mM Pi pH 7.0, 300 mM NaCl, 2% Proteinase inhibitor cocktail (Sigma), 0.75 mg/ml Lysozyme). Lysis of the resuspended cells is initiated by gentle stirring for 1 hr at room temperature. The partially lysed mixture is subjected to 2 cycles of freeze thawing in liquid nitrogen. Finally the cells are sonicated on ice using a 10 mm probe at high power. Sonication is performed on a pulse setting for a period of 3 min. The crude lysate is then centrifuged at 15,000 rpm for 30 mins to remove cell debris. Hexa-His tagged proteins are purified from the cleared lysate using TALON® resin (Clontech). Proteins are bound to the resin in a batchwise manner by gentle shaking at room temperature for 30 min. Non-His tagged proteins are removed by washing the resin at least twice with a 10×bed volume of wash buffer (50 mM sodium phosphate pH 7.0, 300 mM NaCl, 5 mM fluorescence-blank Imidazole). The washed resin is loaded into a 2 ml column and the bound proteins are released with elution buffer (50 mM sodium phosphate pH 7.0, 300 mM NaCl, 150 mM fluorescence-blank Imidazole). Elution is normally achieved after the first 0.5 ml and within 2–3 ml in total. Proteins are stored at −80° C. after snap freezing in liquid nitrogen in the presence of 10% glycerol.

In vitro PKA Enzyme Assay

A typical experiment consists of 2 μl BFP-4HA-P, 20 μl GFP-5HA-P and 78 μl Phosphorylation Buffer (50 mM Histidine pH 7, 5 mM MgSO$_4$, 120 mM KCl, 5 mM NaF, 0.2 mg/ml BSA, 1 mM ATP) +/−2 μM PKA inhibitor. FRET is established by incubation at 30° C. Each well is excited using a BFP excitation wavelength filter (TR EX, 310–370 nm) and read using filters for either BFP (450–10 nm) emission or GFP (520–35 nm) emission wavelengths on a BMG 'polar star Galaxy' fluorescent plate reader. The enzyme assay is initiated by adding PKA (2 μl undiluted stock, 0.6 mg/ml) and reading the plate over a time course. (incubated at 30° C.). The results of a typical experiment are presented in FIG. 16.

FRET in Mammalian Cells

Experiments are performed using vectors capable of expressing GFP-5HB-P (FS59) and BFP-4HA-P (FS72). Vectors capable of expressing these proteins are transfected into COS-7 cells (a well established cell-line derived from monkey kidney cells) individually and in combinations. Transfections are performed using Lipofectamine 2000 (GibcoBRL) and the transfected cells are left at 37° C. for 48 hr to allow the expressed proteins to accumulate to a detectable level. In each of the transfections the amount of FRET is determined by analysis in a BMG Galaxy fluorescent plate reader using the following regime:

excitation at $370_{nm}$ (excitation for BFP) and emission at $520_{nm}$ (emission for GFP). Once the FRET signal is determined PKA activators can be added to the growth media (e.g. 100 μM Forskolin) and the resultant reduction in FRET monitored in real time.

USE

The invention is useful in monitoring the activity of a protein-modifying enzyme, whether the protein is isolated, partially-purified, present in a crude preparation or present in a living cell. The invention is further useful in assaying a cell or cell extract for the presence- or level of activity of a protein modifying enzyme. The invention is additionally useful in assaying the activity of naturally-occurring (mutant) or synthetic (engineered) isoforms of known protein modifying enzymes or, instead, that of novel (natural or synthetic) enzymes. The invention is of use in assaying the efficacy of candidate modulators of the activity of a protein modifying enzyme in inhibiting or enhancing the activity of that enzyme; moreover, is useful to screen potential therapeutic drugs for activity against cloned and/or purified enzymes that may have important clinical pathogenicities when mutated. The invention is further of use in the screening of candidate bioactive agents (e.g., drugs) for side effects, whereby the ability of such an agent to modulate the activity of a protein modifying enzyme may be indicative a propensity toward provoking unintended side-effects to a therapeutic or other regimen in which that agent might be employed.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims.

The invention claimed is:

1. A method of screening for a modulator of an enzyme, comprising the steps of:
   a) contacting said enzyme, an isolated polypeptide and a binding partner of said polypeptide to form a mixture, wherein said isolated polypeptide comprises a site for post-translational modification, wherein said enzyme catalyzes a reaction at said site of post-translational modification, wherein said reaction results in association of said isolated polypeptide and said binding partner, and wherein each of said isolated polypeptide and said binding partner comprise a detection means for monitoring association of said isolated polypeptide and said binding partner, and wherein each of said isolated polypeptide and said binding partner comprises at least one coiled-coil structure, and wherein said association occurs in a coiled-coil dependent manner;
   b) contacting the mixture of step (a) with a candidate modulator; and
   c) monitoring association of said isolated polypeptide and said binding partner in each of steps (a) and (b), wherein a change in association of said isolated polypeptide and said binding partner between step (a) and step (b) identifies the candidate modulator as a modulator of the enzyme.

2. A method of screening for a modulator of an enzyme, comprising the steps of:
   a) providing an isolated polypeptide and a binding partner of said polypeptide,
   wherein said isolated polypeptide comprises a site for post-translational modification, wherein said enzyme catalyzes a reaction at said site of post-translational modification, wherein said reaction results in association of said isolated polypeptide and said binding partner, and wherein each of said isolated polypeptide and said binding partner comprise detection means for monitoring association of said isolated polypeptide and said binding partner, and wherein each of said isolated polypeptide and said binding partner comprises at least one coiled-coil structure, and wherein said association occurs in a coiled-coil dependent manner;
   b) contacting said isolated polypeptide and binding partner with said enzyme;
   c) contacting a candidate modulator with said enzyme, isolated polypeptide and binding partner of said polypeptide; and
   d) monitoring association of said isolated polypeptide and said binding partner in each of steps (a), (b), and (c) wherein a change in association of said isolated polypeptide and said binding partner between step (a) and step (c) and step (b) and (c) identifies the candidate modulator as a modulator of the enzyme.

3. A method of screening for a modulator of an enzyme, comprising the steps of:
   a) contacting said enzyme, an isolated polypeptide and a binding partner of said polypeptide to form a mixture, wherein said isolated polypeptide and said binding partner are associated,
   wherein said isolated polypeptide comprises a site for post-translational modification, wherein said enzyme catalyzes a reaction at said site of post-translational modification, wherein said reaction results in dissociation of said isolated polypeptide and said binding partner, and wherein each of said isolated polypeptide and said binding partner comprise a detection means for monitoring dissociation of said isolated polypeptide and said binding partner, and wherein each of said isolated polypeptide and said binding partner comprises at least one coiled-coil structure, and wherein said dissociation occurs in a coiled-coil dependent manner;
   b) contacting the mixture of step (a) with a candidate modulator; and
   c) monitoring dissociation of said isolated polypeptide and said binding partner in each of steps (a) and (b), wherein a change in dissociation of said isolated polypeptide and said binding partner between step (a) and step (b) identifies the candidate modulator as a modulator of the enzyme.

4. A method of screening for a modulator of an enzyme, comprising the steps of:
   a) providing an isolated polypeptide and a binding partner of said polypeptide, wherein said isolated polypeptide and said binding partner are associated
   wherein said isolated polypeptide comprises a site for post-translational modification, wherein said enzyme catalyzes a reaction at said site of post-translational modification, wherein said reaction results in dissociation of said isolated polypeptide and said binding partner, and wherein each of said isolated polypeptide and said binding partner comprise detection means for monitoring dissociation of said isolated polypeptide and said binding partner, and wherein each of said isolated polypeptide and said binding partner comprises at least one coiled-coil structure, and wherein said dissociation occurs in a coiled-coil dependent manner;
   b) contacting said isolated polypeptide and binding partner with said enzyme;
   c) contacting a candidate modulator with said enzyme, isolated polypeptide and binding partner of said polypeptide; and
   d) monitoring dissociation of said isolated polypeptide and said binding partner in each of steps (a), (b), and (c) wherein a change in dissociation of said isolated polypeptide and said binding partner between step (a)

and step (c) and step (b) and (c) identifies the candidate modulator as a modulator of the enzyme.

5. The method according to claim 1, 2, 3 or 4, wherein said detection means comprises a light emitting detection means.

6. The method according to claim 5, wherein said light emitting detection means emits fluorescent light.

7. The method according to claim 6, wherein said light emitting detection means comprises two different fluorophores.

8. The method according to claim 7, wherein said fluorophores comprise fluorescein and tetramethylrhodamine.

9. The method according to claim 5, wherein at least one of said isolated polypeptide and said binding partner comprises a cysteine amino acid through which said light emitting detection means is attached via a covalent bond.

10. The method according to claim 6, wherein said light emitting detection means comprises two different fluorescent proteins.

11. The method according to claim 10, wherein said two different fluorescent proteins comprise green fluorescent protein and red fluorescent protein.

12. The method according to claim 10, wherein said two different fluorescent proteins comprise green fluorescent protein and blue fluorescent protein.

13. The method according to claim 1, 2, 3 or 4 wherein said monitoring comprises detecting a change in energy transfer upon association or dissociation of said isolated polypeptide and said binding partner.

14. The method according to claim 13, wherein said detecting is performed by fluorescent resonance energy transfer (FRET).

15. The method of claim 1, 2, 3 or 4, wherein said enzyme is selected from the group consisting of a kinase, a phosphatase, a UDP-N-Acetylglucosamine-Dolichyl-phosphate-N-acetylsglucosamine phosphotransferase, an O-GlcNAc transferase, a ubiquitin activating enzyme E1, a ubiquitin conjugating enzyme E2, a ubiquitin protein ligase E3, a poly (ADP-ribose) polymerase and an NAD:Arginine ADP ribosyltransferase.

16. The method of claim 1, 2, 3 or 4, wherein said reaction comprises addition or removal of a moiety selected from the group consisting of: phosphate, ubiquitin, glycosyl and ADP-ribosyl.

17. The method of claim 1, 2, 3 or 4 wherein said site is engineered.

18. The method of claim 1, 2, 3 or 4, wherein said binding partner comprises a site for post-translational modification.

19. The method of claim 18, wherein said site present in said binding partner is engineered.

20. The method of claim 19, wherein said site present in said isolated polypeptide is engineered.

21. The method of claim 1, 2, 3 or 4, wherein said association or dissociation comprises interactions between hydrophobic sidechains present in said coiled-coil structure.

22. The method of claim 1, 2, 3 or 4, wherein said isolated polypeptide is either synthetic or naturally occurring.

23. The method of claim 1, 2, 3 or 4, wherein said reaction at said site for post-translational modification is reversible.

24. The method of claim 1, 2, 3 or 4, wherein said isolated polypeptide and said binding partner associate with a binding constant that permits detection of binding.

25. The method of claim 1, 2, 3 or 4, wherein said reaction is a post-translational modification reaction.

26. The method of claim 25, wherein said post-translational modification reaction is selected from the group consisting of: phosphorylation, dephosphorylation, glycosylation, ubiquitination, and ADP-ribosylation.

27. The method of claim 1, 2, 3 or 4, wherein said candidate compound is a biological macromolecule, an extract made from biological materials, or a small molecule.

28. The method of claim 1, 2, 3 or 4, wherein said candidate compound is present in a test sample.

29. The method of claim 1 or 3, wherein the association or dissociation that occurs in step (a) is compared to the association or dissociation that occurs in step (b).

30. The method of claim 2, or 4, wherein the association or dissociation that occurs in step (c) is compared to the association or dissociation that occurs in step (a) and step (b).

31. The method of claim 1, 2, 3 or 4, wherein said candidate modulator is an inhibitor of said enzyme.

32. The method of claim 1, 2, 3 or 4, wherein said candidate modulator is an activator of said enzyme.

33. The method of claim 1, 2, 3 or 4, wherein said change in said association or dissociation is at least 10 %.

34. The method of claim 14, wherein said change in association or dissociation is a difference in the amount of FRET or the rate at which FRET changes.

* * * * *

SEQUENCE LISTING

```
<160> NUMBER OF SEQ ID NOS: 51

<210> SEQ ID NO 1
<211> LENGTH: 43
<212> TYPE: PRT
<213> ORGANISM: Artificial Sequence
<220> FEATURE:
<223> OTHER INFORMATION: Conserved Colied-coil domain
<220> FEATURE:
<221> NAME/KEY: DOMAIN
<222> LOCATION: (1)..(43)
<223> OTHER INFORMATION: Conserved Coiled-coil domain

<400> SEQUENCE: 1

Phe Gly Ala Asx Cys Asp Glu Phe Gly Ala Asx Cys Asp Glu Phe Gly
1               5                   10                  15

Ala Asx Cys Asp Glu Phe Gly Ala Asx Cys Asp Glu Phe Gly Ala Asx
            20                  25                  30

Cys Asp Glu Phe Gly Ala Asx Cys Asp Glu Gly
        35                  40

<210> SEQ ID NO 2
<211> LENGTH: 41
<212> TYPE: PRT
<213> ORGANISM: Homo sapiens

<400> SEQUENCE: 2

Ile Leu Ile Ser Leu Glu Ser Glu Glu Arg Gly Glu Leu Glu Arg Ile
1               5                   10                  15

Leu Ala Asp Leu Glu Glu Glu Asn Arg Asn Leu Gln Ala Glu Tyr Asp
            20                  25                  30

Arg Leu Lys Gln Gln His Glu His Lys
        35                  40

<210> SEQ ID NO 3
<211> LENGTH: 32
<212> TYPE: PRT
<213> ORGANISM: Saccharomyces cerevisiae

<400> SEQUENCE: 3

Met Lys Gln Leu Glu Asp Lys Val Glu Glu Leu Leu Ser Lys Asn Tyr
1               5                   10                  15

His Leu Glu Asn Glu Val Ala Arg Leu Lys Lys Leu Val Gly Glu Arg
            20                  25                  30
```

```
<210> SEQ ID NO 4
<211> LENGTH: 39
<212> TYPE: PRT
<213> ORGANISM: Homo sapiens

<400> SEQUENCE: 4

Thr Asp Thr Leu Gln Ala Glu Thr Asp Gln Leu Glu Asp Glu Lys Ser
1               5                   10                  15

Ala Leu Gln Thr Glu Ile Ala Asn Leu Leu Lys Glu Lys Glu Lys Leu
            20                  25                  30

Glu Phe Ile Leu Ala Ala His
        35

<210> SEQ ID NO 5
<211> LENGTH: 39
<212> TYPE: PRT
<213> ORGANISM: Homo sapiens

<400> SEQUENCE: 5

Ile Ala Arg Leu Glu Glu Lys Val Lys Thr Leu Lys Ala Gln Asn Ser
1               5                   10                  15

Glu Leu Ala Ser Thr Ala Asn Met Leu Arg Glu Gln Val Ala Gln Leu
            20                  25                  30

Lys Gln Lys Val Met Asn His
        35

<210> SEQ ID NO 6
<211> LENGTH: 38
<212> TYPE: PRT
<213> ORGANISM: Escherichia coli

<400> SEQUENCE: 6

Val Asp Lys Leu Gly Ala Leu Glu Glu Arg Arg Lys Val Leu Gln Val
1               5                   10                  15

Lys Thr Glu Asn Leu Gln Ala Glu Arg Asn Ser Arg Ser Lys Ser Ile
            20                  25                  30

Gly Gln Ala Lys Ala Arg
        35

<210> SEQ ID NO 7
<211> LENGTH: 32
<212> TYPE: PRT
<213> ORGANISM: Escherichia coli

<400> SEQUENCE: 7

Glu Pro Leu Arg Leu Glu Val Asn Lys Leu Gly Glu Glu Leu Asp Ala
1               5                   10                  15

Ala Lys Ala Glu Leu Asp Ala Leu Gln Ala Glu Ile Arg Asp Ile Ala
            20                  25                  30

<210> SEQ ID NO 8
<211> LENGTH: 33
<212> TYPE: PRT
<213> ORGANISM: Thermus thermophilus

<400> SEQUENCE: 8

Asp Leu Glu Ala Leu Leu Ala Leu Asp Arg Glu Val Gln Glu Leu Lys
1               5                   10                  15

Lys Arg Leu Gln Glu Val Gln Thr Glu Arg Asn Gln Val Ala Lys Arg
            20                  25                  30
```

Val

<210> SEQ ID NO 9
<211> LENGTH: 32
<212> TYPE: PRT
<213> ORGANISM: Thermus thermophilus

<400> SEQUENCE: 9

Glu Ala Leu Ile Ala Arg Gly Lys Ala Leu Gly Glu Glu Ala Lys Arg
1               5                   10                  15

Leu Glu Glu Ala Leu Arg Glu Lys Glu Ala Arg Leu Glu Ala Leu Leu
            20                  25                  30

<210> SEQ ID NO 10
<211> LENGTH: 30
<212> TYPE: PRT
<213> ORGANISM: Escherichia coli

<400> SEQUENCE: 10

Leu Arg Gly Ala Glu Lys Leu Arg Glu Glu Leu Asp Phe Leu Lys Ser
1               5                   10                  15

Val Phe Arg Pro Glu Ile Ile Ala Ala Ile Ala Glu Ala Arg
            20                  25                  30

<210> SEQ ID NO 11
<211> LENGTH: 26
<212> TYPE: PRT
<213> ORGANISM: Escherichia coli

<400> SEQUENCE: 11

Ala Glu Tyr His Ala Ala Arg Glu Gln Gln Gly Phe Cys Glu Gly Arg
1               5                   10                  15

Ile Lys Asp Ile Glu Ala Lys Leu Ser Asn
            20                  25

<210> SEQ ID NO 12
<211> LENGTH: 32
<212> TYPE: PRT
<213> ORGANISM: Saccharomyces cerevisiae

<400> SEQUENCE: 12

Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Arg
            20                  25                  30

<210> SEQ ID NO 13
<211> LENGTH: 29
<212> TYPE: PRT
<213> ORGANISM: Saccharomyces cerevisiae

<400> SEQUENCE: 13

Glu Trp Glu Ala Leu Glu Lys Lys Leu Ala Ala Leu Glu Ser Lys Leu
1               5                   10                  15

Gln Ala Leu Glu Lys Lys Leu Glu Ala Leu Glu His Gly
            20                  25

<210> SEQ ID NO 14
<211> LENGTH: 32
<212> TYPE: PRT
<213> ORGANISM: Saccharomyces cerevisiae -continued

```
<400> SEQUENCE: 14

Met Lys Gln Ile Glu Asp Lys Leu Glu Ile Leu Ser Lys Leu Tyr
1               5                   10                  15

His Ile Glu Asn Glu Leu Ala Arg Ile Lys Lys Leu Leu Gly Glu Arg
            20                  25                  30

<210> SEQ ID NO 15
<211> LENGTH: 25
<212> TYPE: PRT
<213> ORGANISM: Escherichia coli

<400> SEQUENCE: 15

Gln Glu Lys Thr Ala Leu Asn Met Ala Arg Phe Ile Arg Ser Gln Thr
1               5                   10                  15

Leu Thr Leu Leu Glu Lys Leu Asn Glu
            20                  25

<210> SEQ ID NO 16
<211> LENGTH: 24
<212> TYPE: PRT
<213> ORGANISM: Escherichia coli

<400> SEQUENCE: 16

Asp Glu Gln Ala Asp Ile Cys Glu Ser Leu His Asp His Ala Asp Glu
1               5                   10                  15

Leu Tyr Arg Ser Cys Leu Ala Arg
            20

<210> SEQ ID NO 17
<211> LENGTH: 16
<212> TYPE: PRT
<213> ORGANISM: Homo sapiens

<400> SEQUENCE: 17

Leu Ile Leu Ile Cys Leu Leu Leu Ile Cys Ile Ile Val Met Leu Leu
1               5                   10                  15

<210> SEQ ID NO 18
<211> LENGTH: 17
<212> TYPE: PRT
<213> ORGANISM: Bos taurus

<400> SEQUENCE: 18

Met Leu Cys Cys Met Arg Arg Thr Lys Gln Val Glu Lys Asn Asp Asp
1               5                   10                  15

Asp

<210> SEQ ID NO 19
<211> LENGTH: 10
<212> TYPE: PRT
<213> ORGANISM: Bos taurus

<400> SEQUENCE: 19

Phe Lys Gln Arg Gln Thr Arg Gln Phe Lys
1               5                   10

<210> SEQ ID NO 20
<211> LENGTH: 30
<212> TYPE: PRT
<213> ORGANISM: Artificial Sequence
<220> FEATURE:
<223> OTHER INFORMATION: Conserved ubiquitination site
<220> FEATURE:
```

```
<221> NAME/KEY: DOMAIN
<222> LOCATION: (1)..(30)
<223> OTHER INFORMATION: Conserved ubiquitination site

<400> SEQUENCE: 20

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His
            20                  25                  30

<210> SEQ ID NO 21
<211> LENGTH: 21
<212> TYPE: PRT
<213> ORGANISM: Artificial Sequence
<220> FEATURE:
<223> OTHER INFORMATION: Conserved ubiquitination site
<220> FEATURE:
<221> NAME/KEY: DOMAIN
<222> LOCATION: (1)..(21)
<223> OTHER INFORMATION: Conserved ubiquitination site

<400> SEQUENCE: 21

His Gly Ser Gly Ala Trp Leu Leu Pro Val Ser Leu Val Lys Arg Lys
1               5                   10                  15

Thr Thr Leu Ala Pro
            20

<210> SEQ ID NO 22
<211> LENGTH: 10
<212> TYPE: PRT
<213> ORGANISM: Homo sapiens

<400> SEQUENCE: 22

Gly Thr Thr Ser Thr Ile Gln Thr Ala Pro
1               5                   10

<210> SEQ ID NO 23
<211> LENGTH: 12
<212> TYPE: PRT
<213> ORGANISM: Homo sapiens

<400> SEQUENCE: 23

Ser Ala Val Ser Ser Ala Asp Gly Thr Val Leu Lys
1               5                   10

<210> SEQ ID NO 24
<211> LENGTH: 18
<212> TYPE: PRT
<213> ORGANISM: Homo sapiens

<400> SEQUENCE: 24

Asp Ser Ser Thr Asp Leu Thr Gln Thr Ser Ser Ser Gly Thr Val Thr
1               5                   10                  15

Leu Pro

<210> SEQ ID NO 25
<211> LENGTH: 12
<212> TYPE: PRT
<213> ORGANISM: Homo sapiens

<400> SEQUENCE: 25

Met Ala Gly Gly Pro Ala Asp Thr Ser Asp Pro Leu
1               5                   10
```

<210> SEQ ID NO 26
<211> LENGTH: 13
<212> TYPE: PRT
<213> ORGANISM: Homo sapiens

<400> SEQUENCE: 26

Ala Gln Thr Ile Thr Ser Glu Thr Pro Ser Ser Thr Thr
1               5                   10

<210> SEQ ID NO 27
<211> LENGTH: 36
<212> TYPE: PRT
<213> ORGANISM: Artificial Sequence
<220> FEATURE:
<223> OTHER INFORMATION: Conserved phosphorylation site
<220> FEATURE:
<221> NAME/KEY: DOMAIN
<222> LOCATION: (1)..(36)
<223> OTHER INFORMATION: Conserved phosphorylation site

<400> SEQUENCE: 27

Arg Met Lys Gln Leu Glu Asp Lys Val Glu Glu Leu Leu Ser Lys Thr
1               5                   10                  15

Tyr His Leu Glu Asn Glu Val Ala Cys Leu Lys Lys Leu Val Gly Glu
            20                  25                  30

Arg Ala Ala Lys
        35

<210> SEQ ID NO 28
<211> LENGTH: 36
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(36)
<223> OTHER INFORMATION: Synthesized peptide

<400> SEQUENCE: 28

Arg Met Lys Gln Leu Glu Asp Gln Val Arg Arg Leu Arg Arg Lys Ser
1               5                   10                  15

Tyr His Leu Glu Asn Glu Val Ala Cys Leu Lys Lys Leu Val Gly Glu
            20                  25                  30

Arg Ala Ala Lys
        35

<210> SEQ ID NO 29
<211> LENGTH: 36
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(36)
<223> OTHER INFORMATION: Synthesized peptide

<400> SEQUENCE: 29

Arg Met Lys Gln Leu Glu Asp Gln Val Arg Arg Leu Arg Arg Lys Thr
1               5                   10                  15

Tyr His Leu Glu Asn Glu Val Ala Cys Leu Lys Lys Leu Val Gly Glu
            20                  25                  30

Arg Ala Ala Lys
        35

```
<210> SEQ ID NO 30
<211> LENGTH: 34
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(34)
<223> OTHER INFORMATION: Synthesized peptide

<400> SEQUENCE: 30

His Met Lys Gln Leu Glu Asp Lys Val Glu Glu Leu Leu Ser Lys Asn
1               5                   10                  15

Tyr Cys Leu Glu Asn Glu Val Arg Arg Leu Arg Arg Ala Ser Phe Ser
            20                  25                  30

Leu Gln

<210> SEQ ID NO 31
<211> LENGTH: 35
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(35)
<223> OTHER INFORMATION: Synthesized peptide

<400> SEQUENCE: 31

Arg Arg Ile Arg Arg Ala Ser Ile Asp Lys Val Glu Glu Leu Lys Ser
1               5                   10                  15

Lys Asn Tyr Cys Leu Glu Asn Glu Val Ala Arg Leu Lys Lys Leu Val
            20                  25                  30

Gly Glu Arg
        35

<210> SEQ ID NO 32
<211> LENGTH: 35
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(35)
<223> OTHER INFORMATION: Synthesized peptide

<400> SEQUENCE: 32

Ala Asx Cys Asp Glu Phe Gly Ala Asx Cys Asp Glu Phe Gly Ala Asx
1               5                   10                  15

Cys Asp Glu Phe Gly Ala Asx Cys Asp Glu Phe Gly Ala Asx Cys Asp
            20                  25                  30

Glu Phe Gly
        35

<210> SEQ ID NO 33
<211> LENGTH: 12
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(12)
<223> OTHER INFORMATION: Synthesized peptide
```

```
<400> SEQUENCE: 33

Ser Ala Val Ser Ser Ala Asp Gly Thr Val Leu Lys
1               5                   10

<210> SEQ ID NO 34
<211> LENGTH: 35
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(35)
<223> OTHER INFORMATION: Synthesized peptide

<400> SEQUENCE: 34

Ile Ala Ala Leu Glu Gln Lys Ile Ala Ala Leu Ser Ala Val Ser Ser
1               5                   10                  15

Asp Leu Gly Thr Val Leu Lys Cys Leu Gln Gln Lys Ile Ala Ala Leu
            20                  25                  30

Glu Gln Lys
        35

<210> SEQ ID NO 35
<211> LENGTH: 4
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(4)
<223> OTHER INFORMATION: Synthesized peptide

<400> SEQUENCE: 35

Leu Glu Gln Lys
1

<210> SEQ ID NO 36
<211> LENGTH: 36
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(36)
<223> OTHER INFORMATION: Synthesized peptide

<400> SEQUENCE: 36

Arg Met Lys Gln Leu Glu Asp Lys Val Glu Glu Leu Leu Ser Lys Asn
1               5                   10                  15

Tyr Ser Leu Glu Asn Glu Val Ala Cys Leu Lys Lys Leu Val Gly Glu
            20                  25                  30

Leu Glu Gln Lys
        35

<210> SEQ ID NO 37
<211> LENGTH: 36
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(36)
```

<223> OTHER INFORMATION: Synthesized peptide

<400> SEQUENCE: 37

Arg Met Lys Gln Leu Glu Asp Lys Val Glu Glu Leu Leu Ser Lys Asn
1               5                   10                  15

Tyr Thr Leu Glu Asn Glu Val Ala Cys Leu Lys Lys Leu Val Gly Glu
            20                  25                  30

Leu Glu Gln Lys
            35

<210> SEQ ID NO 38
<211> LENGTH: 35
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(35)
<223> OTHER INFORMATION: Synthesized peptide

<400> SEQUENCE: 38

Ala Asx Cys Asp Glu Phe Gly Ala Asx Cys Asp Glu Phe Gly Ala Asx
1               5                   10                  15

Cys Asp Glu Phe Gly Ala Asx Cys Asp Glu Phe Gly Ala Asx Cys Asp
            20                  25                  30

Glu Phe Gly
        35

<210> SEQ ID NO 39
<211> LENGTH: 35
<212> TYPE: PRT
<213> ORGANISM: Artificial Sequence
<220> FEATURE:
<223> OTHER INFORMATION: Synthesized peptide
<220> FEATURE:
<221> NAME/KEY: PEPTIDE
<222> LOCATION: (1)..(35)
<223> OTHER INFORMATION: Synthesized peptide

<400> SEQUENCE: 39

Leu Tyr Asn Leu Lys Phe Ser Ile Ile Cys Leu Lys Asn Gln His Lys
1               5                   10                  15

Glu Leu Arg Lys Arg Ile Glu Asn Leu Gly Gly Lys Phe Glu Val Lys
            20                  25                  30

Ile Ser Glu
        35

<210> SEQ ID NO 40
<211> LENGTH: 74
<212> TYPE: DNA
<213> ORGANISM: Artificial sequence
<220> FEATURE:
<223> OTHER INFORMATION: Primer

<400> SEQUENCE: 40
ggatcctcta caagggtatt gctcagttgg agcaggaaat cgcccaatta gaacaagaaa        60
atgcacaact tgaa        74

<210> SEQ ID NO 41
<211> LENGTH: 78
<212> TYPE: DNA
<213> ORGANISM: Artificial sequence
<220> FEATURE:

<223> OTHER INFORMATION: Primer

<400> SEQUENCE: 41
gaattcttaa agcttttcct gctcaagctg agcgatctct tgttcaagtt gtgcattttc    60
ttgttctaat tgggcgat    78

<210> SEQ ID NO 42
<211> LENGTH: 35
<212> TYPE: PRT
<213> ORGANISM: Artificial sequence
<220> FEATURE:
<223> OTHER INFORMATION: Synthesized peptide

<400> SEQUENCE: 42

Tyr Arg Ile Leu Tyr Lys Gly Ile Ala Gln Leu Glu Gln Glu Ile Ala
1               5                   10                  15

Gln Leu Glu Gln Glu Asn Ala Gln Leu Glu Gln Glu Ile Ala Gln Leu
            20                  25                  30

Glu Gln Glu
        35

<210> SEQ ID NO 43
<211> LENGTH: 73
<212> TYPE: DNA
<213> ORGANISM: Artificial sequence
<220> FEATURE:
<223> OTHER INFORMATION: Primer

<400> SEQUENCE: 43
ggatcctcta taaggtatct gtcaacttcg tcaacgtatc gctcaacttc gtcaaagaaa    60
cgctcaactc cgc    73

<210> SEQ ID NO 44
<211> LENGTH: 84
<212> TYPE: DNA
<213> ORGANISM: Artificial sequence
<220> FEATURE:
<223> OTHER INFORMATION: Primer

<400> SEQUENCE: 44
gaattcttaa agcttacgtt gtcggagttg ggcaatgcgc tgacggagct gggcaatacg    60
ttggcggagt tgagcgtttc tttg    84

<210> SEQ ID NO 45
<211> LENGTH: 38
<212> TYPE: PRT
<213> ORGANISM: Artificial sequence
<220> FEATURE:
<223> OTHER INFORMATION: Synthesized peptide

<400> SEQUENCE: 45

Tyr Lys Gly Ile Cys Gln Leu Arg Gln Arg Thr Ala Gln Leu Arg Gln
1               5                   10                  15

Arg Asn Ala Gln Leu Arg Gln Arg Ile Ala Gln Leu Arg Gln Arg Ile
            20                  25                  30

Ala Gln Leu Arg Gln Arg
        35

<210> SEQ ID NO 46
<211> LENGTH: 74
<212> TYPE: DNA
<213> ORGANISM: Artificial sequence
<220> FEATURE:
<223> OTHER INFORMATION: Peptide

<400> SEQUENCE: 46
ggatcctcta caagggtatt gctcagttgg agcaggaaat ccgccgcctt cgccgcaaaa    60
gcgcacaact tgaa    74

<210> SEQ ID NO 47
<211> LENGTH: 78
<212> TYPE: DNA
<213> ORGANISM: Artificial sequence
<220> FEATURE:
<223> OTHER INFORMATION: Primer

<400> SEQUENCE: 47
gaattcttaa agcttttcct gctcaagctg agcgatctct tgttcaagtt gtgcgctttt    60
gcggcgaagg cggcggat    78

<210> SEQ ID NO 48
<211> LENGTH: 35
<212> TYPE: PRT
<213> ORGANISM: Artificial sequence
<220> FEATURE:
<223> OTHER INFORMATION: Synthesized peptide

<400> SEQUENCE: 48

Tyr Arg Ile Leu Tyr Lys Gly Ile Ala Gln Leu Glu Gln Glu Ile Arg
1               5                   10                  15

Arg Leu Arg Arg Lys Ser Ala Gln Leu Glu Gln Glu Ile Ala Gln Leu
            20                  25                  30

Glu Gln Glu
        35

<210> SEQ ID NO 49
<211> LENGTH: 74
<212> TYPE: DNA
<213> ORGANISM: Artificial sequence
<220> FEATURE:
<223> OTHER INFORMATION: Primer

<400> SEQUENCE: 49
ggatcctcta taaaggcatc tgtcagcttc gccaacgcat ccgccgcctt cgccgcaaaa    60
gcgctcagct ccgc    74

<210> SEQ ID NO 50
<211> LENGTH: 84
<212> TYPE: DNA
<213> ORGANISM: Artificial sequence
<220> FEATURE:
<223> OTHER INFORMATION: Primer

<400> SEQUENCE: 50
gaattcttaa agcttgcgct ggcggagctg ggcaatgcgc tggcggagct gggcaatgcg    60
ttggcggagc tgagcgcttt tgcg    84

<210> SEQ ID NO 51
<211> LENGTH: 38
<212> TYPE: PRT
<213> ORGANISM: Artificial sequence
<220> FEATURE:
<223> OTHER INFORMATION: Synthesized peptide

<400> SEQUENCE: 51

```
Tyr Lys Gly Ile Cys Gln Leu Arg Gln Arg Ile Arg Arg Leu Arg Arg
1               5                   10                  15
Lys Ser Ala Gln Leu Arg Gln Arg Ile Ala Gln Leu Arg Gln Arg Ile
                20                  25                  30
Ala Gln Leu Arg Gln Arg
                35
```